United States Patent [19]

Takasugi et al.

[11] Patent Number: 5,308,857
[45] Date of Patent: May 3, 1994

[54] FURYLTHIAZOLE DERIVATIVES, PROCESSES FOR THE PREPARATION THEREOF AND PHARMACEUTICAL COMPOSITION COMPRISING THE SAME

[75] Inventors: Hisashi Takasugi, Osaka; Yousuke Katsura, Toyonaka; Yoshikazu Inoue, Amagasaki; Tetsuo Tomishi, Minoo, all of Japan

[73] Assignee: Fujisawa Pharmaceutical Co., Ltd., Osaka, Japan

[21] Appl. No.: 908,795

[22] Filed: Jul. 6, 1992

Related U.S. Application Data

[63] Continuation of Ser. No. 711,727, Jun. 10, 1991, abandoned, which is a continuation of Ser. No. 476,572, Feb. 7, 1990, abandoned, which is a continuation-in-part of Ser. No. 385,100, Jul. 16, 1989, abandoned.

[30] Foreign Application Priority Data

Aug. 15, 1988 [GB] United Kingdom ............... 8819365
Mar. 14, 1989 [GB] United Kingdom ............... 8905818

[51] Int. Cl.$^5$ ............... C07D 417/04; A61K 31/425
[52] U.S. Cl. ............... 514/370; 514/223.2; 514/236.8; 514/342; 544/12; 544/133; 546/280; 548/181; 548/193; 548/194; 548/197

[58] Field of Search ............... 548/181, 193, 194, 197; 514/370, 223.2, 236.8, 342; 544/12, 133; 546/280

[56] References Cited

U.S. PATENT DOCUMENTS 4,720,443 1/1988 Kawakati ............... 514/230
4,814,341 3/1989 Reiter ............... 514/370

*Primary Examiner*—Robert Gerstl
*Attorney, Agent, or Firm*—Oblon, Spivak, McClelland, Maier & Neustadt

[57] ABSTRACT

The invention relates to compounds of the formula:

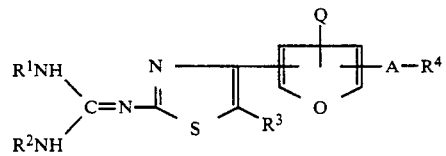

wherein $R^1$, $R^2$, $R^3$, $R^4$, A and Q are as described, useful in the treatment of ulcers.

8 Claims, No Drawings

FURYLTHIAZOLE DERIVATIVES, PROCESSES FOR THE PREPARATION THEREOF AND PHARMACEUTICAL COMPOSITION COMPRISING THE SAME

This application is a continuation of application Ser. No. 07/711,727, filed on Jun. 10, 1991, now abandoned, which is a continuation of application Ser. No. 07/476,572, filed on Feb. 7, 1990, now abandoned, which is a continuation-in-part of application Ser. No. 07/385,100, filed on Jul. 16, 1989, now abandoned.

This invention relates to new furylthiazole derivatives and pharmaceutically acceptable salts thereof.

More particularly, it relates to furylthiazole derivatives and pharmaceutically acceptable salts thereof which have antiulcer activity and $H_2$-receptor antagonism, to processes for the preparation thereof, to a pharmaceutical composition comprising the same and to a method for the treatment of ulcer in human being or animals.

Accordingly, one object of this invention is to provide new furylthiazole derivatives and pharmaceutically acceptable salts thereof which possess antiulcer activity and $H_2$-receptor antagonism.

Another object of this invention is to provide processes for the preparation of said furylthiazole derivatives and salt thereof.

A further object of this invention is to provide a pharmaceutical composition comprising, as an active ingredient, said furylthiazole derivatives or pharmaceutically acceptable salts thereof.

Still further object of this invention is to provide a therapeutical method for the treatment of ulcer in human being or animals.

The furylthiazole derivatives of this invention are new and can be represented by the following general formula (I):

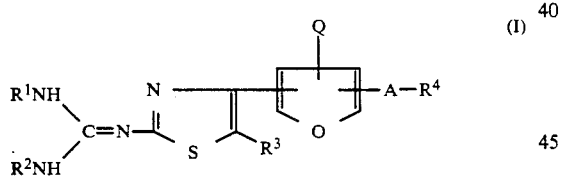

(I)

wherein $R^1$ and $R^2$ are each hydrogen, acyl or lower alkyl which may have halogen; or $R^1$ and $R^2$ are linked together to form lower alkylene, $R^3$ is hydrogen or lower alkyl, $R^4$ is amino, acyl, acylamino, lower alkylisothioureido, heterocyclic amino, heterocyclic group, or a group of the formula:

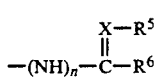

in which n is 0 or 1,

X is =CH— or =N—, $R^5$ is hydrogen, cyano, nitro or acyl, and $R^6$ is hydrogen, lower alkyl, lower alkylthio, lower alkoxy or amino which may have suitable substituent(s), and A is lower alkylene or —CONH—; or A—$R^4$ is heterocyclic group, and Q is hydrogen or lower alkyl.

The object compound (I) or a salt thereof can be prepared by processes as illustrated in the following reaction schemes.

Process 1

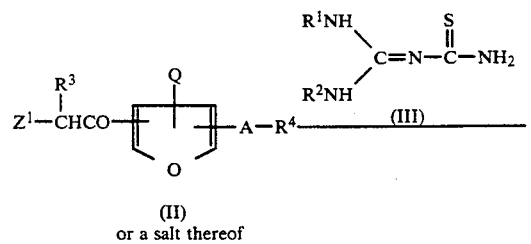

(II)
or a salt thereof

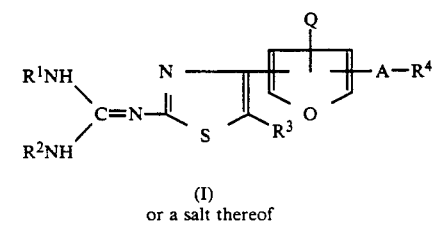

(I)
or a salt thereof

Process 2

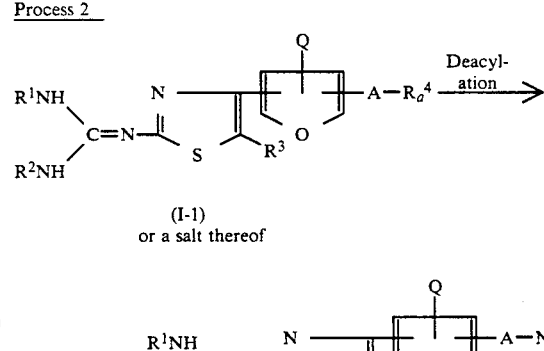

(I-1)
or a salt thereof (I-2)
or a salt thereof

Process 3

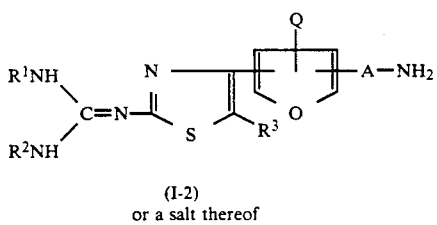

(I-2)
or a salt thereof

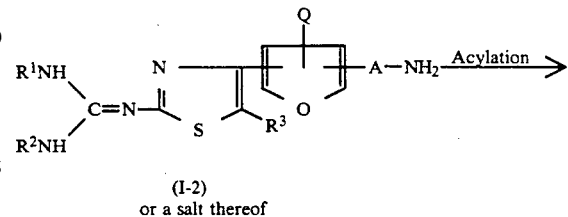

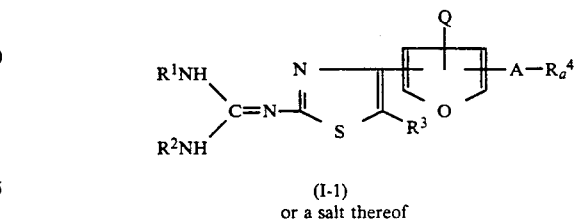

(I-1)
or a salt thereof

Process 4

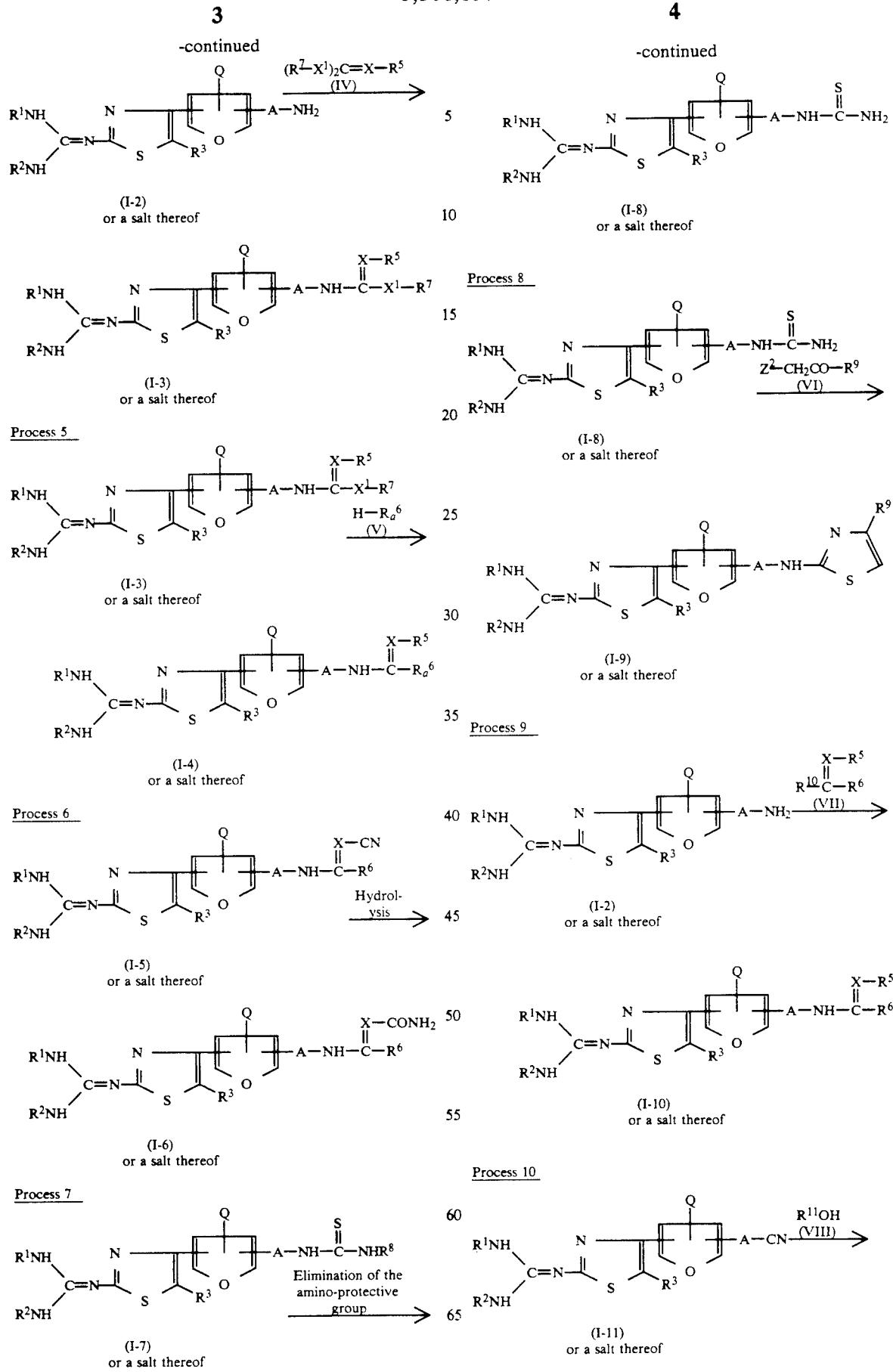

-continued
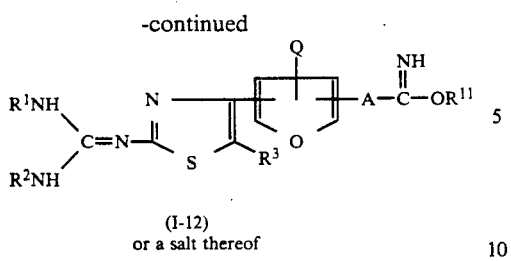
(I-12) or a salt thereof
Process 11
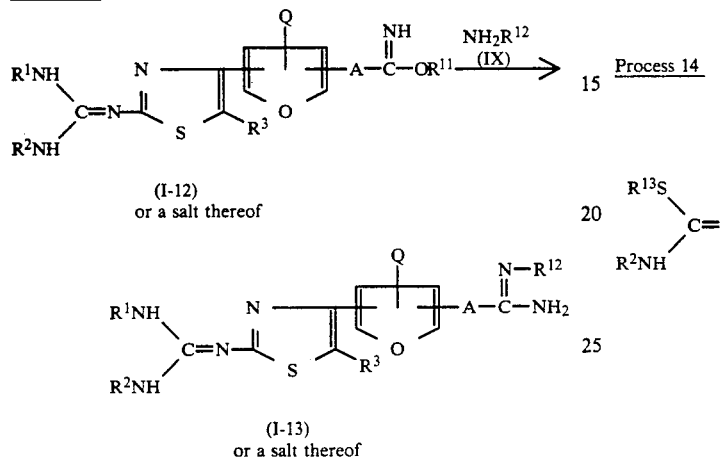
(I-12) or a salt thereof
(I-13) or a salt thereof
Process 12
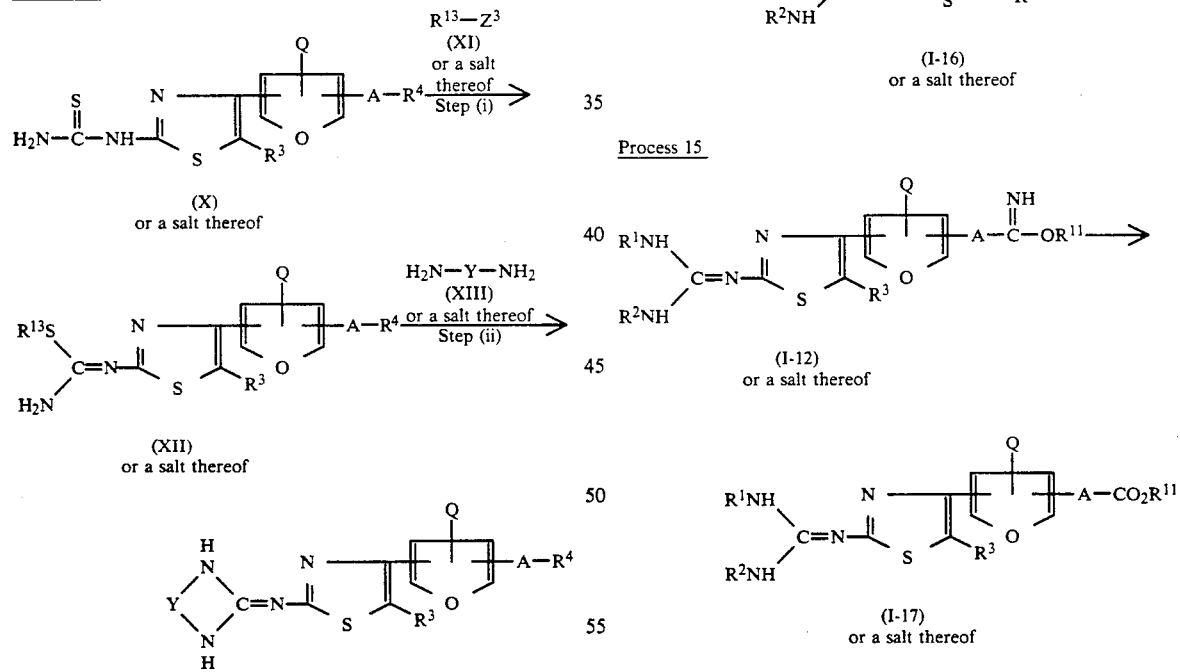
(X) or a salt thereof
(XII) or a salt thereof
(I-14) or a salt thereof
Process 13
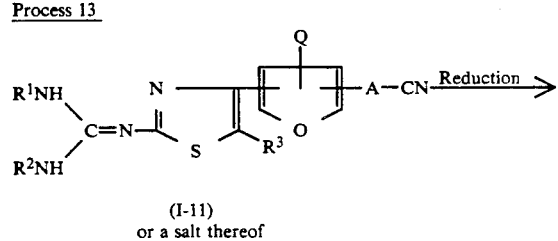
(I-11) or a salt thereof
-continued
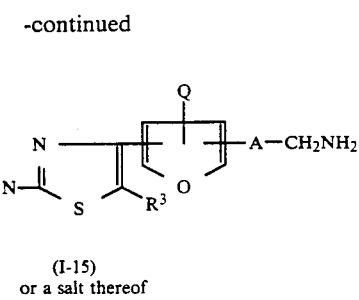
(I-15) or a salt thereof
Process 14
(XIV) or a salt thereof
(I-16) or a salt thereof
Process 15
(I-12) or a salt thereof
(I-17) or a salt thereof
Process 16
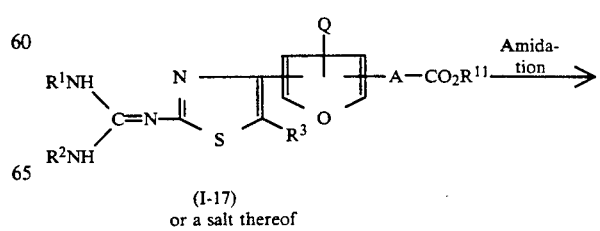
(I-17) or a salt thereof -continued

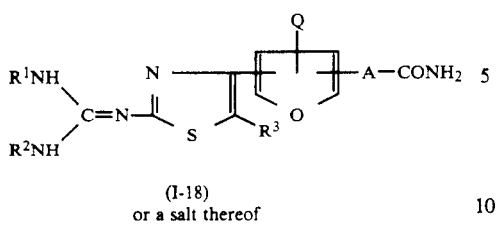

(I-18)
or a salt thereof

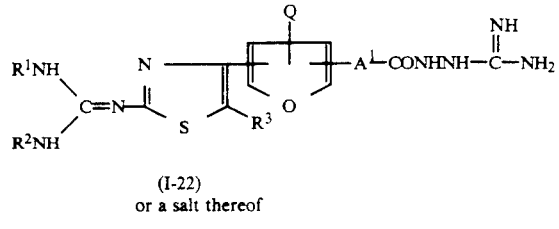

(I-22)
or a salt thereof

Process 17

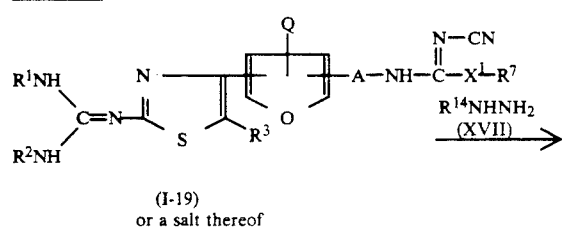

(I-19)
or a salt thereof

Process 20

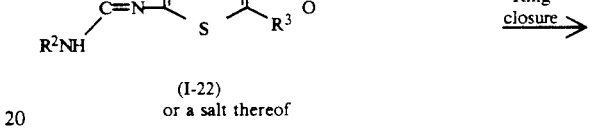

(I-22)
or a salt thereof

Ring closure →

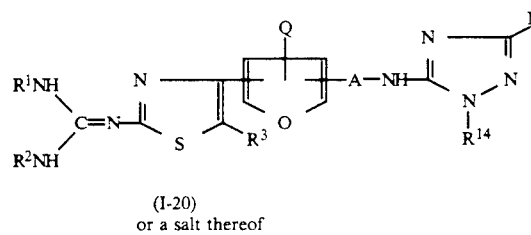

(I-20)
or a salt thereof

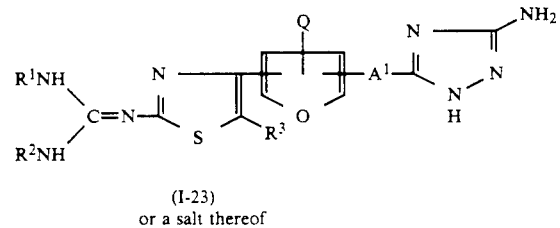

(I-23)
or a salt thereof

Process 18

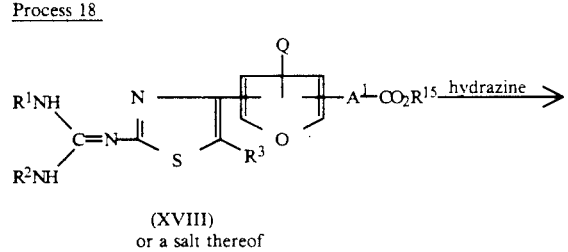

(XVIII)
or a salt thereof hydrazine →

Process 21

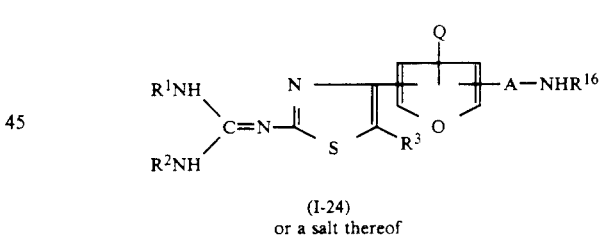

(I-2)
or a salt thereof $R^{16}-Z^4$
(XIX)
or a salt thereof
→

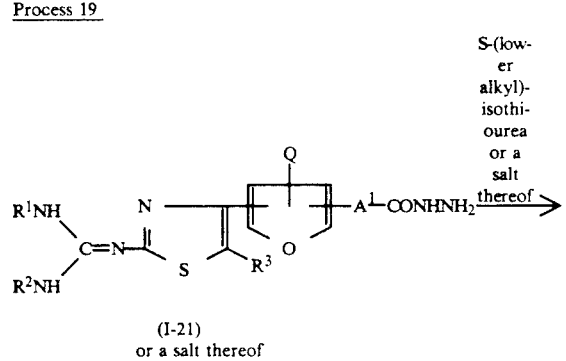

(I-21)
or a salt thereof

Process 19

(I-21)
or a salt thereof

S-(lower alkyl)-isothiourea or a salt thereof →

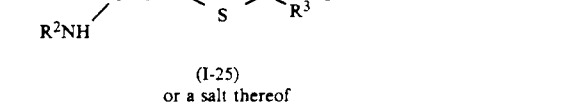

(I-24)
or a salt thereof

Process 22

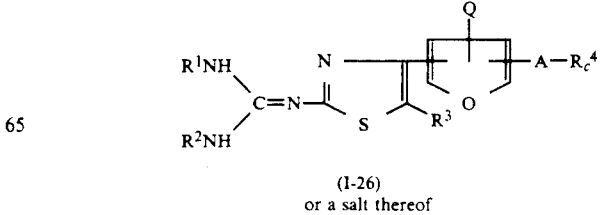

(I-25)
or a salt thereof

Oxidation →

(I-26)
or a salt thereof

-continued

Process 23

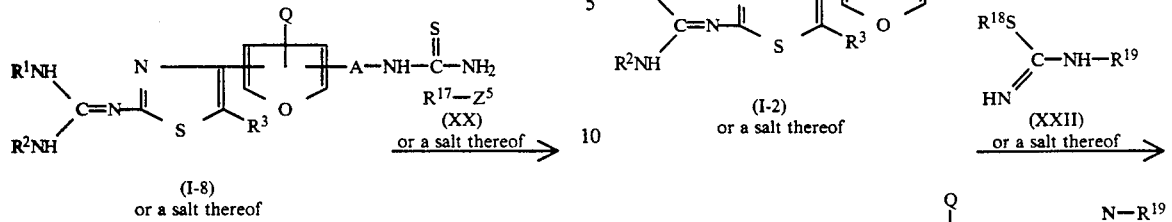

(I-8) or a salt thereof

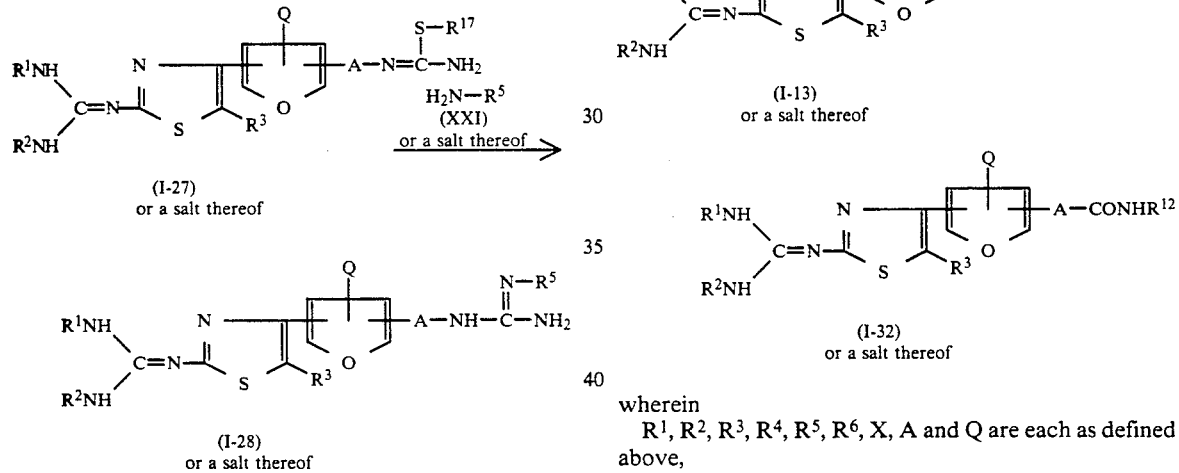

(I-27) or a salt thereof

Process 24

(I-27) or a salt thereof (I-28) or a salt thereof

Process 25

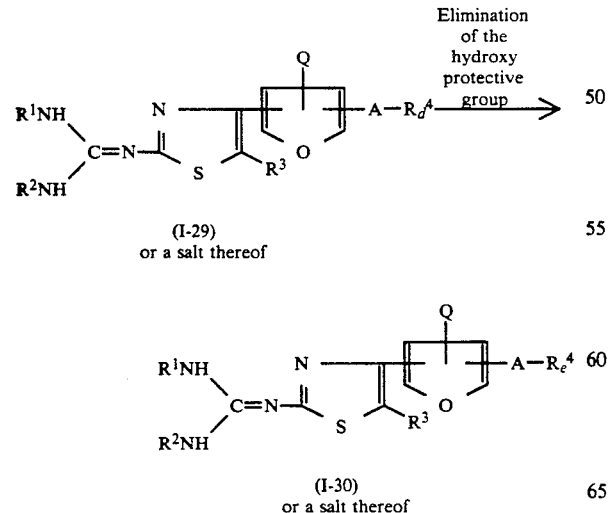

(I-29) or a salt thereof (I-30) or a salt thereof

Process 26

-continued

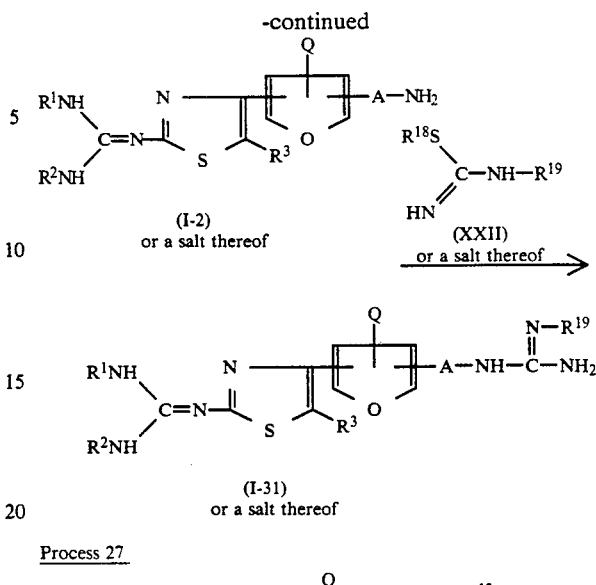

(I-2) or a salt thereof (I-31) or a salt thereof

Process 27

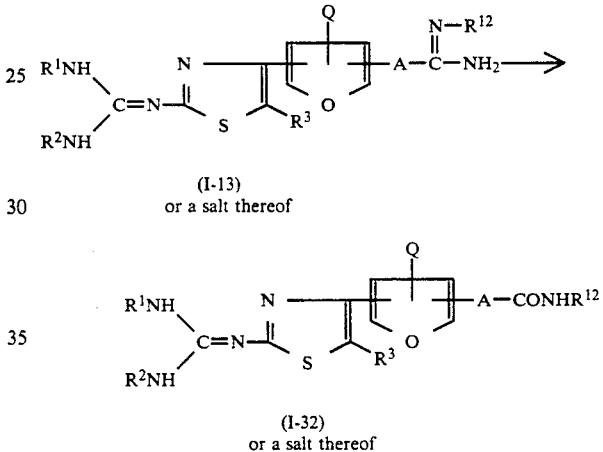

(I-13) or a salt thereof (I-32) or a salt thereof wherein
R$^1$, R$^2$, R$^3$, R$^4$, R$^5$, R$^6$, X, A and Q are each as defined above,
R$_a^1$ is lower alkyl which may have halogen,
R$_a^4$ is acylamino,
R$_b^4$ is acylamino including thio,
R$_c^4$ is acylamino including sulfinyl,
R$_d^4$ is acylamino including protected hydroxy,
R$_e^4$ is acylamino including hydroxy,
R$_a^6$ is amino which may have suitable substituent(s) or lower alkoxy,
R$^7$ is lower alkyl or aryl,
R$^8$ is amino-protective group,
R$^9$, R$^{11}$, R$^{13}$, R$^{15}$, R$^{17}$ and R$^{18}$ are each lower alkyl,
R$^{10}$ is protected hydroxy,
R$^{12}$ and R$^{19}$ are each acyl,
R$^{14}$ is hydrogen or lower alkyl,
R$^{16}$ is heterocyclic group,
X$^1$ is S or O,
Y is lower alkylene,
Z$^1$, Z$^2$, Z$^3$, Z$^4$ and Z$^5$ are each acid residue, and
A$^1$ is lower alkylene or bond.

In the above and subsequent description of the present specification, suitable examples of the various definitions to be included within the scope of the invention are explained in detail in the following.

The term "lower" is intended to mean a group having 1 to 6 carbon atom(s) preferably 1 to 4 carbon atom(s), unless otherwise provided.

Suitable "lower alkyl" and lower alkyl moiety in the term "lower alkylthio" may be a straight or branched one such as methyl, ethyl, propyl, isopropyl, butyl, isobutyl, tert-butyl, pentyl, hexyl or the like, in which the preferable one is $C_1$–$C_4$ alkyl and the more preferable one is methyl or ethyl.

Suitable "lower alkoxy" may be methyl, ethoxy, propoxy, isopropoxy, butoxy, isobutoxy, tert-butoxy, pentyloxy, hexyloxy or the like, in which the preferable one is $C_1$–$C_4$ alkoxy, the more preferable one is $C_1$–$C_2$ alkoxy and the most preferable one is methoxy.

Suitable "acyl" and the acyl moiety in the term "acylamino" may include carbomoyl, thiocarbamoyl, sulfamoyl, an aliphatic acyl, an aromatic acyl, a heterocyclic acyl and an aliphatic acyl substituted with aromatic or heterocyclic group(s) derived from carbamic, sulfonic, carboxylic or carbonic acids, and their thio acids.

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, isopropoxycarbonyl, butoxycarbonyl, tert-butoxycarbonyl, etc.), lower alkenyol (e.g. acryloyl, methacryloyl, crotonoyl, etc.), ($C_3$-$C_7$)-cycloalkanecarbonyl (e.g. cyclohexanecarbonyl, etc.), lower alkoxalyl (e.g. methoxalyl, ethoxalyl, etc.), lower alkanoylcarbonyl (e.g. pyruvoyl, etc.), and the like.

The aromatic acyl may include aroyl (e.g. benzoyl, nitrobenzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, 1-oxonicotinoyl, isonicotinoyl, thiazolylcarbonyl, thiadiazolylcarbonyl, tetrazolycarbonyl, morpholinocarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolyacetyl, furylacetyl, tetrazolylacetyl, thiazolyacetyl, thiadiazolylacetyl, thienylpropionyl, thiadiazolylpropionyl, and the like.

These acyl groups may be further substituted with suitable substituent(s) such as hydroxy, amino, carboxy, lower alkyl (e.g. methyl, ethyl, propyl, isopropyl, butyl, pentyl, hexyl, hexyl, etc.), lower alkenyl (e.g. vinyl, allyl, etc.), halogen (e.g. chloro, bromo, iodo, fluoro), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), heterocyclic(lower)alkylthio (e.g. furylmethylthio, thiazolymethylthio, etc.), heterocyclic(lower)alkylsulfinyl (e.g. furylmethylsulfinyl, thiazolylmethylsulfinyl, etc.), nitro, acyl as mentioned above, protected amino in which the amino protective moiety may be the same as those herein, aryl (e.g. phenyl, etc.), aroyl (e.g. benzoyl, etc.), aryloxy (e.g., benzyloxy, tolyloxy, etc.), protected hydroxy such as acyloxy, for example, lower alkanyloxy (e.g. formyloxy, acetyloxy, propionyloxy, butyryloxy, isobutyryloxy, valeryloxy, isovaleryloxy, pivaloyloxy, hexanoyloxy, etc.), lower alkylamino (e.g. methylamino, ethylamino, etc.), amino-protective group as beforementioned, and the like, and the preferable acyl having such substituent(s) may be lower alkoxy(lower)alkanoyl (e.g., methoxyacetyl, ethoxyacetyl, etc.), lower alkanoyloxy(lower)alkanoyl (e.g., acetoxyacetyl, etc.), N-lower alkylcarbamoyl (e.g. N-methylcarbamoyl, N-ethylcarbamoyl, N-isopropylcarbamoyl, etc.), aroylthiocarbamoyl (e.g. benzoylthiocarbamoyl, etc.), etc.

Suitable "heterocyclic group" and heterocyclic moiety in the term "heterocyclic amino" may include saturated or unsaturated, monocyclic or polycyclic heterocyclic group containing at least one hetero-atom such as an oxygen, sulfur nitrogen atom and the like. Especially preferably heterocyclic group may be 5 or 6-membered aromatic heteromonocyclic group (e.g. pyrrolyl, imidazolyl, pyrazolyl, triazolyl, tetrazolyl, pyridyl, pyrazinyl, pyrimidinyl, pyridazinyl, thiazolyl, thaidiazolyl, etc.), 5- or 6-membered aliphatic heteromonocyclic group (e.g. morpholinyl, pyrrolidinyl, imidazolidinyl, pyrazolidinyl, piperidyl, piperazinyl, etc.), unsaturated condensed heterocyclic group containing 1 to 2 sulfur atom(s) and 1 to 3 nitrogen atom(s) (e.g. benzothiazoly, benzothiadiazolyl, etc.), and the like. Thus defined heterocyclic moiety may have suitable substitutent(s) such as amino, oxo, halogen as chloro, lower alkyl as defined above, and the like. Preferable example of such a group is thiazolyl having lower alkyl (e.g. 4-methylthiazolyl, etc.).

Suitable "amino-protective group" may include ar(lower)alkyl such as benzyl, benzhydryl, phenethyl and the like, and acyl as mentioned above.

Suitable hydroxy-protective group in the term "protected hydroxy" may include aforesaid acyl, ar(lower)alkyl (e.g. benzyl, trityl, etc.) lower alkoxy(lower)alkyl (e.g. methoxymethyl, 1-methyl-1-methoxyethyl, methoxypropyl, etc.), tetrahydropyranyl, lower alkyl s aforementioned and the like.

Suitable "acid residue" may include halogen such as chloro, bromo, fluoro and iodo.

Suitable "lower alkylene" and lower alkylene moiety formed by linkage of $R^1$ and $R^2$ may be straight or branched one such as methylene, ethylene, trimethylene, propylene, tetramethylene, pentamethylene, hexamethylene, and the like, in which the preferable one is $C_1$-$C_4$ alkylene and the most preferable one is ethylene.

Suitable "lower alkyl which may have halogen" may include lower alkyl as mentioned above, mono or di or trihalo(lower)alkyl such as trifluoro(lower)alkyl (e.g. trifluoromethyl, trifluoroethyl, etc).

Suitable "lower alkylisothioureido" may include 2-lower alkylisothioureido such 2-methylisothioureido 2-ethylisothioureido, 3-propylisothioureido, and the like.

Suitable "amino which may have suitable substituent(s)" is conventional one used in a pharmaceutical field and may include amino, mono or di(lower)alkylamino (e.g. methylamino, dimethylamino, ethylamino, butylamino, etc.), lower alkenylamino (e.g. vinylamino, propenylamino, etc.), lower alkynylamino (e.g. ethylnylamino, propynylamino, etc.), hydroxy(lower)-alkylamino (e.g. hydroxymethylamino, hydroxyethylamino, hydroxypropylamino, etc.), lower alkoxy(lower)alkylamino (e.g. methoxymethylamino, etc.), mono or di(lower)-alkylamino(lower) alkylamino (e.g. methylaminomethylamino, dimethylaminoethylamino, etc.), and the like.

Suitable "acylamino including thio" may include acylamino as mentioned above, in which the optional carbon atom of the acyl moiety is replaced by a thio group, for example, heterocyclic(lower)alkylthio(-lower)alkanoylamino such as 5- or 6-membered aromatic heteromonocyclic(lower)-alkylthio(lower)alkanoylamino (e.g. furylmethylthioacetylamino, thiazolylmethylthioacetylamino, etc.), and the like.

Suitable "acylamino including sulfinyl" may include acylamno as mentioned above, in which the optional carbon atom of the acyl moiety is replaced by a sulfinyl group, for example, heterocyclic(lower)alkylsulfinyl(-lower)-alkanoylamino such as 5- or 6-membered aromatic heteromonocyclic(lower)alkylthio(lower)alkanoylamino (e.g. furylmethylsulfinylacetylamino, thiazolylmethylsulfinylacetylamino, etc.), and the like.

Suitable "acylamino including protected hydroxy" may include acylamino as mentioned above which is substituted by a protected hydroxy as exemplified above, for example, protected hydroxy(lower)alkylureido such as lower alkanoyloxy(lower)alkylureido (e.g. acetyloxyethylureido, etc.), and the like.

Suitable "acylamino including hydroxy" may include acylamino as mentioned above which is substituted by hydroxy such as hydroxy(lower)alkylureido (e.g. hydroxyethylureido, etc.), and the like.

Suitable "aryl" may include phenyl, tolyl, xylyl, mesityl, cumenyl, naphthyl, and the like, in which the preferred one is $C_6-C_{10}$ aryl.

Suitable pharmaceutically acceptable salts of the object compound (I) are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt, [e.g. hydrochloride, hydrobromide, sulfate, phosphate, etc.], a salt with an acidic amino acid [e.g. aspartic acid salt, glutamic acid salt, etc.], and the like.

With respect to the salt of the compound (I-1) to (I-32) in the processes 1 to 27, it is to be noted that these compounds are included within the scope of the compound (I), and accordingly the suitable examples of the salts of these compounds are to be referred to those as exemplified for the object compound (I).

Particularly, the preferred embodiments of $R^1$, $R^2$, $R^3$, $R^4$, $R^5$, $R^6$, A, X, n and Q are as follows.

$R^1$ is hydrogen; acyl such as heterocyclic carbonyl, more preferably 5- or 6-membered heteromonocyclic-carbonyl (e.g. furoyl, etc.); lower alkyl which may have halogen such as lower alkyl (e.g. methyl, ethyl, etc.), trihalo(lower)-alkyl (e.g. trifluoromethyl, trifluoroethyl, etc.);

$R^2$ is hydrogen; or $R^1$ and $R^2$ are linked together to form lower alkylene (e.g. methylene, ethylene, etc.);

$R^3$ is hydrogen; lower alkyl (e.g. methyl, etc.);

$R^4$ is amino; acyl such as carbamoyl, aminocarbamoyl, guanidinocarbamoyl, lower alkylcarbamoyl (e.g. methylcarbamoyl, etc.), sulfamoylaminocarbonyl, lower alkoxycarbonyl (e.g. methoxycarbonyl, etc.); acylamino, for example, ureido, thioureidosulfamoylamino, lower alkanoylamino (e.g. formylamino, acetylamino, propionylamino, butyrylamino, isobutyrylamino, valerylamino, etc.), lower alkoxycarbonylamino (e.g. methoxycarbonylamino, etc.), lower alkylsulfonylamino (e.g. mesylamino, etc.), lower alkoxy(lower)alkanoylamino (e.g. methoxyacetylamino, etc.), protected hydroxy(lower)alkanoylamino such as lower alkanoyloxy(lower)alkanoylamino (e.g. acetoxyacetylamino, etc.), lower alkylthio(lower)alkanoylamino (e.g. methylthioacetylamino, etc.), aroylamino optionally substituted such sa $C_6-C_{10}$ aroylamino optionally substituted by nitro (e.g. nitrobenzoylamino, etc.), (5- or 6-membered heteromonocyclic-carbonylamino (e.g. furoylamino, thenoylamino, nicotinoylamino, 1-oxonicotinoylamino, morpholinocarbonylamino, etc.), lower alkylureido such as 3-lower alkylureido (e.g. 3-methylureido, 3-ethylureido, 3-propylureido, 3-isopropylureido, etc.), lower alkylthioureido such as 3-lower alkylthioureido (e.g. 3-methylthioureido, etc.), lower alkanoylureido such as 3-lower alkanoylureido (e.g. 3-acetylureido, etc.), lower alkenylureido such as 3-lower alkenylureido (e.g. 3-propenylureido, etc.) aroylthioureido such as $C_6-C_{10}$ aroylthioureido (e.g. 3-benzoylthioureido, etc.), 5- or 6-membered aromatic heteromonocyclic-(lower)-alkylthio(lower)alkanoylamino such as furyl(lower)-alkylthio(lower)alkanoylamino (e.g. furylmethylthioacetylamino, etc.), 5- or 6-membered aromatic heteromonocyclic-(lower)alkylsulfinyl(lower)-alkanoylamino such as furyl(lower)alkylsulfinyl-(lower)alkanoylamino (e.g. furylmethylsulfinylacetylamino, etc.), mono or di(lower)alkylsulfamoylamnio(e.g. methylsulfamoylamino, dimethylsulfamoylamino, etc.), hydroxy-(lower)alkylureido such as 3-hydroxy(lower)-alkylureido (e.g. 3-hydroxyethylureido, etc.), protected hydroxy(lower)alkylureido such as 3-lower alkanoyloxy(lower)alkylureido (e.g. 3-acetoxyethylureido, etc.); lower alkylisothioureido such as 2-lower alkylisothioureido (e.g. 2-methylisothioureido, etc.); heterocyclic amino, for example, optionally benzene-fused 5- or 6-heteromonocyclic-amino which may be substituted by one or more substituted selected from lower alkyl, amino, halogen and oxo such as thiazoylamino substituted with lower alkyl (e.g. 4-methylthiazolylamino, etc.), triazolylamino substituted with amino and/or lower alkyl (e.g. 3-aminotriazolylamino, 3-amino-1-methyltriazolylamino, etc.), benzoisothiazolylamino substituted with oxo (e.g. 1,1-dioxobenzoisothiazolylamino, etc.), benzothiadiazinylamino substituted with ono and halogen (e.g. 1,1-dioxochlorobenzothiadiazinylamino); heterocyclic group, for example, 5- or 6-membered heteromonocyclic group such as pyrimidinyl substituted with oxo and lower alkyl (e.g. 6-methyl-5-pentyl-4(1H)-pyrimidinon-2-yl, etc.) triazolyl substituted with amino (e.g. 3-aminotriazolyl, etc.); a group of the formula:

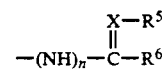

wherein
n is 0 or 1;
X is =CH— or =N—;
$R^5$ is hydrogen; cyano; nitro; or acyl such as carbamoyl, lower alkoxy-carbonyl (e.g. methoxycarbonyl, etc.), sulfamoyl, lower alkylsulfonyl (e.g. mesyl, ethylsulfonyl, etc.), arenesulfonyl more preferably $C_6-C_{10}$ arenesulfonyl, which is substituted with one or more substituent(s) selected from lower alkyl, lower alkoxy, halogen and amino (e.g. tosyl, methoxyphenylsulfonyl, bromophenylsulfonyl, aminophenylsulfonyl, etc.), mono or di(lower)alkylsulfamoyl (e.g. methylsulfamoyl, dimethylsulfamoyl, etc.); and $R^6$ is hydrogen; lower alkyl (e.g. methyl, etc.); lower alkylthio (e.g. methylthio, etc.); lower alkoxy (e.g. methoxy, etc.); amino which may have suitable substituent(s) selected from, mono or di(lower)alkyl (e.g. methyl, dimethyl, butyl, etc.), lower alkenyl (e.g. propenyl, etc.), lower alkynyl (e.g. propynyl, etc.), hydroxy(lower)alkyl (e.g. hydroxyethyl, hydroxypropyl, etc.), lower alkoxy(lower)alkyl (e.g. methoxyethyl, etc.) and mono or di-(lower)alkylamino(lower)alkyl (e.g. dimethylaminoethyl, etc.);

A is lower alkylene (e.g. methylene, ethylene, etc.);

—CONH—;

or

A—$R^4$ is heterocyclic group such as imidazolyl substituted with lower alkyl (e.g. 2-methylimidazolyl, etc.), triazolyl substituted with amino (e.g. 3-amino-1,2,4-triazolyl, etc.); and Q is hydrogen; or lower alkyl (e.g. methyl, etc.).

The processes for preparing the object compounds (I) of the present invention are explained in detail in the following.

PROCESS 1

The object compound (I) or a salt thereof can be prepared by reacting the compound (II) or a salt thereof with the compound (III).

This reaction is usually conducted in a conventional solvent which does not adversely influence the reaction such as ethyl acetate, dichloromethane, chloroform, carbon tetrachloride, tetrahydrofuran, N,N-dimethylformamide, N,N-dimethylacetamide, dioxane, water, alcohol [e.g. methanol, ethanol, etc.] acetic acid, formic acid, etc. or a mixture thereof.

The reaction temperature is not critical and the reaction is usually conducted under cooling to heating.

PROCESS 2

The object compound (I-2) or a salt thereof can be prepared by subjecting the compound (I-1) or a salt thereof to deacylation.

Suitable method for this deacylation reaction may include conventional one such as hydrolysis, reduction, or the like. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as tri(lower)alkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,2]-octane, 1,5-diazabicyclo[5,4,0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

PROCESS 3

The object compound (I-1) or a salt thereof can be prepared by reacting the compound (I-2) or a salt thereof with an acylating agent.

The compound (I-2) may be used in the form of its conventional reactive derivative at the amino group.

The acylating agent can be represented by the compound of the formula:

$$R^{20}-OH$$

in which $R^{20}$ is acyl as defined above and its conventional reactive derivative at the hydroxy group.

The suitable example may be an acid halide (e.g. acid chloride, etc.), an acid anhydride, an activated amide, an activated ester, and the like.

In case the acyl group to be introduced is a carbamoyl type acyl, the acylating agent is usually used in the form of cyanate or isocyanate.

The reaction is usually carried out in a conventional solvent such as water, alcohol [e.g. methanol, ethanol, etc.] acetone, dioxane, acetonitrile, chloroform, dichloromethane, ethylene chloride, tetrahydrofuran, ethyl acetate, N,N-dimethylformamide, N,N-dimethylacetamide, pyridine, acetic acid or any other organic solvent which does not adversely influence the reaction. These conventional solvents may also be used in a mixture with water.

The reaction temperature is not critical, and the reaction is usually carried out under cooling to warming.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like.

PROCESS 4

The object compound (I-3) or a salt thereof can be prepared by reacting the compound (I-2) or a salt thereof with the compound (IV).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 5

The object compound (I-4) or a salt thereof can be prepared by reacting the compound (I-3) or a salt thereof with the compound (V).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

In case that the compound (V) is liquid, it can be also used as a solvent.

The reaction temperature is not critical, and the reaction is usually carried out at ambient temperature or under warming or heating.

PROCESS 6

The object compound (I-6) or a salt thereof can be prepared by subjecting the compound (I-5) or a salt thereof to hydrolysis reaction.

This reaction is usually carried otu in a conventional manner for transforming nitrile to amide.

This reaction is usually carried out in a conventional solvent which does not adversely influence the reaction such as water, alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 7

The object compound (I-8) or a salt thereof can be prepared by subjecting the compound (I-7) or a salt thereof to elimination reaction of the amino-protective group.

This reaction can be carried out in substantially the same manner as Process 2, and therefore the reaction mode and reaction conditions [e.g. solvent, reaction temperature, etc.] of this reaction are to be referred to those as explained in Process 2.

PROCESS 8

The object compound (I-9) or a salt thereof can be prepared by reacting the compound (I-8) or a salt thereof with the compound (VI).

This reaction can be carried out in substantially the same manner as Process 1, and therefore the reaction mode and the reaction conditions [e.g. solvent, reaction temperature, etc.] of this reaction are to be referred to those as explained in Process 1.

PROCESS 9

The object compound (I-10) or a salt thereof can be prepared by reacting the compound (I-2) or a salt thereof with the compound (VII).

This reaction is usually carried out in a conventional solvent which does not adversely influence the reaction such as alcohol [e.g. methanol, ethanol, propanol, etc.], tetrahydrofuran, dioxane, dimetyl sulfoxide, N,N-dimethylformamide or a mixture thereof.

The reaction temperature is not critical, and the reaction is usually carried out at ambient temperature or under warming or heating.

PROCESS 10

The object compound (I-12) or a salt thereof can be prepared by reacting the compound (I-11) or a salt thereof with the compound (VIII).

This reaction is usually carried out in the presence of dry hydrogen chloride gas.

The reaction is usually carried out in a conventional solvent such as alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out under cooling to heating.

The object compound (I-12) can be used as a starting compound of Process 15 mentioned hereinbelow with or without isolation.

Process 11

The object compound (I-13) or a salt thereof can be prepared by reacting the compound (I-12) or a salt thereof with the compound (IX).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 12-(i)

The compound (XII) or a salt thereof can be prepared by reacting the compound (X) or a salt thereof with the compound (XI) or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temeprature or under warming or heating.

Process 12-(i)

The object compound (I-14) or a salt thereof can be prepared by reacting the compound (XII) or a salt thereof with the compound (XIII) or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 13

The object compound (I-15) or a salt thereof can be prepared by subjecting the compound (I-11) or a salt thereof to reduction.

The reduction may include, for example, reduction with an alkali metal borohydride (e.g. sodium borohydride, etc.), and the like.

This reaction is usually carried out in a conventional solvent which does not adversely influence the reaction such as alcohol [e.g. methanol, ethanol, propanol, etc.], tetrahydrofuran dioxane, dimethyl sulfoxide, N,N-dimethylformamide or a mixture thereof.

The reaction temperature is not critical, and the reaction is usually carried out under cooling to heating.

PROCESS 14

The object compound (I-16) or a salt thereof can be prepared by reacting the compound (XIV) or a salt thereof with the compound (XV) or a salt thereof.

This reaction can be carried out in substantially the same manner as Process 5, and therefore the reaction mode and reaction conditions [e.g. solvent, reaction temperature, etc.] of this reaction are to be referred to those as explained in Process 5.

PROCESS 15

The object compound (I-17) or a salt thereof can be prepared by subjecting the compound (I-12) or a salt thereof to hydrolysis.

This reaction is usually carried out in a conventional solvent such as a mixture of water and alcohol [e.g. methanol, etc.] or any other solvent which does not adversely influence the reaction.

The reaction temperature is not critical, and the reaction is usually carried out under cooling to heating.

PROCESS 16

The object compound (I-18) or a salt thereof can be prepared by subjecting the compound (I-17) or a salt thereof to amidation.

This reaction is usually carried out in the presence of ammonia gas.

This reaction is usually carried out in a conventional solvent such as alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out at ambient temperature or under warming or heating.

PROCESS 17

The object compound (I-20) or a salt thereof can be prepared by reacting the compound (I-19) or a salt thereof with the compound (XVII).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 18

The object compound (I-21) or a salt thereof can be prepared by reacting the compound (XVIII) or a salt thereof with hydrazine.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 19

The object compound (I-22) or a salt thereof can be prepared by reacting the compound (I-21) or a salt thereof with S-(lower)alkylisothiourea or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 20

The object compound (I-23) or a salt thereof can be prepared by subjecting the compound (I-22) or a salt thereof to ring closure.

This reaction is usually carried out in the presence of ammonium hydride.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 21

The object compound (I-24) or a salt thereof can be prepared by reacting the compound (I-2) or a salt thereof with the compound (XIX or a salt thereof.

The reaction is usually carried out in a conventional solvent such as water, acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction. These conventional solvents may also be used in a mixture with water.

The reaction temperature is not critical, and the reaction is usually carried out under cooling to warming.

The reaction may also be carried out in the presence of an inorganic or organic base such as an alkali metal bicarbonate, tri(lower) alkylamine (e.g. triethylamine, etc.), pyridine, N-(lower)alkylmorphorine, N,N-di(-lower)alkylbenzylamine, or the like.

PROCESS 22

The object compound (I-26) or a salt thereof can be prepared by oxidizing the compound (I-25) or a salt thereof.

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone, hydrogen peroxide. urea-hydrogen peroxide, N-halosuccinimide (e.g. N-bromosuccinimide, N-chlorosuccinimide, etc.), hypochlorite compound (e.g. tert-butyl hypochlorite, etc.), permanganate (e.g. potassium permanganate, etc.), or any other conventional oxidizing agent which can oxidide a sulfide group to a sulfoxide group.

The present reaction can also be carried out in the presence of a compound comprising Group Vb or VIb metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol, tetrahydrofuran, N,N-dimethylformamide or a mixture thereof.

The reaction temperature is not critical and the reaction is preferably carried out under cooling to at ambient temperature.

PROCESS 23

The object compound (I-27) or a salt thereof can be prepared by reacting the compound (I-8) or a salt thereof with the compound (XX) or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

PROCESS 24

The object compound (I-28) or a salt thereof can be prepared by reacting the compound (I-27) or a salt thereof with the compound (XXI) or a salt thereof.

This reaction can be carried out in substantially the same manner as Process 5, and therefore the reaction mode and reaction conditions [e.g. solvent, reaction temperature, etc.] of this reaction are to be referred to those as explained in Process 5.

PROCESS 25

The object compound (I-30) or a salt thereof can be prepared by subjecting the compound (I-29) or a salt thereof to elimination reaction of the hydroxy-protective group.

This reaction can be carried out in substantially the same manner as Process 2, and therefore the reaction mode and reaction conditions [e.g. solvent, reaction temperature, etc.] of this reaction are to be referred to those as explained in Process 2.

PROCESS 26

The object compound (I-31) or a salt thereof can be prepared by reacting the compound (I-2) or a salt thereof with the compound (XXII) or a salt thereof.

This reaction is usually carried out in a conventional solvent which does not adversely influence the reaction such as alcohol [e.g. methanol, ethanol, propanol, etc.] tetrahydrofuran, dioxane, dimethyl sulfoxide, N,N-dimethylformamide or a mixture thereof.

The reaction temperature is not critical, and the reaction is usually carried out at ambient temperature or under warming or heating.

The reaction may also be carried out in the presence of an inorganic or organic base such as tri(lower)alkylamine (e.g. triethylamine, etc.), or the like.

PROCESS 27

The object compound (I-32) or a salt thereof can be prepared by subjecting the compound (I-13) or a salt thereof to hydrolysis.

The hydrolysis is preferably carried out in the presence of a base or an acid.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Among the starting compounds, some of them are new and such compounds can be prepared by the methods of Preparation mentioned below and by any process known in the art for preparing structurally analogous compounds thereto.

The compounds obtained by the above Processes 1 to 27 can be isolated and purified by a conventional method such as pulverization, recrystallization, column chromatography, reprecipitation or the like.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

Furthermore, with regard to the compound (I), it is to be noted that the following formula(A) is well known to lie to tautomeric relation with the following formula (B), and accordingly, it is to be understood that both of the isomers are substantially the same.

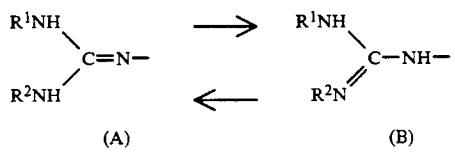

Accordingly, the both of the tautomeric forms are clearly included within the scope of the present invention. In the present specification, the object and starting compounds including the group of such tautomeric isomers are represented by using one of the expressions.

The new furylthiazole derivatives (I) and pharmaceutically acceptable salts thereof possess antiulcer activity and $H_2$-receptor antagonism, and are useful for a therapeutic treatment of gastritis, ulcer (e.g. gastric ulcer, duodenal ulcer, anastomotic ulcer, etc.), Zollinger-Ellison syndrome, reflux esophagitis, upper gastrointestinal bleeding, and the like.

And further, the compound (I) and pharmaceutically acceptable salts thereof of the present invention possess high antimicrobial activity against pathogenic microorganisms such as Campylobacter pyloridis, which is a gram-negative bacillus that has recently been found beneath the mucus gel of the human stomach.

For therapeutic purpose, the compound (I) and a pharmaceutically acceptable salt thereof of the present invention can be used in a form of pharmaceutical preparation containing one of said compounds, as an active ingredient, inadmixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating ulcer. In general, amounts between 0.1 mg/body and about 1,000 mg/body may be administered per day.

In order to illustrate the usefulness of the object compound (I), the pharmacological test data of some representative compounds of the compound (I) are shown in the following.

Test Compounds
(a) 4-(5-Acetylaminomethylfuran-2-yl)-2-(diaminomethyleneamino)thiazole
(b) 4-[5-(2-Cyano-3-methylguanidino)methylfuran-2-yl]-2-(diaminomethyleneamino)thiazole
(c) 2-(Diaminomethyleneamino)-4-[5-(3-methylureido)-methylfuran-2-yl]thiazole
(d) 4-[5-(2-Amino-2-aminosulfonyliminoethyl)furan-2-yl]-2-(diaminomethyleneamino)thiazole Test A (Gastric secretion in Heidenhain pouch dogs):
Test Method Beagle dogs, weighing about 8-13 kg, were used for the study on gastric secretion. The animals were surgically provided with a vagally denervated Heidenhain pouch. One month or more later, the dogs were fasted overnight. Gastric secretion was stimulated by an intravenous infusion of tetragastrin (10 μg/kg/hr). Gastric samples were collected at 15 min intervals. After its volume was almost constant, test compound (3.2 mg/kg) suspended in 0.1% methyl cellulose solution was administered orally. Acid concentration was determined by titrating an aliquot to pH 7.0 with 0.1N sodium hydroxide solution using automatic titration (Hiranuma RAT-11 Type). Total acid output was calculated by multiplying total volume of gastric samples by acid concentration, and percentage change of total acid output was calculated by comparing with predosing value of test compound.

Test Result

| Test Compound | Inhibition (%) |
| --- | --- |
| (a) | 100 |

Test B (H$_2$-receptor antagonism in isolated guinea-pig atrium):
Test Method

The atrial strip isolated from guinea-pig was suspended under an initial tension 0.3 to 0.6 g in an organ bath containing Tyrode solution at 30° C., aerated 95% O$_2$-5% CO$_2$ gas. The beating rate and amplitude of contraction of the atrium were recorded by means of a transducer and a polygraph. Histamine (1×10$^{-6}$ g/ml) was added to the bathing fluid and the increase in beating rate after dosing was measured. Addition of test compounds (1×10$^{-6}$ g/ml) was made 30 minutes after washing out histamine. Inhibitory effect of test compound was calculated by comparing histamine-induced increases in beating rate before and 30 minutes after dosing with the test compounds.

Test Results

| Test Compound | H$_2$ Antagonism (%) |
| --- | --- |
| (b) | 90.7 |
| (c) | 89.1 |

Test C (Inhibition of stress ulcer):
Test Method

Five male Sprague-Dawley rats, aged 7 weeks and weighing about 200 g were used per group for the study on stress ulcer after the fast for 24 hours. Each animal was immobilized in a restrain cage and immersed to a level of the xiphoid in a water bath kept 22° C. Each of the test compounds (32 mg/kg) suspended in 0.1% methylcellulose solution was administered orally just before the immobilization. Seven hours later, the animals were sacrificed and their stomachs were removed. The stomach was then fixed with 2% formalin. The area of ulcers was measured for each animal, and percentage of inhibition was calculated by comparing the mean area of ulcers (mm$^2$) in the test animals with that in the control animals.

Test Result

| Test Compound | Inhibition (%) |
| --- | --- |
| (d) | 86.6 |

Test D (Gastric secretion from lumen perfused stomach in anesthetized rats):
Test Method Male Sprague-Dawley rats weighing about 250 g were used. Rats were deprived of food but allowed free access to water for 24 hours. The animals were anesthetized with 1.25 g/kg urethane intraperitoneally. The abdomen was opened and the gastric lumen was perfured with saline throughout the experiment. The perfusate was titrated by an autotitrator with 25 mM sodium hydroxide as titrant. Gastric secretion was stimulated by intravenous infusion with histamine (3 mg/kg/hr). After reaching plateau, test compound (1 mg/kg) was given intravenously. Drug effect was expressed as maximal inhibition by acid output.

Test Result

| Test Compound | Inhibition (%) |
| --- | --- |
| (d) | 99 |

Test E (Anti-microbial activity):
Test Method

In vitro antimicrobial activity was determined by the agar dilution method. Test strain was precultured in Brucella broth containing 5% horse serum at 37° C. for 3 days 10$^4$ cfu were inoculated with a multipoint replicater onto Brucella agar plus 5% lysed horse blood plate containing serial 2-fold dilutions of each drug at 37° C. for 3 days. Incubation was carried out in an atmosphere of 10% CO$_2$. MIC was read after incubation as the lowest drug concentration that inhibited macroscopic colonial growth.

Test Result

| | MIC (μg/ml) | |
| --- | --- | --- |
| Test Compound | | (a) |
| Test strain | | |
| Campylobacter pyloridis 8008 | | 12.5 |

The following Preparations and Examples are given for the purpose of illustrating the present invention in more detail.

PREPARATION 1

Aluminum chloride (34.1 g) was added to a mixture of 2-furylacetonitrile (11.4 g) and choroacetyl chloride (12.7 ml) in dichloromethane (170 ml) under ice-cooling and the mixture was stirred for 10 minutes at the same temperature. After the ice bath was removed, the mixture was stirred for 75 minutes.

The reaction mixture was added to a mixture of ice-water (300 ml) and dichloromethane (200 ml) and the separated dichloromethane layer was washed with water.

To this solution was added a water and the mixture was adjusted to pH 8 with 20% aqueous potassium carbonate.

The separated organic layer was washed with water and dried over magnesium sulfate. The solvent was removed by concentration to give [5-(chloroaceytl)furan-2-yl]acetonitrile (16.36 g).

IR (film): 3120, 2940, 2260, 2210, 1680, 1590, 1510 cm$^{-1}$.

NMR (DMSO-d$_6$, δ): 4.33 (2H, s), 4.83 (2H, s), 6.64 (1H, d, J=4 Hz), 7.55 (1H, d, J=4 Hz).

PREPARATION 2

A solution of methyl 3-(furan-2-yl)propanate (4.0 g) in 40% methylamine methanol solution (50 ml) was stirred for 5 hours at room temperature. The solvent was removed under reduced pressure to afford N-methyl-3-(furan-2-yl)propanamide (4.0 g).

IR (film): 3300, 3100, 2940, 1660, 1610 cm$^{-1}$.

NMR (CDCl$_3$, δ): 2.48 (2H, t, J=7.5 Hz), 2.76 (3H, d, J=5 Hz), 2.98 (2H, t, J=7.5 Hz), 5.72 (1H, br), 5.99 (1H, dd, J=3.8 and 0.5 Hz), 6.26 (1H, dd, J=2.0 and 3.8 Hz), 7.27 (1H, dd, J=2.0 and 0.5 Hz).

PREPARATION 3

A solution of methyl isocyanate (34.0 g) in methanol (30 ml) was added dropwise to a solution of furan-2-ylmethylamine (57.9 g) in methanol (300 ml) at 5° to 15° C. After being stirred at room temperature for three hours, the solvent was evaporated in vacuo. The residue was treated with diisopropyl ether (400 ml) to give N-(furan-2-ylmethyl)-N'-methylurea (81.9 g).

mp: 80° to 81° C.

IR (Nujol): 3350, 3320, 3150, 3125, 1610 cm$^{-1}$.

NMR (DMSO-d$_6$, δ): 2.60 (3H, d, J=5 Hz), 4.23 (2H, d, J=5 Hz), 5.85 (1H, q, J=5 Hz), 6.18 (1H, d, J=3 Hz), 6.35 (1H, dd, J=2 Hz and 3 Hz), 6.38 (1H, t, J=5 Hz), and 7.55 (1H, d, J=2 Hz).

PREPARATION 4

The following compound was obtained according to a similar manner to that of Example 19.

N-(Furan-2-ylmethyl)urea.

mp: 88°-92° C.

IR (Nujol): 3450, 3300, 3190, 1660, 1610, 1545 cm$^{-1}$.

NMR (DMSO-d$_6$, δ): 4.16 (2H, d, J=6 Hz), 5.55 (2H, s), 6.15–6.22 (1H, m), 6.32–6.42 (2H, m), 7.55 (1H, m).

PREPARATION 5

A mixture of N-(furan-2-ylmethyl)urea (83.0 g), acetic anhydride (580 ml) and phosphoric acid (10 ml) was stirred for 15 minutes at 80° C., and then the mixture was evaporated in vacuo. To the residue was added a mixture of ethyl acetate, tetrahydrofuran and water and the mixture was adjusted to pH 7.5 with potassium carbonate. The separated organic layer was washed with brine and the mixture was dried over magnesium sulfate. The solvent was removed by concentration and triturated with a mixture of ethyl acetate and ether. The precipitate was collected by filtration to give 1-acetyl-3-(5-acetylfuran-2-ylmethyl)urea (32.17 g).

IR (Nujol): 3310, 3230, 3110, 1670 cm$^{-1}$.

NMR (DMSO-d$_6$, δ): 2.02 (3H, s), 2.37 (3H, s), 4.45 (2H, d, J=6 Hz), 6.46 (1H, d, J=4 Hz), 7.39 (1H, d, J=4 Hz), 8.74 (1H, t, J=6 Hz).

The above filtrate was evaporated in vacuo. The residue was purified by column chromatography on silica gel eluting with a mixture of chloroform and methanol (39:1, V/V). The eluted fractions containing the desired product were collected and evaporated in vacuo to give 1-(5-acetylfuran-2-ylmethyl)-1,3-diacetylurea (21.3 g).

IR (Nujol): 1780, 1670 cm$^{-1}$.

NMR (DMSO-d$_6$, δ): 2.28 (3H, s), 2.38 (3H, s), 2.40 (3H, s), 5.01 (2H, s), 6.60 (1H, d, J=4 Hz), 7.41 (1H, d, J=4 Hz), 11.34 (1H, s).

PREPARATION 6

A solution of bromine (0.23 ml) in dichloromethane (5 ml) was dropwise added to a mixture of 1-acetyl-3-(5-acetylfuran-2-ylmethyl)urea (1.0 g) in dichloromethane (20 ml) at ambient temperature for 20 minutes and the mixture was stirred at the same temperature for 1.5 hours. The solvent was removed by concentration and residue was triturated with isopropyl ether to give 1-acetyl-3-[5-(bromoacetyl)furan-2-ylmethyl]urea (1.27 g).

mp: 128°-134° C. (dec.).

IR (Nujol): 3290, 3110, 1670, 1550 cm$^{-1}$.

NMR (DMSO-d$_6$, δ): 2.02 (3H, s), 4.47 (2H, d, J=6 Hz), 4.60 (2H, st, 6.53 (1H, d, J=4 Hz), 7.62 (1H, J=4 Hz), 8.77 (1H, t, J=6 Hz), 10.46 (1H, s).

PREPARATION 7

To a mixture of furan-2-ylacetonitrile (60.0 g) in dry isopropyl alcohol (600 ml) was babbled with dry hydrogen chloride for 5 hours under ice-cooling and the mixture was stirred for 2 hours at the same temperature. The solvent and excess hydrogen chloride was removed by concentration in vacuo. To the solution of resulting residue in dry isopropyl alcohol (400 ml) was bubbled with an ammonia gas for 1.5 hours under ice-cooling and the mixture was stirred for 1.5 hours at the same temperature. Evaporation of the solvent gave a residue, which was purified by column chromatography on aluminum eluting with a methanol. The eluted fractions containing the desired product were collected and evaporated in vacuo to give 2-(furan-2-yl)acetamidine hydrochloride (56.0 g).

IR (film): 3400–3000 (br), 1690, 1600, 1500 cm$^{-1}$.

NMR (DMSO-d$_6$, δ): 3.91 (2H, s), 6.42 (2H, s), 7.63 (1H, s), 9.08 (2H, br s), 9.38 (2H, br s).

PREPARATION 8

The mixture of 2-(furan-2-yl)acetamidine hydrochloride (30.0 g), methyl 2-acetylheptanoate (34.8 g) and sodium methoxide (10.1 g) in methanol (300 ml) was stirred for 4.5 hours at ambient temperature, and then the solvent was removed by concentration. To the residue was added a mixture of ethyl acetate and water, and the mixture was adjusted to pH 9 with 6N-hydrochloric acid. The separated organic layer was washed with brine and dried over magnesium sulfate. Evaporation of the solvent gave a residue, which was purified by column chromatography on silica gel eluting with a mixture of chloroform and methanol (19:1, V/V). The eluted fractions containing the desired product were collected and evaporated in vacuo to give 2-(furan-2-ylmethyl)-6-methyl-5-n-pentyl-4(1H)pyrimidinone (18.18 g).

mp: 99°-100° C.

IR (Nujol): 1660, 1610 cm$^{-1}$.

NMR (DMSO-d$_6$, δ): 0.86 (3H, t, J=6 Hz), 1.20-1.48 (6H, m), 2.17 (3H, s), 2.36 (2H, t, J=7 Hz), 3.86 (2H, s), 6.26 (1H, d, J=3 Hz), 6.39 (1H, m), 7.56 (1H, m), 12.37 (1H, s).

PREPARATION 9

The following compounds were obtained according to a similar manner to that of Preparation 1.

(1) Methyl N-[5-(chloroacetyl)furan-2-ylmethyl]carbamate.

mp: 86° to 91° C.

IR (Nujol): 3330, 1600 (br), 1510 cm$^{-1}$.

NMR (DMSO-d$_6$, δ): 3.59 (3H, s), 4.30 (2H, d, J=6 Hz), 4.85 (2H, s), 6.56 (1H, d, J=3 Hz), 7.59 (1H, d, J=3 Hz).

(2) N-Methyl-3-[5-(chloroacetyl)furan-2-yl]propanamide.

mp: 110° to 115° C.

IR (Nujol): 3300, 1640 cm$^{-1}$.

NMR (CDCl$_3$, δ): 2.79 (3H, d, J=4.7 Hz), 4.47 (2H, s), 5.75 (1H, br), 6.26 (1H, d, J=3.6 Hz), 7.23 (1H, d, J=3.6 Hz).

(3) N-[5-(Chloroacetyl)furan-2-ylmethyl]-N'-methylurea.

mp: 125° to 126° C.

IR (Nujol): 3370, 3330, 1680, 1635 cm$^{-1}$.

NMR (DMSO-d$_6$, δ): 2.55 (3H, d, J=4.5 Hz), 4.27 (2H, d, J=6 Hz), 4.84 (2H, s), 5.92 (1H, q, J=4.5 Hz), 6.45 (1H, d, J=3 Hz), 6.50 (1H, t, J=6 Hz) and 7.55 (1H, d, J=3 Hz).

(4) 2-[5(Chloroacetyl)furan-2-ylmethyl]-6-methyl-5-n-pentyl-4(1H)-pyrimidinone.

mp: 136°-139° C.

IR (Nujol): 1685, 1645, 1610 cm$^{-1}$.

NMR (DMSO-d$_6$, δ): 0.80-0.94 (3H, m), 1.15-1.50 (6H, m), 2.16 (3H, s), 2.27-2.42 (2H, m), 4.01 (2H, s), 4.85 (2H, s), 6.59 (1H, d, J=4 Hz), 7.59 (1H, d, J=4 Hz), 12.49 (1H, s).

(5) 2-Acetamidomethyl-5-chloroacetyl-3-methylfuran.

mp: 94°-100° C.

IR (Nujol): 3340, 1690, 1650, 1550, 1520 cm$^{-1}$.

NMR (DMSO-d$_6$, δ): 1.82 (3H, s), 2.04 (3H, s), 4.27 (2H, d, J=6 Hz), 4.80 (2H, s), 7.45 (1H, s), 8.43 (1H, t, J=6 Hz).

PREPARATION 10

The following compounds were obtained according to a similar manner to that of Example 1.

(1) 2-Amino-4-[5-(3-methylureidomethyl)furan-2yl]thiazole.

mp: 196° C.

IR (Nujol): 3400, 3300, 1610, 1575, 1515 cm$^{-1}$.

NMR (DMSO-d$_6$, δ): 2.56 (3H, d, J=5 Hz), 4.20 (2H, d, J=6 Hz), 5.83 (1H, q, J=5 Hz), 6.22 (1H, d, J=3 Hz), 6.34 (1H, t, J=6 Hz), 6.43 (1H, d, J=3 Hz), 6.63 (1H, s), 7.11 (4H, s).

(2) 2-Amino-4 -(5-cyanomethylfuran-2-yl)thiazole.

mp: 215°-216° C.

IR (Nujol): 3390, 3310, 3150, 2270, 1640, 1530 cm$^{-1}$.

NMR (DMSO-d$_6$, δ): 4.21 (2H, s), 6.43 (1H, d, J=3 Hz), 6.51 (1H, d, J=3 Hz), 6.73 (1Hz, s), 7.15 (2H, s).

PREPARATION 11

Benzoyl chloride (2.67 ml) was dropped to a refluxing solution of ammonium thiocyanate (1.92 g) in acetone (50 ml) and the mixture was refluxed for 15 minutes. 4-(5-Acetylaminomethylfuran-2-yl)-2-aminothiazole (5.20 g) was added portionwise to the refluxing mixture. After the mixture was refluxed for further two hours, the solvent was evaporated in vacuo and the residue was mixed with water and ethyl acetate. The resulting precipitate was collected by filtration and washed with ethyl acetate to afford 4-(5-acetylaminomethylfuran-2-yl)-2-(3-benzoylthioureido)-thiazole (5.50 g).

mp: 213° to 214° C.

IR (Nujol): 3270, 1675, 1630 cm$^{-1}$.

NMR (DMSO-d$_6$, δ): 1.90 (3H, s), 4.37 (2H, d, J=6 Hz), 6.40 (1H, d, J=3 Hz), 6.80 (1H, d, J=3 Hz), 7.42 (1H, s), 7.58-8.17 (5H, m), 8.40 (1H, d, J=6 Hz), 12.00 (1H, s) and 14.08 (1H, s).

PREPARATION 12

The following compounds were obtained according to a similar manner to that of Preparation 11.

(1) 2-(3-Benzoylthioureido)-4-(5-cyanomethylfuran-2-yl)thiazole.

mp: 207°-210° C. (dec.).

IR (Nujol): 3280, 2270, 1660, 1550, 1535 cm$^{-1}$.

NMR (DMSO-d$_6$, δ): 4.27 (2H, s), 6.52 (1H, d, J=3 Hz), 6.81 (1H, d, J=3 Hz), 7.40 (1H, s), 7.51-7.71 (3H, m), 8.00-8.04 (2H, m), 13.06 (1H, br s).

(2) 2-(3-Benzoylthioureido)-4-[5-(3-methylureidomethyl)furan-2-yl)thiazole.

mp: 213°-214° C.

IR (Nujol): 3340, 1675, 1630, 1590, 1545, 1520 cm$^{-1}$.

NMR (DMSO-d$_6$, δ): 2.58 (3H, d, J=5 Hz), 4.26 (2H, d, J=6 Hz), 5.89 (1H, q, J=5 Hz), 6.31 (1H, d, J=3 Hz), 6.44 (1H, t, J=6 Hz), 6.74 (1H, d, J=3 Hz), 7.37 (1H, s), 7.50-7.65 (2H, m), 7.65-7.78 (1H, m), 7.98-8.10 (2H, m).

PREPARATION 13

A solution of sodium hydroxide (0.55 g) in water (5 ml) was added to a suspension of 4-(5-acetylaminomethylfuran-2-yl)-2-(3-benzoylthioureido)thiazole (5.40 g) in methanol (50 ml) and the mixture was stirred at 60° C. for two hours. Following evaporation in vacuo, the residue was mixed with water (50 ml) and ethyl acetate (15 ml) and stirred for several minutes. The resulting precipitate was collected by filtration and washed with water and ethyl acetate to afford 4-(5-acetylaminomethylfuran-2-yl)-2-thioureidothiazole (2.95 g).

mp: 231° to 232° C.

IR (Nujol): 3310, 3270, 3190, 3140, 1635, 1620 cm$^{-1}$.

NMR (DMSO-d$_6$, δ): 1.86 (3H, s), 4.27 (2H, d, J=6 Hz), 6.30 (1H, d, J=3 Hz), 6.61 (1H, d, J=3 Hz), 7.10 (1H, s), 8.28 (1H, t, J=6 Hz), 8.33 (2H, br s) and 11.81 (1H, s).

PREPARATION 14

The following compounds were obtained according to a similar manner to that of Preparation 13.

(1) 4-(5-Cyanomethylfuran-2-yl)-2-thioureidothiazole.

mp: 216°-220° C.

IR (Nujol): 3290, 3180, 3130, 2250, 1620, 1560, 1520 cm$^{-1}$.

NMR (DMSO-d$_6$, δ): 4.25 (2H, s), 6.50 (1H, d, J=3 Hz), 6.72 (1H, d, J=3 Hz), 7.23 (1H, s), 8.10 (1H, br s), 8.74 (1H, br s), 11.84 (1H, s).

(2) 4-[5-(3-Methylureidomethyl)furan-2-yl]-2-thioureidothiazole.

mp: 229° C.

IR (Nujol): 3305, 1615, 1560 cm⁻¹.

NMR (DMSO-d₆, δ): 2.57 (3H, d, J=5 Hz), 4.22 (2H, d, J=6 Hz), 5.83 (1H, q, J=5 Hz), 6.28 (1H, d, J=3 Hz), 6.36 (1H, t, J=6 Hz), 6.63 (1H, d, J=3 Hz), 7.13 (1H, s).

PREPARATION 15

A mixture of 4-(5-acetylaminomethylfuran-2-yl)-2-(3-benzoylthioureido)thiazole (39.5 g) in ethanol (400 ml) and conc. hydrochloric acid (87.1 ml) was heated under reflux for 15 hours and then the mixture was evaporated in vacuo. To the residue was added to a mixture of ethyl acetate and water and the mixture was adjusted to pH 9.5 with a potassium carbonate. The isolated precipitate was collected by filtration to give 4-(5-aminomethylfuran-2-yl)-2-thioureidothiazole (10.1 g).

mp: 154°-158° C.

IR (Nujol): 3300, 3190, 3140, 1620, 1580, 1525 cm⁻¹.

NMR (DMSO-d₆, δ): 3.74 (2H, s), 6.31 (1H, d, J=3 Hz), 6.61 (1H, d, J=3 Hz), 7.11 (1H, s).

PREPARATION 16

A solution of potassium cyanate (9.6 g) in water (50 ml) was added to a mixture of 4-(5-aminomethylfuran-2-yl)-2-thioureidothiazole (10.0 g) in N,N-dimethylformamide (80 ml) and 1N-hydrochloric acid (78.6 ml), and the mixture was stirred for 16 hours at ambient temperature. To the reaction mixture was added a water (100 ml) and isolated precipitate was collected by filtration to give 2-thioureido-4-(5-ureidomethylfuran-2-yl)thiazole (10.74 g).

mp: 227°-229° C.

IR (Nujol): 3480, 3300, 1650, 1620, 1600, 1560, 1525 cm⁻¹.

NMR (DMSO-d₆, δ): 4.22 (2H, d, J=6 Hz), 5.58 (2H, s), 6.29 (1H, d, J=3 Hz), 6.41 (1H, t, J=6 Hz), 6.66 (1H, d, J=3 Hz), 7.13 (1H, s).

PREPARATION 17

A mixture of 4-(5-cyanomethylfuran-2-yl)-2-thioureidothiazole (11.4 g) and methyl iodide (2.7 ml) in methanol (110 ml) and tetrahydrofuran (60 ml) was refluxed for 1.5 hours under stirring. Evaporation of the solvent gave a residue, which was triturated with ethyl acetate to give 2-[(amino)(methylthio)methyleneamino]-4-(5-cyanomethylfuran-2-yl)thiazole hydriodide (14.50 g).

mp: 116°-118° C.

IR (Nujol): 3390, 3210, 2280, 1650, 1605, 1570 cm⁻¹.

NMR (DMSO-d₆, δ): 2.70 (3H, s), 4.30 (2H, s), 6.55 (1H, d, J=3 Hz), 7.01 (1H, d, J=3 Hz), 7.47 (1H, s).

PREPARATION 18

The following compounds were obtained according to a similar manner to that of Preparation 17.

(1) 2-[(Amino)(methylthio)methyleneamino]-4-[5-(3-methylureido)methylfuran-2-yl)thiazole hydriodide.

mp: 164°-167° C.

IR (Nujol): 3320, 3100, 1620, 1590, 1570 cm⁻¹.

NMR (DMSO-d₆, δ): 2.58 (3H, s), 2.64 (3H, s), 4.25 (2H, s), 6.32 (1H, d, J=3 Hz), 6.90 (1H, d, J=3 Hz), 7.33 (1H, s), 9.79 (1H, br s).

(2) 2-[(Amino)(methylthio)methyleneamino]-4-(5-ureidomethylfuran-2-yl)thiazole hydriodide.

mp: 161°-165° C.

IR (Nujol): 3430, 3180-3310 (br), 1625, 1570, 1530 cm⁻¹.

NMR (DMSO-d₆, δ): 2.61 (3H, s), 4.23 (2H, s), 6.33 (1H, d, J=3 Hz), 6.88 (1H, d, J=3 Hz), 7.32 (1H, s), 9.50-10.00 (1H, br s).

PREPARATION 19

A solution of (furan-2-yl)glyoxal (5.68 g), acetaldehyde (3.10 ml) and concentrated aqueous ammonia (30.9 ml) in ethanol (60 ml) was stirred for two hours at room temperature. The solvent was evaporated in vacuo and the residue was chromatographed on alumina by eluting with a mixture of chloroform and methanol (50:1, V/V) to give 4-(furan-2-yl)-2-methylimidazole (2.90 g).

mp: 109° to 114° C.

IR (Nujol): 3240, 1605 cm⁻¹.

NMR (DMSO-d₆, δ): 2.29 (3H, s), 6.44 (1H, dd, J=1 Hz and 3 Hz), 6.48 (1H, dd, J=2 Hz and 3 Hz), 7.18 (1H, s) and 7.56 (1H, dd, J=1 Hz and 2 Hz).

PREPARATION 20

The following compound was obtained according to a similar manner to that of Preparation 1.

4-[5-Chloroacetylfuran-2-yl]-2-methylimidazole.

mp: >300° C.

IR (Nujol): 1670 cm⁻¹.

NMR (DMSO-d₆, δ): 2.32 (3H, s), 4.85 (2H, s), 6.75 (1H, d, J=3.5 Hz), 7.58 (1H, s), 7.68 (1H, d, J=3.5 Hz) and 14.65 (1H, br s).

EXAMPLE 1

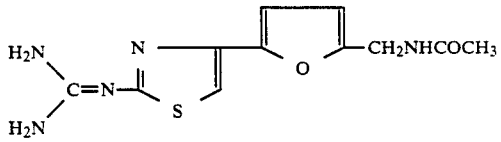

A solution of 5-acetylaminomethyl-2-chloroacetylfuran (39.9 g) and diaminomethylenethiourea (21.9 g) in ethanol (400 ml) was refluxed for two hours with stirring. The solvent was evaporated in vacuo and the residue was dissolved in water (300 ml). The solution was basified with an aqueous potassium carbonate. The resulting precipitate was collected by filtration, washed with water and recrystallized from a mixture of methanol, tetrahydrofuran and diisopropyl ether to afford 4-(5-acetylaminomethylfuran-2-yl)-2-(diaminomethyleneamino)thiazole (24.1 g).

mp: 230° to 231° C.

IR (Nujol): 3430, 3200, 3110, 3060, 1650 cm⁻¹.

NMR (DMSO-d₆, δ): 1.88 (3H, s), 4.26 (2H, d, J=6 Hz), 6.25 (1H, d, J=3 Hz), 6.56 (1H, d, J=3 Hz), 6.73 (1H, s), 6.83 (4H, s), 8.24 (1H, t, J=6 Hz).

Anal. Calcd. for $C_{11}H_{13}N_5O_2S$: C 47.20, H 4.69, N 25.07 Found: C 47.31, H 4.71, N 24.65.

EXAMPLE 2

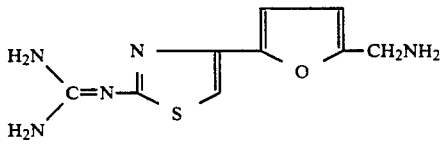

A solution of 4-(5-acetylaminomethylfuran-2-yl)-2-(diaminomethyleneamino)thiazole (4.76 g) in 1N-hydrochloric acid (51.1 ml) was refluxed for 8 hours with stirring. The solution was made basic to pH 10 with an aqueous potassium carbonate. The resulting precipitate was collected by filtration and washed with water to afford 4-(5-aminomethylfuran-2-yl)-2-(diaminomethyleneamino)thiazole (4.03 g).

mp: 160° to 163° C.

IR (Nujol): 3300 (broad), 1710, 1630 cm⁻¹.

NMR (DMSO-d₆, δ): 4.17 (2H, br s), 4.35 (2H, br s), 6.30 (1H, d, J=3 Hz), 6.62 (1H, d, J=3 Hz), 6.78 (1H, s), 7.00 (4H, br s).

EXAMPLE 3

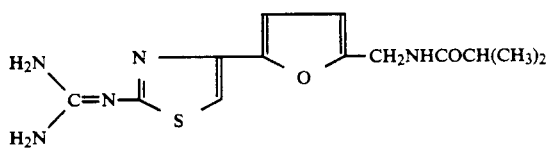

Isobutyryl chloride (0.4 ml) was added to a mixture of 4-(5-aminomethylfuran-2-yl)-2-(diaminomethyleneamino)thiazole (0.8 g) and triethylamine (1.3 ml) in dichloromethane (16 ml) under ice-cooling and the mixture was stirred for 2 hours at the same temperature. The solvent was removed by concentration in vacuo and the residue was dissolved in a mixture of tetrahydrofuran, ethyl acetate and water. The mixture was adjusted to pH 10 with 4N sodium hydroxide under solution of aqueous layer in sodium chloride.

The separated organic layer was washed with a brine and dried over magnesium sulfate. Evaporation of a solvent gave a residue, which was purified by column chromatography on silica gel eluting with a mixture of chloroform and methanol (9:1 to 4:1 V/V).

The eluted fraction containing the desired product were collected and evaporated to give 2-(diaminomethyleneamino)-4-(5-isobutyrylaminomethylfuran-2-yl)thiazole (0.14 g).

mp: 211°-213° C.

IR (Nujol): 3390, 3270, 3180, 1660, 1645, 1610, 1545 cm⁻¹.

NMR (DMSO-d₆, δ): 1.05 (6H, d, J=7 Hz), 2.15-2.61 (1H, m), 4.26 (2H, d, J=5 Hz), 6.22 (1H, d, J=3 Hz), 6.56 (1H, d, J=3 Hz), 6.72 (1H, s), 6.86 (4H, s), 8.15 (1H, t, J=5 Hz).

EXAMPLE 4

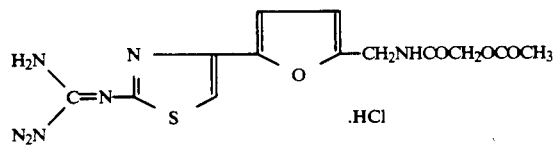

Acetoxyacetyl chloride (0.5 g) was added to a mixture of 4-(5-aminomethylfuran-2-yl)-2-(diaminomethyleneamino)thiazole (0.8 g) and triethylamine (1.3 ml) in dichloromethane (16 ml) under ice-cooling and the mixture was stirred for 20 hours at ambient temperature. Evaporation of the solvent gave a residue, which was purified by column chromatography on silica gel eluting with a mixture of chloroform and methanol (9:1 V/V).

The eluted fractions containing the desired product were collected and evaporated to give 4-(5-acetoxyacetylaminomethylfuran-2-yl)-2-(diaminomethyleneamino)thiazole hydrochloride (0.41 g).

mp: 250°-253° C. (dec.).

IR (Nujol): 3300, 1750, 1685, 1655, 1590 cm⁻¹.

NMR (DMSO-d₆, δ): 2.14 (3H, s), 4.36 (2H, d, J=5 Hz), 4.53 (2H, s), 6.35 (1H, d, J=3 Hz), 6.93 (1H, d, J=3 Hz), 7.27 (1H, s), 8.24 (4H, s), 8.56 (1H, t, J=5 Hz).

EXAMPLE 5

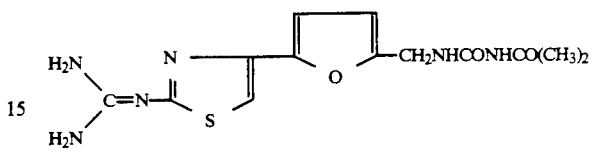

A mixture of 4-(5-aminomethylfuran-2-yl)-2-(diaminomethyleneamino)thiazole (0.8 g) and isopropylisocyanate (0.46 ml) in tetrahydrofuran (16 ml) and methanol (6.6 ml) was stirred for 8 hours at ambient temperature. Evaporation of a solvent gave a residue, which was purified by column chromatography on silica gel eluting with a mixture of chloroform and methanol (4:1, V/V).

The eluted fraction containing the desired product were collected and evaporated to give 2-(diaminomethyleneamino)-4-[5-(3-isopropylureido)methylfuran-2-yl]thiazole (0.41 g).

mp: 222°-224° C. (dec.).

IR (Nujol): 3440, 3320, 1665, 1615, 1585, 1570, 1550 cm⁻¹.

NMR (DMSO-d₆, δ): 1.06 (6H, d, J=7 Hz), 3.40-3.89 (1H, m), 4.20 (2H, d, J=5 Hz), 5.64 (1H, d, J=8 Hz), 6.08 (1H, t, J=5 Hz), 6.21 (1H, d, J=4 Hz), 6.56 (1H, d, J=4 Hz), 6.73 (1H, s), 6.86 (4H, s).

EXAMPLE 6

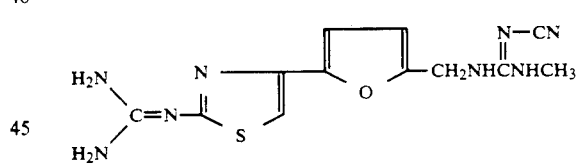

A solution of 4-(5-aminomethylfuran-2-yl)-2-(diaminomethyleneamino)thiazole (7.00 g) and dimethyl N-cyanodithioiminocarbonate (4.31 g) in N,N-dimethylformamide (70 ml) was stirred at 70° C. for two hours. 40% Aqueous methylamine by weight (14 ml) was added to the warmed solution and the mixture was stirred for an additional one hour at the same temperature. After the solvent was evaporated in vacuo, the residue was chromatographed on alumina, eluting with a mixture of chloroform and methanol (9:1, V/V), followed by recrystallization from a mixture of methanol, tetrahydrofuran and diisopropyl ether to afford 2-(diaminomethyleneamino)-4-[5-(2-cyano-3-methylguanidino)methylfuran-2-yl]thiazole (4.05 g).

mp: 231° to 232° C.

IR (Nujol): 3440, 3310, 3200, 2160, 1630 cm⁻¹.

NMR (DMSO-d₆, δ): 2.70 (3H, d, J=5 Hz), 4.32 (2H, d, J=6 Hz), 6.23 (1H, d, J=3 Hz), 6.53 (1H, d, J=3 Hz), 6.70 (1H, s), 6.81 (4H, s), 6.98 (1H, q, J=5 Hz), 7.35 (1H, t, J=6 Hz).

EXAMPLE 7

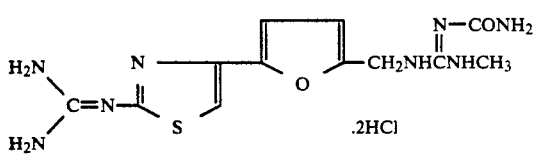

A mixture of 2-(diaminomethyleneamino)-4-[5-(2-cyano-3-methylguanidino)methylfuran-2-yl]thiazole (2.28 g) and 4M-dioxanic hydrogen chloride (10 ml) in methanol (20 ml) was stirred at ambient temperature for 19 hours and further at 50° C. for 5 hours. The resulting precipitate was collected by filtration, washed with methanol, and recrystallized from a mixture of methanol and water to afford 2-(diaminomethyleneamino)-4-[5-(2-carbamoyl-3-methylguanidino)methylfuran-2-yl]thiazole dihydrochloride (1.65 g).

mp: 241° to 242° C.

IR (Nujol): 3340–3100, 1715, 1685, 1665 cm$^{-1}$.

NMR (DMSO-d$_6$, δ): 2.93 (3H, d, J=5 Hz), 4.73 (2H, d, J=6 Hz), 6.60 (1H, d, J=3 Hz), 6.97 (1H, d J=3 Hz), 7.33 (1H, s), 7.60 (2H, br s), 8.30 (4H, s), 9.08 (2H, br s), 10.43 (1H, br s), 12.63 (1H, br s).

Anal. Calcd. for $C_{12}H_{16}N_8O_2S \cdot 2HCl$: C 35.21, H 4.43, N 27.38, Cl 17.22 Found: C 35.06, H 4.29, N 27.25, Cl 17.43.

EXAMPLE 8

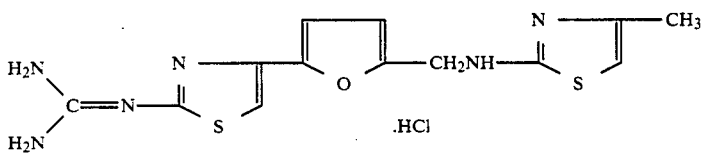

Benzoyl chloride (2.06 ml) was added dropwise to a refluxing suspension of ammonium isothiazonate (1.48 g) in acetone (40 ml). After the mixture was refluxed for 15 minutes, 4-(5-aminomethylfuran-2-yl)-2-(diaminomethyleneamino)thiazole (4.00 g) was added by portions and the mixture was refluxed further for 3.5 hours. The solvent was evaporated in vacuo and the residue was mixed with ethyl acetate (20 ml) and water (50 ml) and stirred for one hour. The resulting precipitate was collected, washed with water and then ethyl acetate, followed by drying under reduced pressure to afford 2-(diaminomethyleneamino)-4-[5-{3-(benzoyl)thioureido}methylfuran-2-yl]thiazole (3.31 g).

mp: 220° to 221° C. (dec.).

IR (Nujol): 3430–3120, 1720 (shoulder), 1670 cm$^{-1}$.

NMR (DMSO-d$_6$, δ): 4.90 (2H, d, J=5 Hz), 6.47 (1H, d, J=3 Hz), 6.72 (1H, d, J=3 Hz), 6.93 (1H, s), 7.23 (4H, s), 7.36–7.97 (5H, m), 11.19 (1H, t), J=5 Hz), 11.43 (1H, br s).

EXAMPLE 9

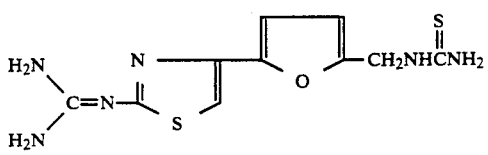

A suspension of 2-(diaminomethyleneamino)-4-[5-{3-(benzoyl)thioureido}methylfuran-2-yl]thiazole (3.20 g) and sodium hydroxide (0.32 g) in methanol (30 ml) was stirred at 60° C. for one hour. The reaction mixture was cooled in an ice bath and the resulting precipitate was collected by filtration and washed with methanol to afford 2-(diaminomethyleneamino)-4-(5-thioureidomethylfuran-2-yl)thiazole (1.73 g).

mp: 177° to 179° C.

IR (Nujol): 3370, 3180, 1650, 1630 cm$^{-1}$.

NMR (DMSO-d$_6$, δ): 4.56 (2H, d, J=5 Hz), 6.30 (1H, d, J=3 Hz), 6.59 (1H, d, J=3 Hz), 6.76 (1H, s), 6.84 (4H, s), 7.12 (2H, s), 7.93 (1H, t, J=5 Hz).

EXAMPLE 10

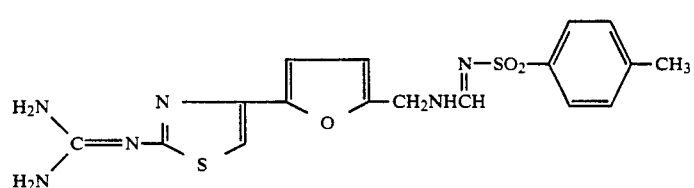

A suspension of 2-(diaminomethyleneamino)-4-(5-thioureidomethylfuran-2-yl)thiazole (0.70 g) and chloroacetone (0.22 g) in ethanol (15 ml) was refluxed for 4 hours with stirring. The solvent was evaporated in vacuo and the residue was recrystallized from a mixture of methanol and diisopropyl ether to afford 2-(diaminomethyleneamino)-4-[5-(4-methylthiazol-2-yl)aminomethylfuran-2-yl]thiazole (0.66 g).

mp: 193° to 194° C.

IR (Njuol): 3300, 3180, 3120, 1685 cm$^{-1}$.

NMR (DMSO-d$_6$, δ): 2.20 (3H, s), 4.52 (2H, s), 6.25 (1H, s), 6.47 (1H, d, J=3 Hz), 7.00 (1H, d, J=3 Hz), 7.30 (1H, s), 8.33 (4H, s).

Anal. Calcd. for $C_{13}H_{14}N_6OS_2 \cdot HCl$: C 42.10, H 4.08, N 22.66 Found: C 41.82, H 4.23, N 22.53.

EXAMPLE 11

A mixture of 4-(5-aminomethylfuran-2-yl)-2-(diaminomethyleneamino)thiazole (0.80 g) and ethyl tosylformimidate

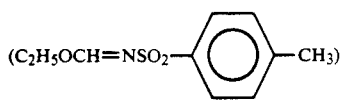

(0.77 g) in methanol (10 ml) was stirred for 5 hours at ambient temperature. The reaction mixture was diluted with diisopropyl ether (10 ml) and the resulting precipitate was collected by filtration. The product was purified by column chromatography on silica gel eluting with chloroform-methanol (9:1 V/V), followed by recrystallization from a mixture of methanol, tetrahydrofuran and diisoprpyl ether to afford 2-(diaminomethyleneamino)-4-(5-tosyliminomethylaminomethylfuran-2-yl)thiazole (0.46 g).

mp: 141° to 142° C.

IR (Nujol): 3370, 1620 (shoulder), 1605, 1330, 1145 cm$^{-1}$.

NMR (DMSO-d$_6$, δ): 2.39 (3H, s), 4.46 (2H, d, J=5 Hz), 6.33 (1H, d, J=3 Hz), 6.56 (1H, s), 6.58 (1H, d, J=3 Hz), 6.86 (4H, s), 7.28 (2H, d, J=8 Hz), 7.65 (2H, d, J=8 Hz), 8.14 (1H, d, J=5 Hz), 9.10-9.27 (1H, m).

Anal. Calcd. for C$_{17}$H$_{18}$N$_6$O$_3$S$_2$.H$_2$O: C46.78, H 4.82, N 19.25, H$_2$O 4.13 Found: C 46.86, H 4.59, N 18.78, H$_2$O 3.39.

EXAMPLE 12

The following compound was obtained according to a similar manner to that of Example 4.

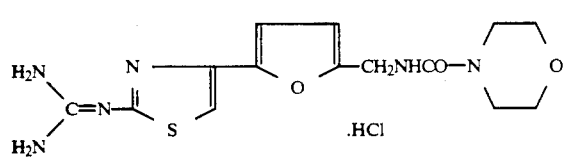

2-(Diaminomethyleneamino)-4-(5-morpholinocarbonylaminomethylfuran-2-yl)thiazole hydrochloride.

mp: 214°-215° C.

IR (Nujol): 3370, 3320, 3200, 1680, 1615, 1600 cm$^{-1}$.

NMR (DMSO-d$_6$, δ): 3.19-3.47 (4H, m), 3.47-3.76 (4H, m), 4.31 (2H, d, J=5 Hz), 6.33 (1H, d, J=3 Hz), 6.94 (1H, d, J=3 Hz), 7.12 (1H, t, J=5 Hz), 7.27 (1H, s), 8.21 (4H, s).

EXAMPLE 13

The following compound was obtained according to a similar manner to that of Example 6.

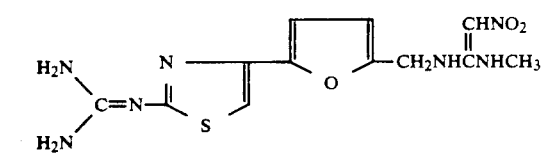

2-(Diaminomethyleneamino)-4-[5-{N-(1-methylamino-2-nitrovinyl)aminomethyl}furan-2-yl]thiazole.

mp: 238°-239° C.

IR (Nujol): 3350, 1610, 1550, 1380 cm$^{-1}$.

NMR (DMSO-d$_6$, δ): 2.85 (3H, d, J=4 Hz), 4.45 (2H, d, J=5 Hz), 6.38 (1H, d, J=3 Hz), 6.55 (1H, s), 6.61 (1H, d, J=3 Hz), 6.76 (1H, s), 6.84 (4H, s).

Anal. Calcd.: C 42.72, H 4.48, N 29.06 Found: C 42.77, H, 4.53, N 28.96.

EXAMPLE 14

The following compound was obtained according to a similar manner to that of Example 5.

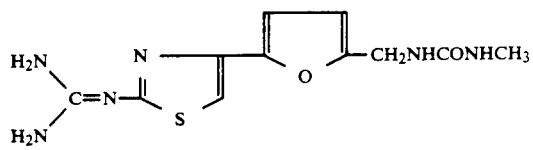

2-(diaminomethyleneamino)-4-[5-(3-methylureido)-methylfuran-2-yl]thiazole.

mp: 218°-219° C. (dec.).

IR (Nujol): 3400, 3330, 1630, 1590, 1540 cm$^{-1}$.

NMR (DMSO-d$_6$, δ): 2.54 (3H, d, J=5 Hz), 4.17 (2H, d, J=5 Hz), 5.56-5.85 (1H, m), 6.06-6.34 (1H, m), 6.17 (1H, d, J=3 Hz), 6.51 (1H, d, J=3 Hz), 6.68 (1H, s), 6.79 (4H, s).

EXAMPLE 15

The following compounds were obtained according to a similar manner to that of Example 3.

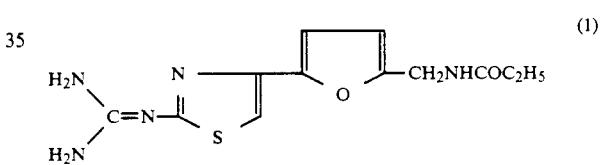

(1)

2-(Diaminomethyleneamino)-4-(5-propionylaminomethylfuran-2-yl)thiazole.

mp: 192°-194° C. (dec.).

IR (Nujol): 3380, 3290, 3110, 1660, 1615, 1540 cm$^{-1}$.

NMR (DMSO-d$_6$, δ): 1.06 (3H, t, J=7 Hz), 2.16 (2H, q, J=7 Hz), 4.28 (2H, d, J=5 Hz), 6.25 (1H, d, J=3 Hz), 6.58 (1H, d, J=3 Hz), 6.74 (1H, s), 6.86 (4H, s), 7.18 (1H, t, J=5 Hz).

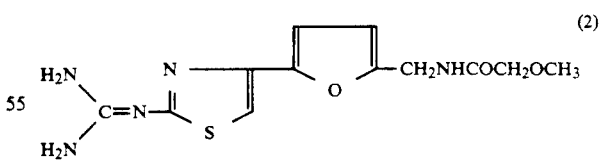

(2)

2-(Diaminomethyleneamino)-4-[5-(2-methoxyacetylaminomethyl)furan-2-yl]thiazole.

mp: 201°-202° C. (dec.).

IR (Nujol): 3430, 3370, 3110, 1670, 1640, 1600, 1555 cm$^{-1}$.

NMR (DMSO-d$_6$, δ): 3.33 (3H, s), 3.86 (2H, s), 4.33 (2H, d, J=5 Hz), 6.24 (1H, d, J=3 Hz), 6.56 (1H, d, J=3 Hz), 6.73 (1H, s), 6.86 (4H, s), 8.20 (1H, t, J=5 Hz).

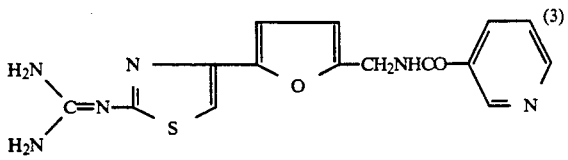

2-(Diaminomethyleneamino)-4-(5-nicotinoylaminomethylfuran-2-yl)thiazole.

mp: 224°–225° C.

IR (Nujol): 3480, 3400, 3350, 1610 cm$^{-1}$.

NMR (DMSO-d$_6$, δ): 4.51 (2H, d, J=5 Hz), 6.33 (1H, d, J=3 Hz), 6.57 (1H, d, J=3 Hz), 6.73 (1H, s), 6.82 (4H, s), 7.46 (1H, dd, J=4 and 8 Hz), 8.17 (1H, dt, J=2 and 8 Hz), 8.65 (1H, dd, J=2 and 4 Hz), 8.98 (1H, d, J=2 Hz), 9.13 (1H, t, J=5 Hz).

Anal. Calcd.: C 49.99, H 4.48, N 23.32 Found: C 50.00, H 4.50, N 23.39.

EXAMPLE 16

The following compounds were obtained according to a similar manner to that of Example 1.

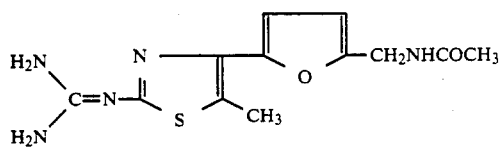

4-(5-Acetylaminomethylfuran-2-yl)-2-(diaminomethyleneamino)-5-methylthiazole.

mp: 247°–248° C.

IR (Nujol): 3420, 3350, 1660, 1605, 1550 cm$^{-1}$.

NMR (DMSO-d$_6$, δ): 1.85 (3H, s), 2.40 (3H, s), 4.24 (2H, d, J=5 Hz), 6.22 (1H, d, J=3 Hz) 6.44 (1H, d, J=3 Hz), 6.72 (4H, s), 8.20 (1H, t, J=5 Hz).

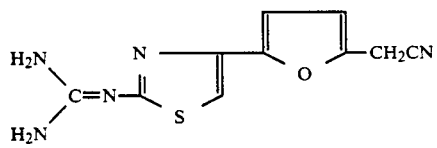

2-(Diaminomethyleneamino)-4-(5-cyanomethylfuran-2-yl)thiazole.

mp: 215°–218° C. (dec.).

IR (Nujol): 3450, 3420, 3370, 3110, 2250, 2210, 1650, 1610, 1590, 1510 cm$^{-1}$.

NMR (DMSO-d$_6$, δ): 4.20 (2H, s), 6.42 (1H, d, J=3 Hz), 6.65 (1H, d, J=3 Hz), 6.83 (1H, s), 6.87 (4H, s).

EXAMPLE 17

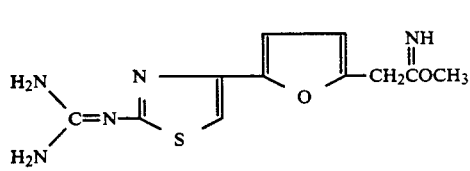

To a solution of 2-(diaminomethyleneamino)-4-(5-cyanomethylfuran-2-yl)thiazole (4.0 g) in dry chloroform (50 ml) and dry methanol (50 ml) was bubbled with dry hydrogen chloride for 100 minutes under ice-cooling and the mixture was stirred for 3.5 hours at the same temperature. The excess hydrogen chloride was removed by reduced pressure under stirring.

The resultant mixture was made basic to pH 9.5 with an aqueous potassium carbonate under ice-cooling. The mixture was extracted with the mixture of tetrahydrofuran and ethyl acetate. The extract layer was washed with a brine and dried over magnesium sulfate. Evaporation of the solvent gave a residue, which was triturated with ether to give 2-(diaminomethyleneamino)-4-[5-(2-imino-2-methoxyethyl)furan-2-yl]thiazole (4.28 g).

mp: 156°–162° C. (dec.).

IR (Nujol): 3420, 3110, 1655, 1610, 1590, 1550, 1510 cm$^{-1}$.

NMR (DMSO-d$_6$, δ): 3.60 (3H, s), 3.65 (2H, s), 6.26 (1H, d, J=3 Hz), 6.58 (1H, d, J=3 Hz), 6.73 (1H, s), 6.84 (4H, s), 7.81 (1H, s).

EXAMPLE 18

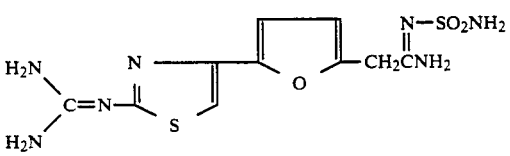

A mixture of 2-(diaminomethyleneamino)-4-[5-(2-imino-2-methoxyethyl)furan-2-yl]thiazole (4.2 g) and sulfamide (2.9 g) in methanol (100 ml) was heated under reflux for 3 hours. The solvent was removed by concentration in vacuo and to the residue was added a mixture of ethyl acetate and water. The mixture was adjusted to pH 1.0 with 6N-hydrochloric acid and the separated aqueous layer was adjusted to pH 10.0 with 20% aqueous potassium carbonate. The aqueous solution was extracted with a mixture of ethyl acetate and tetrahydrofuran under solution of aqueous layer in sodium chloride. The extract layer was washed with a brine and dried over magnesium sulfate.

Evaporation of the solvent gave a residue, which was purified by column chromatography on alumina eluting with the mixture of chloroform and methanol (9:1, V/V). The eluted fractions containing the desired product were evaporated to give 4-[5-[2-amino-2-(aminosulfonylimino)-ethyl]furan-2-yl]-2-(diaminomethyleneamino)thiazole (0.73 g).

mp: 222°–225° C. (dec.).

IR (Nujol): 3470, 3450, 3400, 3350, 3320, 3230, 1620, 1530 cm$^{-1}$.

NMR (DMSO-d$_6$, δ): 3.58 (2H, s), 6.28 (1H, d, J=3 Hz), 6.52 (2H, s), 6.56 (1H, d, J=3 Hz), 6.73 (1H, s), 6.81 (4H, s), 7.35 (1H, s), 8.18 (1H, s).

EXAMPLE 19

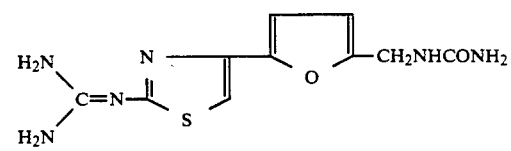

A solution of potassium cyanate (1.0 g) in water (9 ml) was dropwise added to a mixture of 4-(5-aminomethylfuran-2-yl)-2-diaminomethyleneamino)thiazole (1.5 g) in water (9 ml) and acetic acid (4.5 ml) at 35° C. for 2 minutes and the mixture was stirred at the same temperature for 2 hours. To the reaction mixture was added a mixture of ethyl acetate, tetrahydrofuran and water and the resultant mixture was adjusted to pH 9.0 with 20% aqueous potassium carbonate. The separated organic layer was washed with a brine and dried over magnesium sulfate. Evaporation of the solvent gave a residue, which was purified by column chromatography on silica gel eluting with a mixture of ethyl acetate and methanol (85:15, V/V). The eluted fractions containing the desired product were collected and evaporated in vacuo. The residue was recrystallized from a aqueous N,N-dimethylformamide to give 2-(diaminomethyleneamino)-4-(5-ureidomethylfuran-2-yl)thiazole (0.31 g).

mp: 214°-215° C.

IR (Nujol): 3400, 3320, 3130, 1650, 1590 cm$^{-1}$.

NMR (DMSO-d$_6$, δ): 4.19 (2H, d, J=5 Hz), 5.53 (2H, s), 6.24 (1H, d, J=3 Hz), 6.36 (1H, t, J=5 Hz), 6.59 (1H, d, J=3 Hz), 6.76 (1H, s), 6.87 (4H, s).

Anal. Calcd. for C$_{10}$H$_{12}$N$_6$O$_2$S.1/3 H$_2$O: C 41.95 H 4.46, N 29.35, H$_2$O 2.10 Found: C 42.04, H 4.53, N 29.04 H$_2$O 2.33.

EXAMPLE 20

The following compounds were obtained according to a similar manner to that of Example 1.

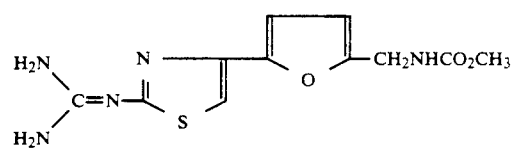
(1)

2-(Diaminomethyleneamino)-4-(5-methoxycarbonylaminomethylfuran-2-yl)thiazole mp: 196° C.

IR (Nujol): 3450, 3400, 1710, 1650, 1610 cm$^{-1}$.

NMR (DMSO-d$_6$, δ): 3.57 (3H, s), 4.19 (2H, d, J=5 Hz), 6.26 (1H, d, J=3 Hz), 6.58 (1H, d, J=3 Hz), 6.75 (1H, s), 6.85 (4H, s), 7.58 (1H, br s),

Anal. Calcd. for C$_{11}$H$_{13}$N$_5$O$_3$S: C 44.74, H 4.44, N 23.71 Found: C 44.71, H 4.63, N 23.83.

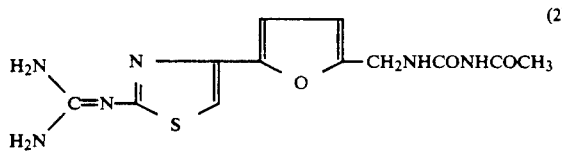
(2)

4-[5-(3-Acetylureidomethyl)furan-2-yl]-2-(diaminomethyleamino)thiazole.

mp: 245° C. (dec.).

IR (Nujol): 34,00, 3300, 1680, 1650, 1540 cm$^{-1}$.

NMR (DMSO-d$_6$, δ): 2.02 ( 3H, s), 4.41 (2H, d, J=6 Hz), 6.31 (1H, d, J=3 Hz), 6.62 (1H, d, J=3 Hz), 6.78 (1H, s), 6.90 (4H, s), 8.68 (1H, t, J=6 Hz), 10.43 (1H, s).

Anal. Calcd. for C$_{12}$H$_{14}$N$_6$O$_3$S: C 44.71, H 4.38, N 26.07 Found: C 44.53, H, 4.24, N 26.24.

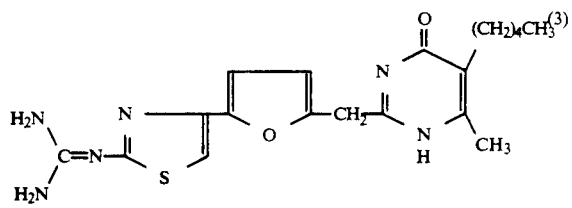
(3)

2-(Diaminomethyleneamino)-4-[5-(6-methyl-5-pentyl-4(1H)-pyrimidinon-2-ylmethyl)furan-2-yl]thiazole.

mp: 212°-213° C.

IR (Nujol): [3450, 1640, 1605, 1540 cm$^{-1}$. NMR (DMSO-d$_6$, δ): 0.75–0.95 (3H, m), 1.20–1.50 (6H, m), 2.18 (3H, s), 2.28–2.48 (2H, m), 3.90 (2H, s), 6.31 (1H, d, J=3 Hz), 6.61 (1H, d, J=3 Hz), 6.76 (1H, s), 6.90 (1H, s), 12.40 (1H, s).

Anal. Calcd. for C$_{19}$H$_{24}$N$_6$O$_2$S: C 56.98, H 6.04, N 20.98 Found: C 56.72, H 5.95, N 20.76.

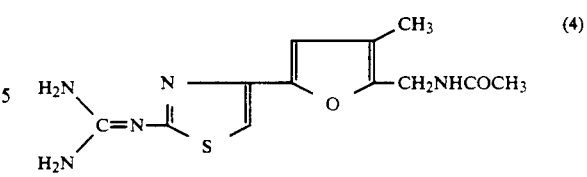
(4)

4-(5-Acetylaminomethyl-4-methylfuran-2-yl)-2-(diaminomethyleamino)thiazole.

mp: 237° C.

IR (Nujol): 3400, 3280, 3140, 3070, 1640, 1600, 1540 cm$^{-1}$.

NMR (DMSO-d$_6$, δ): 1.82 (3H, s), 1.99 (3H, s), 4.22 (2H, d, J=5 Hz), 6.51 (1H, s), 6.72 (1H, s), 6.88 (4H, s), 8.25 (1H, t, J=5 Hz).

Anal. Calcd. for C$_{12}$H$_{15}$N$_5$O$_2$S: C 49.13, H 5.15, N 23.87 Found: C 49.48, H 5.15, N 23.93.

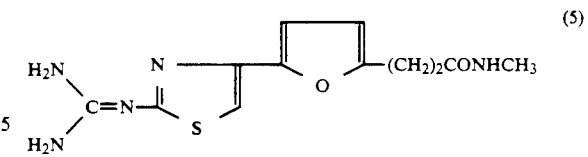
(5)

2-(Diaminomethyleneamino)-4-[5-{2-(methylcarbamoyl)ethyl}furan-2-yl]thiazole.

mp: 229° to 230° C.

IR (Nujol): 3400, 3340, 1640, 1610 cm$^{-1}$.

NMR (DMSO-d$_6$, δ): 2.42 (2H, t, J=7.5 Hz), 2.59 (3H, d, J=4.5 Hz), 2.88 (2H, t, J=7.5 Hz), 6.11 (1H, d, J=3.0 Hz), 6.52 (1H, d, J=3.0 Hz), 6.70 (1H, s), 6.85 (4H, s), 7.79 (1H, d, J=4.5 Hz).

Anal. Calcd for C$_{12}$H$_{15}$N$_5$O$_2$S: C 49.13, H 5.15, N 23.87 Found: C 49.08, H 5.32, N 23.67.

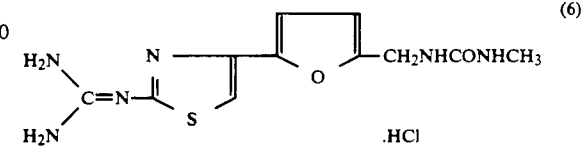
(6)

2-(Diaminomethyleneamino)-4-[5-(3-methylureido)-methylfuran-2-yl]thiazole hydrochloride.

mp: 220° to 221° C. (dec.).

IR (Nujol): 3280, 3140, 1685 cm⁻¹.

NMR (DMSO-d₆, δ): 2.63 (3H, s), 4.30 (2H, d, J=5 Hz), 6.00 (1H, br s), 6.32 (1H, d, J=3 Hz), 6.45 (1H, t, J=5 Hz), 6.80 (1H, d, J=3 Hz), 7.07 (1H, s), 8.00 (4H, s) and 12.67 (1H, br s).

EXAMPLE 21

The following compounds were obtained from 4-(5-aminomethylfuran-2-yl)-2-(diaminomethyleneamino)thiazole according to a similar manner to that of Example 3.

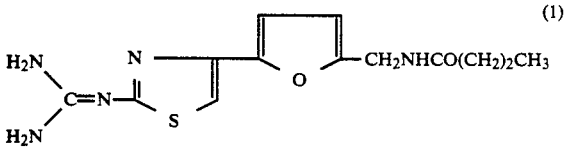

4¹-(5-Butyrylaminomethylfuran-2-yl)-2-(diaminomethyleneamino)thiazole.
mp: 182° to 183° C.,
IR (Nujol): 3520, 1610 cm⁻¹.

NMR (DMSO-d₆, δ): 0.85 (3H, T, J=7.0 Hz), 1.75–1.28 (2H, m), 2.09 (2H, t, J=7 Hz), 4.25 (2H, d, J=5.0 Hz), 6.24 (1H, d, J=3.3 Hz), 6.55 (1H, d, J=3.3 Hz), 6.72 (1H, s), 6.83 (4H, s), 8.21 (1H, t, J=5.0 Hz).

Anal. Calcd. for C₁₃H₁₇N₅O₂S·H₂O: C 47.99, H 5.86, N 21.52 Found: C 48.26, H 5.97, N 21.70.

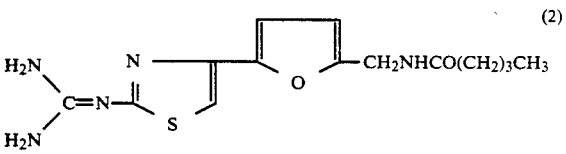

2-(Diaminomethyleneamino)-4-(5-valerylaminomethylfuran-2-yl)thiazole.
mp 197° C.
IR (Nujol): 3390, 3290, 1650, 1610 cm⁻¹.

NMR (DMSO-d₆, δ): 0.80 (3H, t, J=6.3 Hz), 1.68–1.00 (4H, m), 2.08 (2H, t, J=6.9 Hz), 4.21 (2H, d, J=5.7 Hz), 6.18 (1H, d, J=3.0 Hz), 6.51 (1H, d, J=3.0 Hz), 6.65 (1H, s, 6.79 (4H, s), 8.17 (1H, t, J=5.7 Hz).

Anal. Calcd. for C₁₄H₁₉N₅O₂S: C 52.30, H 5.96, N 21.79 Found: C 52.90, H 6.05, N 22.01.

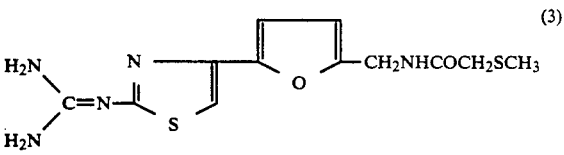

2-(Diaminomethyleneamino)-4-(5-methylthioacetylaminoethylfuran-2-yl)thiazole.
mp: 195°–197° C. (dec.).
IR (Nujol): 3440, 3250, 1620, 1595, 1540 cm⁻¹. NMR (DMSO-d₆, δ): 2.10 (3H, s), 3.10 (2H, s), 4.27 (2H, d, J=5 Hz), 6.25 (1H, d, J=3 Hz), 6.55 (1H, d, J=3 Hz), 6.70 (1H, s), 6.81 (4H, s), 8.37 (1H, t, J=5 Hz).

Anal. Calcd. for C₁₂H₁₅N₅O₂S: C 44.29, H 4.65, N 21.52 Found: C 44.17, H 5.09, N 21.14.

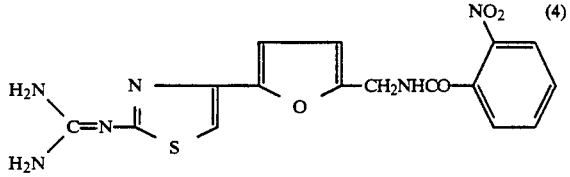

2-(Diaminomethyleneamino)-4-[5-(2-nitrobenzoyl)aminomethylfuran-2-yl]thiazole.
mp: 218° to 220° C.
IR (Nujol): 3420, 3350, 1650, 1610 cm⁻¹.

NMR (DMSO-d₆, δ): 4.43 (2H, d, J=5.4 Hz), 6.32 (1H, d, J=3.0 Hz), 6.55 (1H, d, J=3.0 Hz), 6.70 (1H, s), 6.78 (4H, s), 7.99–7.48 (3H, m), 7.97 (1H, dd, J=6.6 and 1.8 Hz), 9.09 (1H, t, J=5.4 Hz).

Anal. Calcd. for C₁₆H₁₄N₆O₄S: C 49.74, H 3.65, N 21.75 Found: C 49.37, H 3.76, N 21.57.

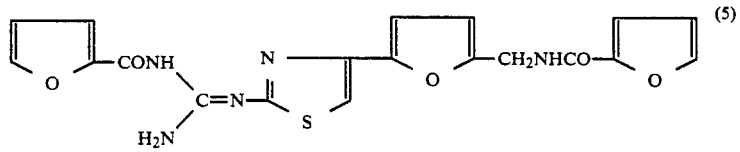

2-[(Amino)(2-furoylamino)methyleneamino]-4-[5-(2-furoyl)aminomethylfuran-2-yl]thiazole. mp: 199° to 200° C.
IR (Nujol): 3450, 3375, 1660, 1630 cm⁻¹.

NMR (DMSO-d₆, δ): 4.47 (2H, d, J=5.3 Hz), 6.36 (1H, d, J=3.2 Hz), 6.65–6.55 (2H, m), 6.71 (1H, d, J=3.2 Hz), 7.12 (1H, s), 7.20–7.05 (1H, m), 7.52 (1H, br), 7.81 (1H, t, J=0.7 Hz), 7.94 (1H, s), 8.82 (2H, m).

Anal. Calcd. for C₁₉H₁₅N₅O₅S: C 53.64, H 3.55, N 16.46 Found: C 53.95, H 3.64, N 16.35.

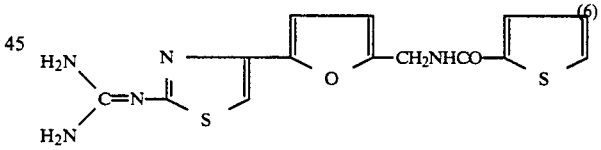

2-(Diaminomethyleneamino)-4-[5-(2-thenoyl)aminomethylfuran-2-yl]thiazole.
mp: 217° to 220° C.
IR (Nujol): 3400, 1610 cm⁻¹.

NMR (DMSO-d₆, δ): 4.41 (2H, d, J=5.4 Hz), 6.26 (1H, d, J=3.0 Hz), 6.53 (1H, d, J=3.0 Hz), 6.69 (1H, s), 6.78 (4H, s), 7.07 (1H, t, J=4.5 Hz), 7.80–7.64 (2H, m), 8.92 (1H, t, J=5.4 Hz).

Anal. Calcd. for C₁₄H₁₃N₅O₂S₂: C 48.40, H 3.77, N 20.16 Found: C 47.98, H 4.13, N 20.22.

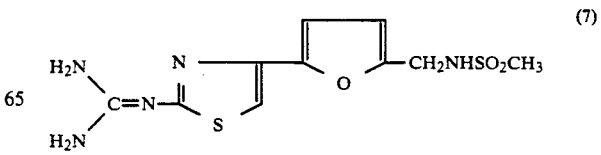

2-(Diaminomethyleneamino)-4-(5-mesylaminome-thylfuran-2-yl)thiazole.

mp: 198° C.

IR (Nujol): 3420, 3270, 1650, 1305, 1145 cm$^{-1}$.

NMR (DMSO-d$_6$, δ): 2.91 (3H, s), 4.19 (2H, d, J=5.5 Hz), 6.37 (1H, d, J=3.5 Hz), 6.60 (1H, d, J=3.5 Hz), 6.78 (1H, s), 6.85 (4H, s), 7.54 (1H, t, J=5.5 Hz).

IR (Nujol): 3400, 3330, 3130, 1625, 1595, 1545 cm$^{-1}$.

NMR (DMSO-d$_6$, δ): 0.83 (3H, t, J=7 Hz), 1.06–1.64 (2H, m), 3.91–3.12 (2H, m), 4.21 (2H, d, J=5 Hz) 5.91 [1H, t, J=5Hz), 6.07–6.34 (1H, m), 6.22](1H, d, J=3 Hz), 6.58 (1H, d, J=3 Hz), 6.75 (1H, s), 6.86 (4H, s).

Anal. Calcd. for C$_{13}$H$_{18}$N$_6$O$_2$S: C 48.43, H 5.63, N 26.07 Found: C 48.03, H 5.53, N 25.90.

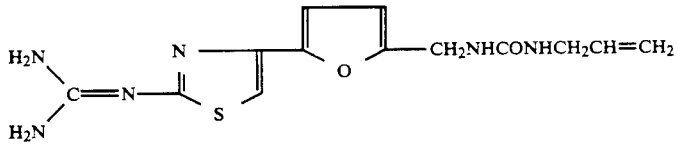
(3)

Anal. Calcd. for C$_{10}$H$_{13}$N$_5$O$_3$S$_2$: C 38.08, H 4.16, N 22.21 Found: C 37.54, H 4.12, N 21.53.

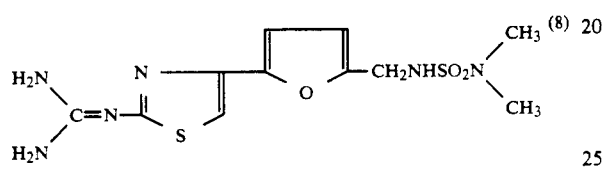
(8)

2-(Diaminomethyleneamino)-4-[5-(N,N-dime-thylamino)sulfonylaminomethylfuran-2yl]thiazole.

mp: 169° C.

IR (Nujol): 3400, 1605, 1520, 1140 cm$^{-1}$.

NMR (DMSO-d$_6$, δ): 2.64 (6H, s), 4.13 (2H, d, J=5.8 Hz), 6.37 (1H, d, J=3.2 Hz), 6.62 (1H, d, J=3.2 Hz), 6.79 (1H, s), 6.89 (4H, s), 7.70 (1H, t, J=5.8 Hz).

Anal. Calcd. for C$_{11}$H$_{16}$N$_6$O$_3$S$_2$: C 38.36, H 4.68, N 24.40 Found: C 37.97, H 4.36, N 24.31.

EXAMPLE 22

The following compounds were obtained according to a similar manner to that of Example 5.

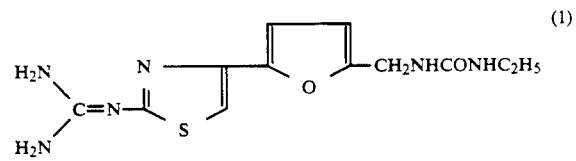
(1)

2-(Diaminomethyleneamino)-4-[5-(3l-ethylureido)-methylfuran-2-yl]thiazole.

mp: 221°–223° C. (dec.).

IR (Nujol): 3380, 3300, 1640, 1610, 1540 cm$^{-1}$. NMR (DMSO-d$_6$, δ): 1.00 (3H, t, J=7 Hz), 2.82–3.20 (2H, m), 4.18 (2H, d, J=6 Hz), 5.84 (1H, t, J=6 Hz), 6.02–6.33 (1H, m), 6.19 (1H, d, J=3 Hz), 6.53 (1H, d, J=3 Hz), 6.70 (1H, s) 6.82 (4H, s).

Anal. Calcd. for C$_{12}$H$_{16}$N$_6$O$_2$S: C 46.74, H 5.23, N 27.25 Found: C 46.96, H 5.50, N 27.33.

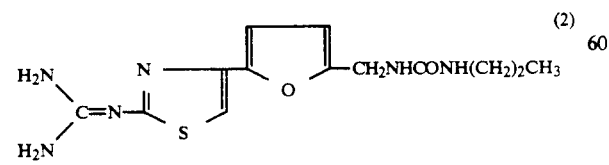
(2)

2-(Diaminomethyleneamino)-4-[5-(3-n-propylureido)methylfuran-2-yl]thiazole.

mp: 223° C.

4-[5-(3-Allylureido)methylfuran-2-yl]-2-(diaminome-thyleneamino)thiazole.

mp: 219°–220° C. (dec.).

IR (Nujol): 3440, 3400, 3325, 1620, 1590 cm$^{-1}$.

NMR (DMSO-d$_6$, δ): 3.55–3.90 (2H, m), 4.27 (2H, d, J=6 Hz), 4.90–5.40 (2H, m), 5.57–6.10 (1H, m), 5.90–6.55 (2H, m), 6.28 (1H, d, J=3 Hz), 6.61 (1H, d, J=3 Hz), 6.78 (1H, s), 6.91 (4H, s).

Anal. Calcd. for C$_{13}$H$_{16}$N$_6$O$_2$S: C 48.74, H 5.03, N 26.23 Found: C 48.51, H 5.30, N 25.99.

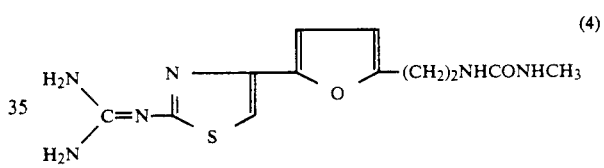
(4)

2-(Diaminomethyleneamino)-4-[5-{2-(3-methylureido)-ethyl}furan-2-yl]thiazole.

mp: 224°–225° C.

IR (Nujol): 3440, 3320, 1660, 1630, 1590, 1540 cm$^{-1}$.

NMR (DSMO-d$_6$, δ): 2.52 (3H, d, J=5 Hz), 2.70 (2H, t, J=7 Hz), 3.05–3.38 (2H, m), 5.57–5.98 (2H, m), 6.13 (1H, d, J=3 Hz), 6.51 (1H, d, J=3 Hz), 6.70 (1H, s), 6.80 (4H, m).

Anal. Calcd. for C$_{12}$H$_{16}$N$_6$O$_2$S C 46.74, H 5.23, N 27.25 Found: C 46.50, H 4.82, N 27.03.

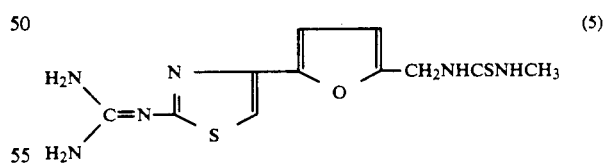
(5)

2-(Diaminomethyleneamino)-4-[5-(3-methylthi-oureido)-methylfuran-2-yl]thiazole.

mp: 220° C.

IR (Nujol): 3400, 3340, 1610 cm$^{-1}$.

NMR (DMSO-d$_6$, δ): 2.85 (3H, d, J=3.5 Hz), 4.64 (2H, d, J=4.5 Hz), 6.33 (1H, d, J=3.0 Hz), 6.61 (1H, d, J=3.0 Hz), 6.78 (1H, s), 6.89 (4H, s), 7.50 (1H, br), 7.85 (1H, t, J=4.5 Hz).

EXAMPLE 23

The following compounds were obtained according to a similar manner to that of Example 6.

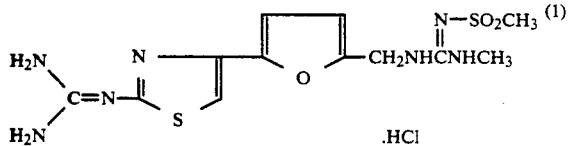

2-(Diaminomethyleneamino)-4-[5-(2-mesyl-3-methyl-guanidino)methylfuran-2-yl]thiazole hydrochloride.

mp: 233° to 234° C.

IR (Nujol): 3350, 3230, 1675, 1370, 1100 cm$^{-1}$.

NMR (DMSO-d$_6$, δ): 2.76 (3H, d, J=5 Hz), 2.80 (3H, s), 4.42 (2H, d, J=6 Hz), 6.40 (1H, d, J=3 Hz), 6.96 (1H, d, J=3 Hz), 7.12 (1H, q, J=5 Hz), 7.32 (1H, s), 7.45 (1H, t, J=6 Hz) and 8.34 (4H, s).

Anal. Calcd. for C$_{12}$H$_{17}$N$_7$O$_3$S$_2$·HCl: C 35.34, H 4.45, N 24.04, Cl 8.69 found: C 35.11, H 4.59, N 23.88, Cl 8.83.

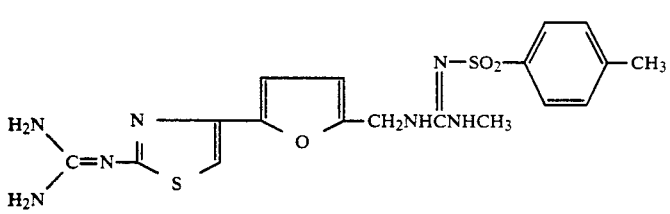

2-(Diaminomethyleneamino)-4-[5-(3-methyl-2-tosyl-quanidino)methylfuran-2-yl]thiazole.

mp: 208° to 209° C.

IR (Nujol): 3420, 3380, 3330, 1650, 1375, 1125 cm$^{-1}$.

NMR (DMSO-d$_6$, δ): 2.31 (3H, s), 2.71 (3H, d, J=4.5 Hz), 4.38 (2H, d, J=5.5 Hz), 6.18 (1H, d, J=3 Hz), 6.58 (1H, d, J=3 Hz), 6.67 (1H, s), 6.90 (4H, br s), 7.21 (2H, d, J=8 Hz), 7.23 (1H, t, J=4.5 Hz), 7.54 (1H, t, J=5.5 Hz) and 7.61 (2H, d, J=8 Hz).

Anal. Calcd. for C$_{18}$H$_{21}$N$_7$O$_3$S$_2$: C 48.31, H 4.73, N 21.91 Found: C 48.21, H 5.00, N 21.66.

EXAMPLE 24

The following compounds were obtained according to a similar manner to that of Example 11.

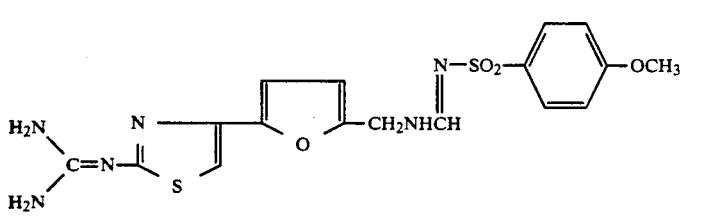

2-(Diaminomethyleneamino)-4-[5-(p-methoxyphenyl-sulfonyl)iminomethylaminomethylfuran-2yl]thiazole mp: 185° to 186° C.

IR (Nujol): 3370, 1620, 1330, 1145 cm$^{-1}$.

NMR (DMSO-d$_6$, δ): 3.85 (3H, s), 4.50 (2H, d, J=5 Hz), 6.38 (1H, d, J=3 Hz), 6.63 (1H, s), 6.65 (1H, d, J=3 Hz), 6.97 (4H, s), 7.08 (2H, d, J=9 Hz), 7.76 (2H, d, J=9 Hz), 8.21 (1H, d, J=5 Hz) and 9.08-9.38 (1H, m).

Anal. Calcd. for C$_{17}$H$_{18}$N$_6$O$_4$S$_2$·H$_2$O: C 45.12, H 4.45, N 18.57, H$_2$O 3.98 Found: C 45.25, H 4.81, N 18.07, H$_2$O 2.56.

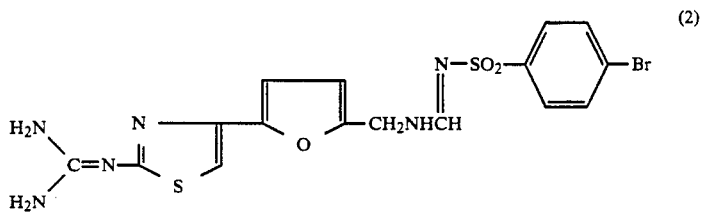

2-(Diaminomthyleneamino)-4-[5-(p-bromophenylsul-fonyl)iminomethylaminomethylfuran-2-yl]thiazole mp: 210° to 211° C.

IR (Nujol): 3520, 3400, 1610, 1330, 1140 cm$^{-1}$.

NMR (DMSO-d$_6$, δ): 4.55 (2H, d, J=5 Hz), 6.42 (1H, d, J=3 Hz), 6.65 (1H, s), 6.68 (1H, d, J=3 Hz), 6.97 (4H, s), 7.75 (4H, s), 8.25 (1H, d, J=4 Hz) and 9.35-9.67 (1H, m).

Anal. Calcd. for C$_{16}$H$_{15}$BrN$_6$O$_3$S$_2$: C 39.76, H 3.13, N 17.39 Found: C 40.17, H 3.41, N 17.12.

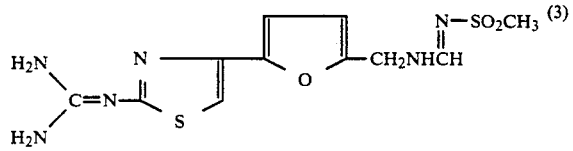

2-(Diaminomethyleneamino)-4-(5-mesyliminome-thylaminomethylfuran-2-yl)thiazole.

mp: 222° to 223° C. (dec.).

IR (Nujol): 3440, 3360, 3290, 1600, 1320, 1120 cm$^{-1}$.

NMR (DMSO-d$_6$, δ): 2.90 (3H, s), 4.48 (2H, d, J=5.4 Hz), 6.41 (1H, d, J=3.0 Hz), 6.62 (1H, d, J=3.0 Hz), 6.80 (1H, s), 6.85 (4H, s), 8.03 (1H, d, J=4.5 Hz) and 9.09 (1H, br s).

Anal. Calcd. for $C_{11}H_{14}N_6O_3S_2$: C 38.59, H 4.12, N 24.54 Found: C 38.66, H 4.24, N 24.85.

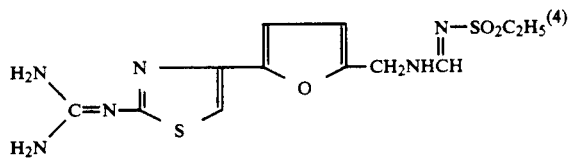
(4)

2-(Diaminomethyleneamino)-4-(5-ethylsulfonyliminomethylaminomethylfuran-2-yl)thiazole.
mp: 188° C.
IR (Nujol): 3460, 3400, 3350, 1630, 1320, 1130 cm$^{-1}$.
NMR (DMSO-d$_6$, δ): 1.13 (2.64 H, t, J=7.5 Hz), 1.14 (0.36H, t, J=7.5 Hz), 2.96 (2H, q, J=7.5 Hz), 4.48 (1.76H, d, J=5.0 Hz), 4.54 (0.24 H, d, J=5.5 Hz), 6.42 (1H, d, J=3.0 Hz), 6.65 (1H, d, J=3.0 Hz), 6.78 (0.12H, s), 6.80 (0.88H, s), 6.89 (4H, s), 8.00 (0.88H, d, J=4.5 Hz), 8.18 (0.12H, d, J=13.0 Hz), 9.14 (0.88H, dd, J=5.0 and 4.5 Hz), 9.4-9.2 (0.12H, br).
Anal. Calcd. for $C_{12}H_{16}N_6O_3S_2$: C 40.44, H 4.52, N 23.58 Found: C 40.49, H 4.53, N 23.46.

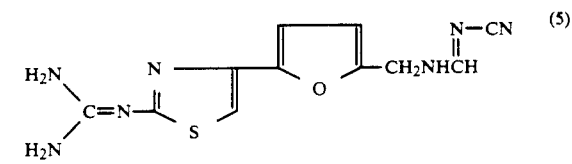
(5)

4-(5-Cyanoiminomethylaminomethylfuran-2-yl)-2-(diaminomethyleneamino)thiazole.
mp: 193° to 194° C.
IR (Nujol): 3400, 3190, 2170, 1630 cm$^{-1}$.
NMR (DMSO-d$_6$, δ): 4.52 (2H, s), 6.59 (1H, d, J=3 Hz), 6.68 (1H, d, J=3 Hz), 6.83 (1H, s), 6.92 (4H, s), 8.42 (1H, s) and 9.50 (1H, br s).
Anal. Calcd. for $C_{11}H_{11}N_7OS$: C 45.67, H 3.83 N 33.89 Found: C 45.61, H 4.53, N 33.49.

(6)

4-[5-(1-Cyanoiminoethyl)aminomethylfuran-2-yl)-2-(diaminomethyleneamino)thiazole
mp: 215° to 217° C.
IR (Nujol): 3320, 3180, 2180, 1600, 1570, 1530 cm$^{-1}$.
NMR (DMSO-d$_6$, δ): 2.25 (3H, s), 4.42 (2H, d, J=4 Hz), 6.43 (1H, s), 6.64 (1H, s), 6.81 (1H, s), 6.90 (4H, s), 9.28 (1H, s).
Anal. Calcd. for $C_{12}H_{13}N_7OS$: C 47.53, H 4.32, N 32.32 Found: C 47.48, H 4.33, N 31.95.

EXAMPLE 25

The following compounds were obtained according to a similar manner to that of Example 18.

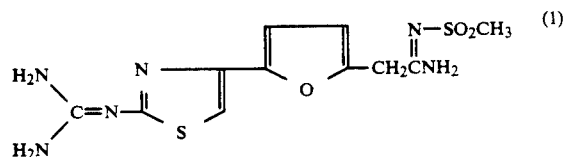
(1)

4-]5-(2-Amino-2-mesyliminoethyl)furan-2-yl]-2-(diaminomethyleneamino)thiazole.
mp: 168° to 169° C. (dec.).
IR (Nujol): 3460, 3400, 3350, 3240, 3170, 3120, 1660, 1640, 1620, 1540 cm$^{-1}$.
NMR (DMSO-d$_6$, δ): 2.88 (3H, s), 3.69 (2H, s), 6.32 (1H, d, J=3 Hz), 6.61 (1H, d, J3 Hz), 6.77 (1H, s), 6.86 (4H, s), 7.83 (1H, s), 8.50 (1H, s).
Anal. Calcd. for $C_{11}H_{14}N_6O_3S_2 \cdot H_2O$: C 36.66, H 4.47, N 23.32, H$_2$O 5.00 Found: C 36.80, H 4.31, N 23.44, H$_2$O 5.22.

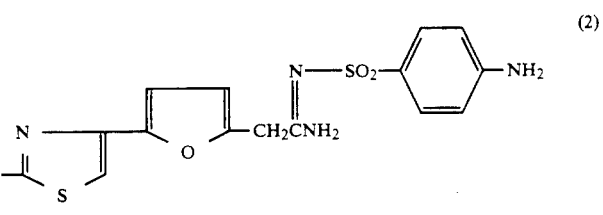
(2)

4-[5-{2-Amino-2-(p-aminophenylsulfonyl)iminoethyl}furan-2-yl]-2-(diaminomethyleneamino)thiazole.
mp: 190°-191° C. (dec.).
IR (Nujol): 3400, 3340, 1635, 1600, 1550 cm$^{-1}$.
NMR (DMSO-d$_6$, δ): 3.63 (2H, s), 5.81 (2H, s), 6.19 (1H, d, J=3 Hz), 6.55 (2H, d, J=8 Hz), 6.58 (1H, d, J=3 Hz), 6.70 (1H, s), 6.87 (4H, s), 7.45 (2H, d, J=8 Hz), 7.85 (1H, s), 8.47 (1H, s).
Anal. Calcd. for $C_{16}H_{17}N_7O_3S_2$: C 45.81, H 4.08, N 23,37 Found: C 45.92, H 4.21, N 22.95.

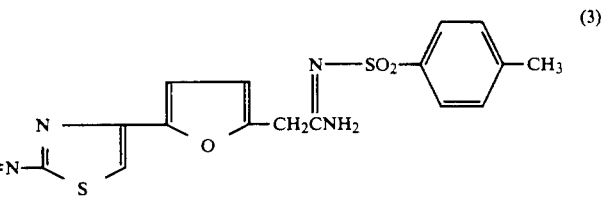
(3)

4-[5-(2-Amino-2-tosyliminoethyl)furan-2-yl]-2-(diaminomethyleneamino)thiazole.
mp: 207°-209° C. (dec.).

IR (Nujol): 3450, 4320, 3380, 3320, 1670, 1630, 1605, 1550 cm$^{-1}$.

NMR (DMSO-d$_6$, δ): 2.33 (3H, s), 3.68 (2H, s), 6.20 (1H, d, J=3 Hz), 6.57 (1H, d, J=3 Hz), 6.64 (1H, s), 6.90 (4H, s), 7.26 (2H, d, J=8 Hz), 7.67 (2H, d, J=8 Hz), 8.10 (1H, s), 8.76 (1H, s).

Anal. Calcd. for C$_{17}$H$_{18}$N$_6$O$_3$S$_2$: C 48.79, H 4.34, N 20.08 Found: C 48.44, H 4.19, N 19.77.

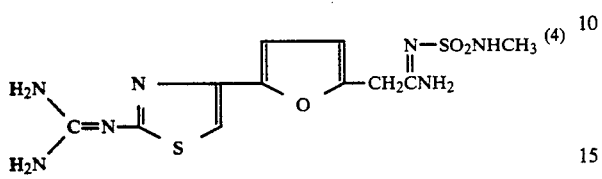

4-[5-(2-Amino-2-methylaminosulfonyliminoethyl)furan-2-yl]-2-(diaminomethyleneamino)thiazole.

mp: 219° to 220° C. (dec.).

IR (Nujol): 3480, 3430, 3380, 3380, 3330, 1610, 1530 cm$^{-1}$.

NMR (DMSO-d$_6$, δ): 2.42 (3H, d, J=5 Hz), 3.65 (2H, s), 6.32 (1H, d, J=3 Hz), 6.59 (1H, q, J=5 Hz), 6.62 (1H, d, J=3 Hz), 6.75 (1H, s), 6.89 (4H, s), 7.63 (1H, s), 8.42 (1H, s).

Anal. Calcd. for C$_{11}$H$_{15}$N$_7$O$_3$S$_2$: C 36.97, H 4.23, N 27.43 Found: C 36.93, H 4.15, N 27.41.

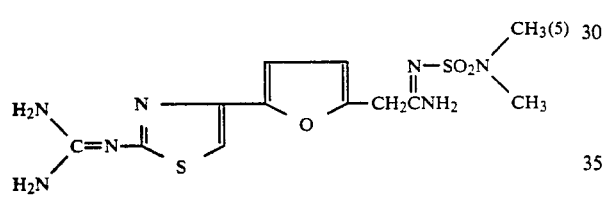

4-[5-{2-Amino-2-(N,N-dimethylamino)sulfonyliminoethyl}furan-2-yl]-2-(diaminomethyleneamino)thiazole.

mp: 161° C.

IR (Nujol): 3460, 3340, 1660, 1630, 1565, 1515 cm$^{-1}$.

NMR (DMSO-d$_6$, δ): 2.51 (6H, s), 3.69 (2H, s), 6.33 (1H, d, J=3 Hz), 6.61 (1H, d, J=3 Hz), 6.75 (1H, s), 6.89 (4H, s), 7.81 (1H, s), 8.51 (1H, s).

Anal. Calcd. for C$_{12}$H$_{17}$N$_7$O$_3$S$_2$: C 38.80, H 4.61, N 26.40 Found: C 36.62, H 4.39, N 26.42.

EXAMPLE 26

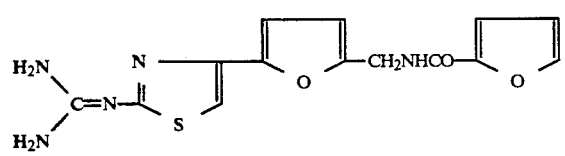

2-Furoyl chloride (0.48 g) was added slowly to a solution of 4-(5-aminomethylfuran-2-yl)-2-(diaminomethyleneamino)thiazole (0.80 g) in N,N-dimethylformamide (20 ml) with cooling on an ice bath and the mixture was stirred for an hour with cooling on an ice bath. The solvent was removed under reduced pressure and the residue was chromatographed on a silica gel column eluting with a mixture of chloroform and methanol (30:1, (V/V). Recrystallization from methanol afforded 2-(diaminomethyleneamino)-4-[5-(2-furoyl)aminomethylfuran-2-yl]thiazole (0.20 g).

mp: 246° C.

IR (Nujol): 3400, 1655, 1625, 1600 cm$^{-1}$.

NMR (DMSO-d$_6$, δ): 4.42 (2H, d, J=5.5 Hz), 6.26 (1H, d, J=3.8 Hz), 6.64–6.40 (2H, m), 6.72 (1H, s), 6.83 (4H, s), 7.11 (1H, dd, J=1.0 and 3.8 Hz), 7.77 (1H, m), 8.78 (1H, t, J=5.5 Hz).

Anal. Calcd. for C$_{14}$H$_{13}$N$_5$O$_3$S: C 50.75, H 3.95, N 21.14 Found: C 50.69, H 3.81, N 21.01.

EXAMPLE 27

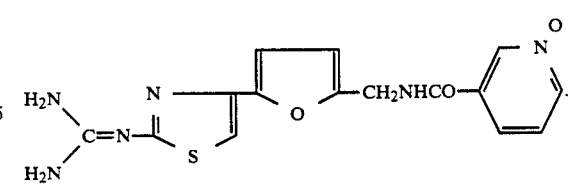

Dicyclohexylcarbodiimide (2.3 g) was added slowly to a suspension of nicotinic acid N-oxide (1.5 g) in N,N-dimethylformamide (40 ml) with cooling on an ice bath and the mixture was stirred for 15 minutes with cooling on an ice bath. To the mixture 4-(5-aminomethylfuran-2-yl)-2-(diaminomethyleneamino)thiazole (2.0 g) was added with cooling on an ice bath. The mixture was stirred for an hour with cooling on an ice bath and then stirred for 41 hours at room temperature. The solvent was removed under reduced pressure and the residue was suspended in water. 6N-Hydrochloric acid solution was added to the suspension and the resulting precipitate was removed by filtration. The solvent was removed under reduced pressure and the residue was dissolved in methanol. The insoluble material was removed by filtration and the solvent was removed under reduced pressure. The residue was chromatographed on a silica gel column eluting with a mixture of chloroform and methanol (10:1, V/V). Recrystallization from a mixture of methanol, dioxane and diisopropyl ether afforded 2-(diaminomethyleneamino)-4-[5-(1-oxonicotinoylaminomethyl)furan-2-yl]thiazole (0.30 g).

mp: 217° C.

IR (Nujol): 3420, 1670, 1550 cm$^{-1}$.

NMR (DMSO-d$_6$, δ): 4.51 (2H, d, J=5.5 Hz), 6.39 (1H, d, J=3.2 Hz), 6.63 (1H, d, J=3.2 Hz), 6.78 (1H, s), 6.90 (4H, s), 7.52 (1H, dd, J=6.4 and 8.0 Hz), 7.76 (1H, d, J=8.0 Hz), 8.37 (1H, d, J=6.4 Hz), 8.62 (1H, s), 9.31 (1H, t, J=5.5 Hz), Anal. Calcd. for C$_{15}$H$_{14}$N$_6$O$_3$S.3/4H$_2$O: C 48.45, H 4.20, N 22.59 Found: C 48.79, H 4.03, N 22.22.

EXAMPLE 28

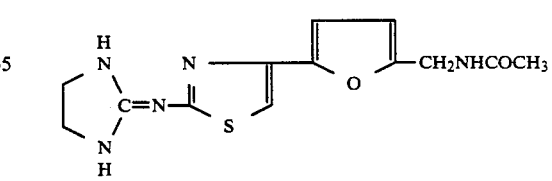

A mixture of 4-(5-acetylaminomethylfuran-2-yl)-2-thioureidothiazole (1.50 g) and methyl iodide (0.32 ml) in methanol (30 ml) and tetrahydrofuran (15 ) was refluxed for 5 hours with stirring. After the solvent was evaporated in vacuo to give 2-[(amino)(methylthio)methyleneamino]-4-(5-acetylaminomethylfuran-2l-yl)thiazole, the residue was mixed with ethylenediamine (0.91 g) and ethanol (30 ml) and the mixture was refluxed for 18 hours. After cooling, the resulting precipitate was collected by filtration and mixed with water (30 ml). The suspension was acidified to pH 2 with 6N hydrochloric acid, and then made basic to pH 11 with an aqueous potassium carbonate. The resulting precipitate was collected, washed with water and recrystallized from a mixture of methanol and tetrahyrofuran to afford 4-(5-acetylaminomethylfuran-2-yl)-2-(imidazolidin-2-ylideneamino)thiazole (0.51 g).

mp: 239° to 240° C.

IR (Nujol): 3290, 3105, 1630 cm$^{-1}$.

NMR (DMSO-d$_6$, δ): 1.88 (3H, s), 3.57 (4H, s), 4.33 (2H, d, J=6 Hz), 6.33 (1H, d, J=3 Hz), 6.82 (1H, s), 6.85 (1H, d, J=3 Hz), 7.68 (2H, s) and 8.33 (1H, t, J=6 Hz).

Anal. Calcd. for C$_{13}$H$_{15}$N$_5$O$_2$S: C 51.13, H 4.95, N 22.93 Found: C 50.91, H 4.62, N 22.85.

EXAMPLE 29

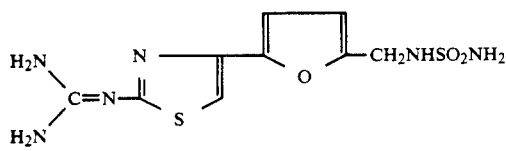

A suspension of 4l-(5-aminomethylfuran-2-yl)-2-(diaminomethyleneamino)thiazole (1.6 g) and sulfamide (1.0 g) in ethylene glycol dimethyl ether (30 ml) was refluxed for 24 hours. The solvent was removed under reduced pressure and the residue was chromatographed on an alumina column eluting with a mixture of chloroform and methanol (4:1, V/V). Recrystallization from a mixture of methanol, ethyl acetate and diisopropy ether afforded 2-(diaminomethyleneamino)-4-(5-sulfamoylaminomethylfuran-2-yl)thiazole (1.16 g).

mp: 175° to 177° C. (dec.).

IR (Nujol): 3400, 3360, 1650, 1530, 1140 cm$^{-1}$.

NMR (DMSO-d$_6$, δ): 4.01 (2H, d, J=6.1 Hz), 6.38 (1H, d, J=3.2z), 6.62 (1H, d, J=3.2 Hz), 6.67 (2H, s), 6.83 (1H, s), 6.96 (4H, s), 7.07 (1H, t, J=6.1 Hz).

Anal. Calcd. for C$_9$H$_{12}$N$_6$O$_3$S$_2$: C 34.17, H 3.82, N 26.55. Found: C 33.92, H 3.79, N26.55.

EXAMPLE 30

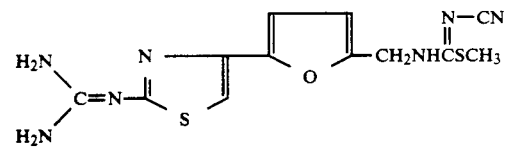

A mixture of 4-(5-aminomethylfurar-2yl)-2-(diaminomethyleneamino)thiazole (2.50 g) and dimethyl N-cyanodithioiminocarbonate (1.54 g) in ethanol (25 ml) was refluxed for two hours with stirring. After the solvent was evaporated in vacuo, the residue was chromatographed on alumina eluting with a mixture of chloroform and methanol (20:1, V/V), followed by recrystallization from a mixture of methanol, tetrahydrofuran and diisopropyl ether to afford 2-(diaminomethyleneamino)-4-[5-(3-cyano-2-methylisothioureido)methylfuran-2-yl]thiazole (1.48 g).

mp: 210° C. (dec.),

IR (Nujol): 3450, 3300, 3270, 2165, 1655 cm$^{-1}$.

NMR (DMSO-d$_6$, δ): 2.59 (3H, s), 4.48 (3H, s), 6.33 (1H, d, J=3 Hz), 6.58 (1H, d, J=3 Hz), 6.73 (1H, s), 6.83 (4H, s) and 8.82 (1H, br s).

Anal. Calcd. for C$_{12}$H$_{13}$N$_7$OS$_2$: C 42.97, H 3.91, N 29.23 Found: C 43.08, H 3.65, N 29.38.

EXAMPLE 31

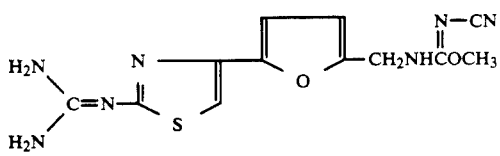

A mixture of 2-(diaminomethyleneamino)-4-[5-(3-cyano-2-methyl-1-isothioureido)methylfuran-2-yl]thiazole (1.35 g) and 28% methanolic sodium methoxide by weight (0.78 g) in methanol was refluxed for one hour with stirring. After the solvent was evaporated in vacuo, the residue was mixed with water (5 ml) and the medium was adjusted to pH 9 with 6N-hydrochloric acid.

The insoluble material was collected by filtration, washed with water and recrystallized from aqueous N,N-dimethylformamide to afford 4-[5-(3-cyano-2-methyl-1-isoureido)methylfuran-2-yl]-2-(diaminomethyleneamino)thiazole (0.82 g).

mp: 205° to 206° C.

IR (Nujol): 3460, 3345, 2180, 1630 cm$^{-1}$.

NMR (DMSO-d$_6$, δ); 3.83 (3H, s), 4.33 (2H, s), 6.33 (1H, d, J=3 Hz), 6.61 (1H, d, J=3 Hz), 6.74 (1H, s), 6.87 (4H, s) and 8.50 (1H, br s).

Anal. Calcd. for C$_{12}$H$_{13}$N$_7$O$_2$S: C 45.13, H 4.10, N 30.70 Found: C 44.93, H 4.33, N 30.42.

EXAMPLE 32

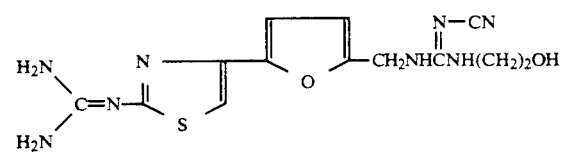

A mixture of 2-(diaminomethyleneamino)-4-[5-(3-cyano-2-methyl-1-isothioureido)methylfuran-2-yl]thiazole (1.10 g) and monoethanolamine (1 ml) in N,N-dimethylformamide (10 ml) was stirred at 70° C. for 7 hours. The solvent was evaporated in vacuo and the residue was mixed with water. The resulting precipitate was collected by filtration, washed with water and recrystallized from a mixture of dioxane, methanol and diisopropyl ether to afford 4-[5-{2-cyano-3-(2-hydroxyethyl)guanidino}methylfuran-2-yl]-2-(diaminomethyleneamino)thiazole (0.80 g).

mp: 208° to 209° C.

IR (Nujol): 3500, 3390, 3350, 3300, 2160, 1610 cm$^{-1}$.

NMR (DMSO-d$_6$, δ): 3.23-3.52 (4H, m), 4.40 (2H, d, J=5 Hz), 4.92 (1H, t, J=4 Hz), 6.34 (1H, d, (J=3 Hz), 6.62 (1H, d, J=3 Hz), 6.80 (1H, s), 6.90 (4H, s) and 7.52 (1H, t, J=5 Hz).

Anal. Calcd. for C$_{13}$H$_{16}$N$_8$O$_2$S: C 44.82, H 4.63, N 32.16 Found: C 45.12, H 4.91, N 32.10.

EXAMPLE 33

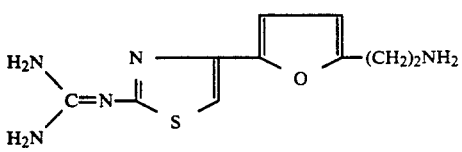

A solution of trifluoroacetic acid (24.9 ml) in tetrahydrofuran (50 ml) was dropwise added to a mixture of sodium borohydride (12.2 g) in tetrahydrofuran (100 ml) for an hour under ice-cooling and the mixture was stirred for 30 minutes at the same temperature.

To this mixture was dropwise added a mixture of 4-(5-cyanomethylfuran-2-yl)-2-(diaminomethyleneamino)thiazole (16.0 g) in tetrahydrofuran (30 ml) for 30 minutes under ice-cooling and the mixture was stirred for an hour at ambient temperature. The reaction mixture was added to a mixture of ethyl acetate and water and the mixture was adjusted to pH 1 with 6N-hydrochloric acid. The separated aqueous layer was adjusted to pH 10 with 10% aqueous sodium hydroxide and the mixture was extraced with a mixture of tetrahydrofuran and ethyl acetate. The extract layer was washed with brine and dired over magnesium sulfate. The solvent was concentrated to give 4-[5-(2-aminoethyl)furan-2-yl]-2-(diaminomethyleneamino)thiazole (4.71 g).

mp: 156°–158° C.

IR (Nujol): 3400, 1660, 1590, 1550 cm$^{-1}$.

NMR (DMSO-d$_6$, δ): 2.57–3.00 (4H, m), 6.16 (1H, d, J=3 Hz), 6.53 (1H, d, J=3 Hz), 6.71 (1H, s), 6.88 (4H, s).

EXAMPLE 34

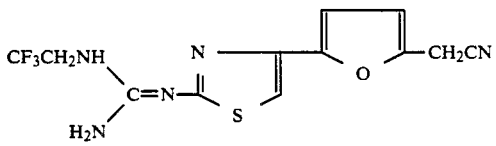

A mixture of 2-[(amino)(methylthio)methyleneamino]-[4-(5-cyanomethylfuran-2-yl)thiazole hydriodide (6.0 g) and 2,2,2-trifluoroethylamine (3.5 ml) in ethanol (120 ml) was refluxed for 18 hours. The solvent was removed by concentration and a residue was added to a mixture of water, ethyl acetate and tetrahydrofuran. The mixture was adjusted to pH 10.0 with potassium carbonate and a separated organic layer was washed with brine, dried over magnesium sulfate.

Evaporation of a solvent gave a residue, which was purified by column chromatography on silica gel eluting with a mixture of chloroform and methanol (19:1, V/V). The eluted fractions containing the desired product were collected and evaporated in vacuo to give 2-[(amino) {(2,2,2-trifluoroethyl)amino}methyleneamino]-4-(5-cyanomethylfuran-2-yl)thiazole (2.41 g).

mp: 152° to 153° C.

IR (Nujol): 3450, 3400, 2260, 1630, 1540 cm$^{-1}$.

NMR (DMSO-d$_6$, δ): 4.02–4.15 (2H, m), 4.23 (2H, s), 6.47 (1H, d, J=3 Hz), 6.72 (1H, d, J=7 Hz), 6.87 (1H, s), 7.14 (1H, br s), 7.77 (2H, br s).

EXAMPLE 35

The following compounds were obtained according to a similar manner to that of Example 34.

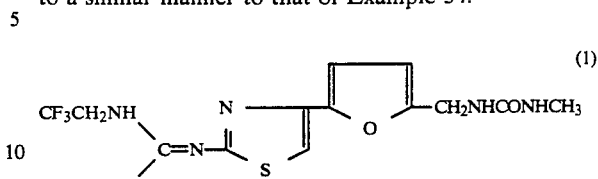

2-[(Amino) {(2,2,2,-trifluoroethyl)amino}methyleneamino]-4-[5-(3-methylureido)methylfuran-2-yl]thiazole.

mp: 170° to 171° C.

IR (Nujol): 3375, 3330, 1630, 1570, 1545 cm$^{-1}$.

NMR (DMSO-d$_6$, δ): 2.57 (3H, d, J=5 Hz), 4.00–4.23 (2H, m), 4.22 (2H, d, J=6 Hz), 5.82 (1H, q, J=5 Hz), 6.25 (1H, d, J=3 Hz), 6.35 (1H, t, J=6 Hz), 6.63 (1H, d, J=3 Hz), 6.87 (1H, s), 7.12 (1H, br s), 7.75 (1H, br s).

Anal. Calcd. for $C_{13}H_{15}N_6O_2SF_3$.1/5H$_2$O: C 41.00, H 4.10, N 22.07 Found: C 41.11, H 3.95, N 21.67.

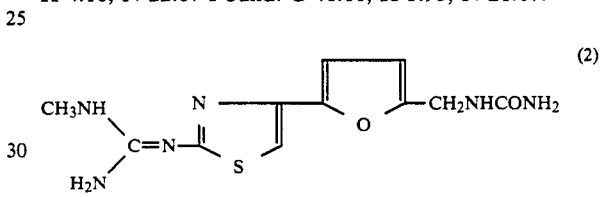

2-[(Amino)(methylamino)methyleneamino]-4-(5-ureidomethylfuran-2-yl)thiazole.

mp: 210° to 211° C.

IR (Nujol): 3490, 3400, 3340, 3300, 3110, 1640, 1595 cm$^{-1}$.

NMR (DMSO-d$_6$, δ): 2.73 (3H, d, J=5 Hz), 4.18 (2H, d, J=5 Hz), 5.52 (2H, s), 6.23 (1H, d, J=3 Hz), 6.35 (1H, t, J=5 Hz), 6.57 (1H, d, J=3 Hz), 6.87–7.18 (1H, m), 7.39 (2H, s).

Anal. Calcd. for $C_{11}H_{14}N_6O_2S$: C 44.89, H 4.79, N 28.55 Found: C 45.05, H 4.79, N 28.20.

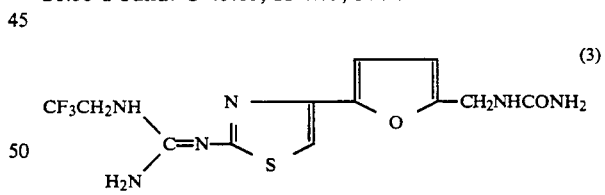

2-[(Amino){(2,2,2-trifluoroethyl)amino}methyleneamino[-4-5-ureidomethylfuran-2-yl)thiazole.

mp: 198° to 200° C.

IR (Nujol): 3400, 3300, 1635, 1570, 1550 cm$^{-1}$.

NMR (DMSO-d$_6$, δ): 4.01–4.20 (2H, m), 4.19 (2H, d, J=6 Hz), 5.56 (2H, s), 6.26 (1H, d, J=3 Hz), 6.38 (1H, t, J=6 Hz), 6.64 (1H, d, J=3 Hz), 6.88 (1H, s), 7.13 (1H, s), 7.75 (2H, s).

Anal. Calcd. for $C_{12}H_{13}N_6O_2SF_3$: C 39.78, H 3.62, N 23.19 Found: C 3993, H 3.71, N 23.15.

EXAMPLE 36

The following compound was obtained according to a similar manner to that of the latter half of Example 28.

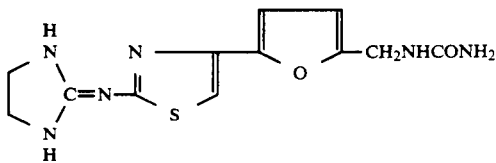

2-(Imidazolidin-2-ylideneamino)-4-(5-ureidomethylfuran-2-yl)thiazole.

mp: 245° to 247° C. (dec.).

IR (Nujol): 3430, 3375, 3310, 1650, 1625, 1590 cm$^{-1}$.

NMR (DMSO-d$_6$, δ): 3.53 (4H, s), 4.21 (2H, d, J=5 Hz), 5.60 (2H, s), 6.27 (1H, s), 6.41 (1H, t, J=5 Hz), 6.78 (1H, s), 6.82 (1H, s), 7.57 (2H, s).

Anal. Calcd. for C$_{12}$H$_{14}$N$_6$O$_2$S: C 47.05, H 4.61, N 27.43 Found: C 46.91, H 4.69, N 26.99.

EXAMPLE 37

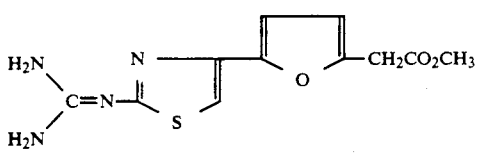

An ice-cooled mixture of 4-(5-cyanomethylfuran-2yl)-2-(diaminomethyleneamino)thiazole (30.0 g) in dry methanol (250 ml) and chloroform (250 ml) was bubbled with hydrogen chloride for 2 hours and the mixture was stirred for 3 hours under ice-cooling. To a mixture was added a diisopropyl ether (300 ml) and the isolated precipitate was collected by filtration. To a precipitate was added a solution of methanol (100 ml) and water (200 ml) and a mixture was stirred for 30 minutes at ambient temperature.

The mixture was adjusted to pH 9.5 with potassium carbonate and the mixture was extracted with a mixture of tetrahydrofuran and ethyl acetate. The extract layer was washed with a brine and dried over magnesium sulfate. Evaporation of a solvent gave a residue, which was triturated with diisopropyl ether to give 2-(diaminomethyleneamino)-4-(5-methoxycarbonylmethylfuran-2-yl)-thiazole (24.4 g).

mp: 187° to 193° C.

IR (Nujol): 3450, 3350, 3120, 1730, 1660, 1600, 1550 cm$^{-1}$.

NMR (DMSO-d$_6$, δ): 3.65 (3H, s), 3.83 (2H, s), 6.35 (1H, d, J=3 Hz), 6.62 (1H, d, J=3 Hz), 6.77 (1H, s), 6.91 (4H, s).

EXAMPLE 38

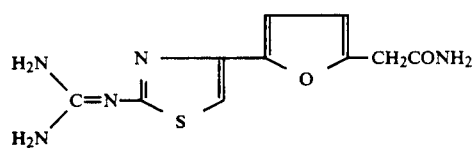

An ice-cooled solution of 2-(diaminomethyleneamino)-4-(5-methoxycarbonylmethylfuran-2-yl)thiazole (1.0 g) in methanol (20 ml) was bubbled with ammonia for 30 minutes and a mixture was stirred at ambient temperature for 25 hours. Evaporation of a solvent gave a residue, which was purified by column chromatography on silica gel eluting with a mixture of chloroform and methanol (9:1, V/V). The eluted fractions containing the desired product were collected and evaporated in vacuo. The residue was recrystallized from a mixture of ethanol, dioxane and diisopropyl ether to give 4-(5-carbamoylmethylfuran-2yl)-2-(diaminomethyleneamino)thiazole (0.44 g).

mp: 219° to 220° C.

IR (Nujol): 3360, 3160, 3110, 1650, 1600, 1530 cm$^{-1}$.

NMR (DMSO-d$_6$, δ): 3.51 (2H, s), 6.25 (1H, d, J=3 Hz), 6.58 (1H, d, J=3 Hz), 6.73 (1H, s), 6.87 (4H, s), 6.95 (1H, br s), 7.40 (1H, br s).

Mass: m/e 265 (M+).

Anal. Calcd. for C$_{10}$H$_{11}$N$_5$O$_2$S: C 45.28, H 4.18, N 26.40 Found: C 44.77, H 4.13, N 26.23.

EXAMPLE 39

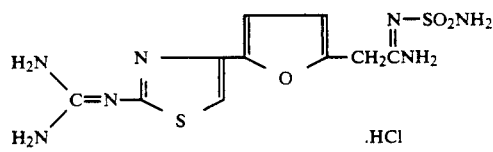

A solution of 4N-hydrogenchloride in 1,4-dioxane (2.2 ml) was added to a mixture of 4-[5-(2-amino-2-aminosulfonyliminoethyl)furan-2-yl]-2-(diaminomethyleneamino)thiazole (3.0 g) in methanol (60 ml) and the mixture was stirred at ambient temeprature for 4 hours. To a mixture was added a diisopropyl ether (30 ml) and the isolated precipitate was collected by filtration. The precipitate was recrystallized from an aqueous ethanol to give 4-[5-(2-amino-2-aminosulfonyliminoethyl)furan-2-yl]-2-(diaminomethyleneamino)thiazole hydrochloride (2.17 g).

mp: 219° to 221° C.

IR (Nujol): 3380, 3340, 1680, 1640, 1615, 1550, 1505 cm$^{-1}$.

NMR (DMSO-d$_6$, δ): 3.63 (2H, s), 6.38 (1H, d, J=3 Hz), 6.54 (1H, br s), 6.94 (1H, d, J=3 Hz), 7.20 (1H, s), 7.31 (1H, s), 8.32 (5H, br s).

Anal. Calcd. for C$_{10}$H$_{13}$N$_7$O$_3$S$_2$.HCl: C 31.62, H 3.71, N 25.81, Cl 9.33 Found: C 31.02, H 3.71, N 25.53, Cl 9.43.

EXAMPLE 40

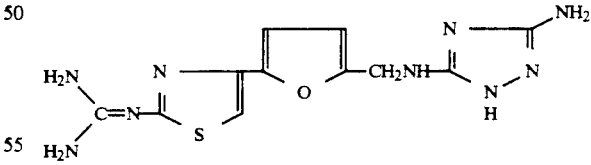

A mixture of 2-(diaminomethyleneamino(4-[5-(3-cyano-2-methyl-1-isothioureido)methylfuran-2-yl]thiazole (0.80 g) and hydrazine hydrate (1.2 g) in ethanol (10 ml) was stirred at ambient temperature for two hours. After cooling, the resulting precipitate was collected by filtration and recrystallized from aqueous N,N-dimethylformamide to afford 4-[5-{(3-amino-1H-1,2,4-triazol-5-yl)aminomethyl}furan-2-yl]-2-(diaminomethyleneamino)thiazole (0.52 g).

mp: 241° to 242° C.

IR (Nujol): 3570, 3470, 3360, 3295, 1630 cm$^{-1}$.

NMR (DMSO-d₆, δ): 4.23 (2H, d, J=6 Hz), 5.34 (2H, br s), 5.93 (1H, br s), 6.23 (1H, d, J=3 Hz), 6.55 (1H, d, J=3 Hz), 6.73 (1H, s), and 6.85 (4H), br s).

Anal. Calcd. for C₁₁H₁₃N₉OS.H₂O: C 39.16, H 4.48, N 37.37, H₂O 5.34 Found: C 38.94, H 4.30, N 37.30, H₂O 5.70.

EXAMPLE 41

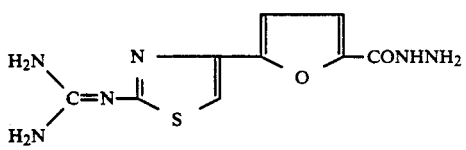

A solution of 2-(diaminomethyleneamino)-4-(5-methoxycarbonylfuran-2-yl)thiazole (5.00 g) and hydrazine hydrate (9.40 g) in ethanol (50 ml) was refluxed for 4 hours with stirring. The mixture was cooled and the resulting precipitate was collected by filtration to afford 2-(diaminomethyleneamino)-4-(5-hydrazinocarbonylfuran-2yl)thiazole (4.86 g).

mp: 279° to 280° C.

IR (Nujol): 3400, 3360, 3320, 3250, 3175, 3125, 1160, 1630 cm⁻¹.

NMR (DMSO-d₆, δ): 4.53 (2H, br s), 6.85 (1H, d, J=3 Hz), 6.98 (4H, br s), 7.18 (1H, d, J=3 Hz), 7.27 (1H, s) and 9.77 (1H, br s).

EXAMPLE 42

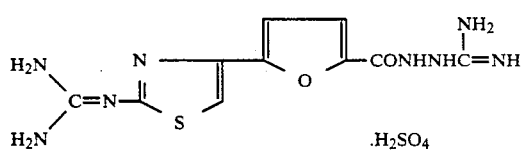

A solution of 2-diaminomethyleneamino)-4(5-hydrazinocarbonylfuran-2-yl)thiazole (1.50 g) and S-methylisothiourea hemisulfate (1.57 g) in dimethyl sulfoxide (12 ml) was heated at 180° C. for two hours with stirring. After cooling, the resulting precipitate was collected by filtration and washed with dimethyl sulfoxide followed by washing with isopropyl alcohol and diisopropyl ether to afford 2-(diaminomethyleneamino)-4-(5-guanidinocarbamoylfuran-2-yl)thiazole sulfate (1.83 g).

mp: >300° C.

IR (Nujol): 3325, 3150, 3110, 1690, 1670 cm⁻¹.

Anal. Calcd. for C₁₀H₁₂N₈O₂S.H₂SO₄: C 29.55, H 3.47, N 27.57 Found: C 28.07, H 3.72, N 28.22.

EXAMPLE 43

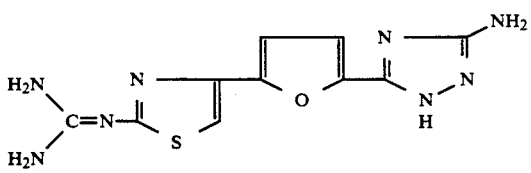

A suspension of 2-(diaminomethyleneamino)-4-(5-guanidinocarbamoylfuran-2-yl-)thiazole sulfate (1.70 g) in concentrated ammonium hydroxide (17 ml) was refluxed with stirring. Additional ammonium hydroxide (8.5 ml) was added twice. After refluxing for 8 hours, water was added to the mixture and the resulting precipitate was collected by filtration, followed by recrystallization from aqueous N,N-dimethylformamide to afford 4-[5-(3-amino-1H-1,2,4-triazol-5-yl)furan-2-yl]-2-(diaminomethyleneamino)thiazole (0.73 g).

mp: >300° C.

IR (Nujol): 3440, 3400, 4440, 3120, 1670, 1640 cm⁻¹.

NMR (DMSO-d₆, δ): 6.00 (2H, s), 6.76 (2H, s), 6.87 (1H, s), 6.92 (4H, s).

Anal. Calcd. for C₁₀H₁₀N₈OS.1/4H₂O: C 40.74, H 3.59, N 38.17, H₂O 1.53 Found: C 40.48, H 3.55, N 37.61, H₂O 1.25.

EXAMPLE 44

The following compounds were obtained according to a similar manner to that of Example 30.

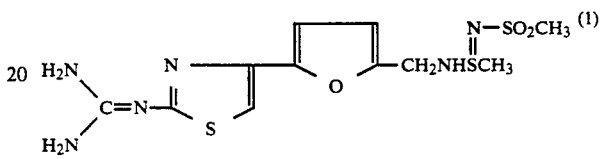

2-(Diaminomethyleneamino)-4-[5-(3- mesyl-2-methyl-1-isothioureido)methylfuran-2-yl]thiazole.

mp: 210 ° to 211° C.

IR (Nujol): 3420, 3320, 1655, 1350, 1120 cm⁻¹.

NMR (DMSO-d₆, δ) : 2.53 (3H, s), 3.00 (3H, s), 4.58 (2H, s), 6.45 (1H, d, J=3 Hz), 6.72 (1H, d, J=3 Hz), 6.85 (1H, s), 6.95 (4H, s) and 8.50 (1H, br s).

Anal. Calcd. for C₁₂H₁₆N₆O₃S₂: C 37.10, H 4.15, N 21.63 Found: C37.42, H 4.36, N 21.76.

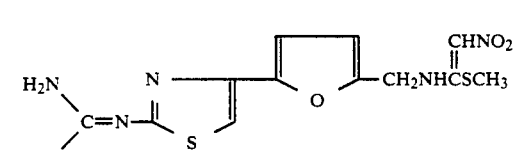

2-(Diaminomethyleneamino)-4-[5-{N-(1-methylthio-2-nitrovinyl) aminomethyl}furan-2-yl]thiazole.

mp: 214° C. (dec).

IR (Nujol): 3350, 1660, 1610, 1550 cm⁻¹.

NMR (DMSO-d₆, δ): 2.45 (3H, s), 4.65 (2H, d, J=5.4 Hz), 6.38 (1H, d, J=3.6 Hz), 6.65–6.57 (2H, m), 6.72 (1H, s), 6.76 (4H, s), 10.55 (1H, br).

EXAMPLE 45

The following compounds were obtained according to a similar manner to that of Example 32.

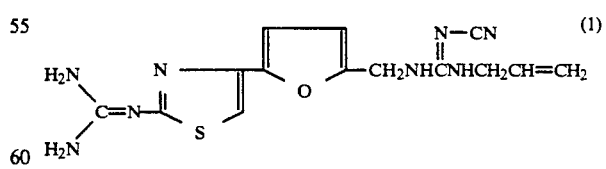

4-[5-Allyl-2-cyanoguanidino)methylfuran-2-yl]-2-(diaminomethyleneamino)thiazole.

mp: 164° to 165° C.

IR (Nujol): 3425, 3240, 2160, 1645 cm⁻¹.

NMR (DMSO-d₆, δ): 3.78 (2H, t, J=6 Hz), 4.36 (2H, d, J=6 Hz), 5.01 (1H, d, J=1.5 Hz), 5.16 (1H, dd, J=1.5 Hz and 8 Hz), 5.62–6.03 (1H, m), 6.28 (1H, d, J=3 Hz), 6.61 (1H, d, J=3 Hz), 6.74 (1H, s), 6.86 (4H, s) and 7.14–7.46 (2H, m).

Anal. Calcd. for $C_{14}H_{16}N_8OS$: C 48.83, H 4.68, N 32.54 Found: C 48.86, H 4.41, N 32.58.

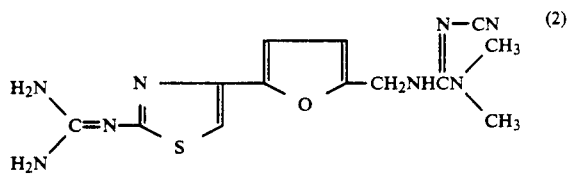

4-[5-(2-Cyano-3,3-dimethylguanidino)methylfuran-2-yl]-2-(diaminomethyleneamino)thiazole.

mp: 205° to 206° C.

IR (Nujol): 3350, 2160, 1650 cm$^{-1}$.

NMR (DMSO-d$_6$, δ): 2.99 (6H, s), 4.51 (2H, d, J=5.6 Hz), 6.36 (1H, d, J=3.2 Hz), 6.63 (1H, d, J=3.2 Hz), 6.78 (1H, s), 6.91 (4H, s), 7.54 (1 H, t, J=5.6 Hz ).

Anal. Calcd. for $C_{13}H_{16}N_8OS$: C 46.98, H 4.85, N 33.71 Found: C 47.14, H 4.92, N 33.66.

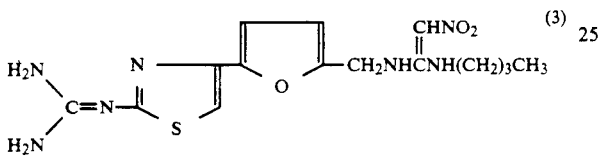

4-[5-{N-(1-n-Butylamino-2-nitrovinyl)aminomethyl}-furan-2-yl]-2-(diaminomethyleneamino)thiazole.

mp: 215° to 217° C.

IR (Nujol): 3360, 1610, 1550, 1370 cm$^{-1}$.

NMR (DMSO-d$_6$, δ): 0.89 (3H, t, J=7.2 Hz), 1.53–1.27 (2H, m), 2.52–2.48 (2H, m), 3.22 (2H, br), 4.43 (2H, br), 6.41 (1H, d, J=3.2 Hz), 6.65–6.64 (2H, m), 6.76 (1H, s), 6.89 (4H, s), 7.75 (1H, br), 10.17 (1H, br).

Anal. Calcd. for $C_{15}H_{21}N_7O_3S$: C 47.48, H 5.58, N 25.84 Found: C47.44, H 5.71, N 25.97.

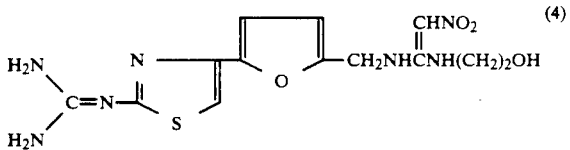

2-(Diaminomethyleneamino)-4-[5-[N-{1-(2-hydroxyethyl)amino-2-nitrovinyl}aminomethyl]furan-2-yl]thiazole.

mp: 182° to 183° C. (dec).

IR (Nujol): 3330, 1610, 1550, 1380 cm$^{-1}$.

NMR (DMSO-d$_6$, δ): 3.65–3.00 (4H, m), 4.34 (2H, d, J=4.8 Hz), 5.10–4.60 (1H, br), 6.29 (1H, d, J=3.0 Hz), 6.52 (2H, s), 6.67 (1H, s), 6.75 (4H, s), 7.90–7.30 (1H, br), 10.30–9.30 (1H, br).

Anal. Calcd. for $C_{13}H_{17}N_7O_4S.3/4H_2O$ C 40.99, H 4.90, N 25.74 Found: C 41.04, H 5.13, N 26.04.

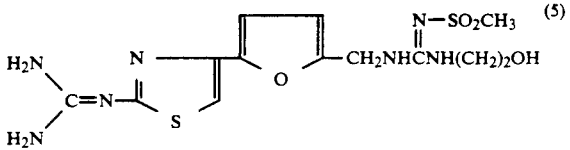

2-(Diaminomethyleneamino)-4- [5-{3-(2-hydroxyethyl)-2-mesylguanidino}methylfuran-2-yl]thiazole.

mp: 202° to 203° C.

IR (Nujol): 3570, 3410, 3340, 3220, 3120, 1610, 1375, 1360, 1340, 1100 cm$^{-1}$.

NMR (DMSO-d$_6$, δ): 2.80 (3H, s), 3.14–3.26 (2H, m), 3.43–3.60 (2H, m), 4.39 (2H, d, J=6 Hz), 4.91 (1H, t, J=5 Hz), 6.34 (1H, d, J=3 Hz), 6.62 (1H, d, J=3 Hz), 6.78 (1H, s), 6.86 (4H, s), 7.21 (1 H, t, J=5 Hz) and 7.49 (1H, t, J=6 Hz).

Anal. Calcd. for $C_{13}H_{19}N_7O_4S_2$: C 38.89, H 4.77, N 24.42 Found: C 38.89, H 5.20, N 24.22.

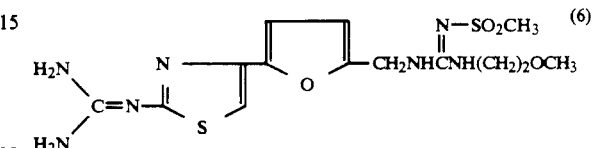

2-(Diaminomethyleneamino)-4-[5-{2-mesyl-3-(2l -methoxyethyl)guanidino}methylfuran-2-yl]thiazole.

mp: 173° to 174° C.

IR (Nujol): 3430, 3400, 3340, 1360, 1110 cm$^{-1}$.

NMR (DMSO-d$_6$, δ): 2.77 (3H, s), 3.23 (3H, s), 3.30–3.47 (4H, m), 4.39 (2H, d, J=6 Hz), 6.31 (1H, d, J=3 Hz), 6.60 (1H, d, J=3 Hz), 6.75 (1H, s), 6.87 (4H, s), 7.20 (1H, t, J=6 Hz) and 7.49 (1H, t, J=6 Hz).

Anal. Calcd. for $C_{14}H_{21}N_7O_4S_2$: C 40.47, H 5.09, N 23.60 Found: C 40.56, H 4.94, N 23.64.

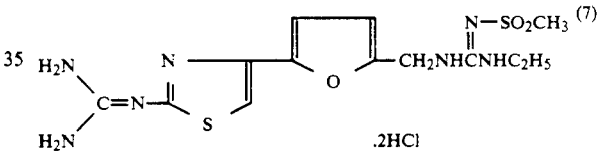

2-(Diaminomethyleneamino)-4-[5-(3-ethyl-2-mesylguanidino)methylfuran-2-yl]thiazole.

mp: 151° to 152° C.

IR (Nujol): 3380, 3230, 1680, 1650, 1340, 1160 cm$^{-1}$.

NMR (DMSO-d$_6$, δ): 1.09 (3H, t, J=7 Hz), 2.78 (3H, s), 3.13–3.26 (2H, m), 4.43 (2H, d, J=5 Hz), 6.40 (1H, d, J=3 Hz), 7.00 (1H, d, J=3 Hz), 7.18 (1H, br s), 7.30 (1H, s), 7.75 (1H, br s), 8.37 (4H, s) and 12.80 (1H, br s).

Anal. Calcd. for $C_{13}H_{19}N_7O_3S_2.2HCl.1/3H_2O$: C 33.62, H 4.70, N 21.11, Cl 15.27, H$_2$O 1.29 Found: C 33.75, H 4.53, N 21.05, Cl 15.06, H$_2$O 1.18.

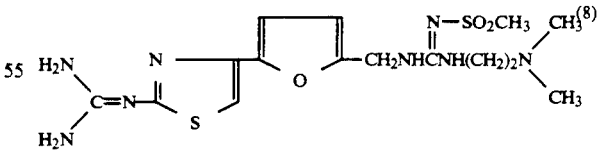

2-(Diaminomethyleneamino)-4-[5-{3-(2-dimethylaminoethyl)-2-mesylguanidino}methylfuran-2-yl]thiazole.

mp: 183° to 184° C.

IR (Nujol): 3450, 3410, 3340, 1650, 1330, 1110 cm$^{-1}$.

NMR (DMSO-d$_6$, δ): 2.13 (6H, s), 2.37 (2H, t, J=6 Hz), 2.78 (3H, s), 3.19–3.27 (2H, m), 4.37 (2H, d, J=5 Hz), 6.36 (1H, d, J=3 Hz), 6.63 (1H, d, J=3 Hz), 6.78 (1H, s), 6.90 (4H, br s), 6.90 (1H, t, J=5 Hz) and 8.14 (1H, br s).

Anal. Calcd. For C₁₅H₂₄N₈O₃S₂ C 42.04, H 5.64, N 26.15 Found: C 42.32, H 5.61, N 26.31.

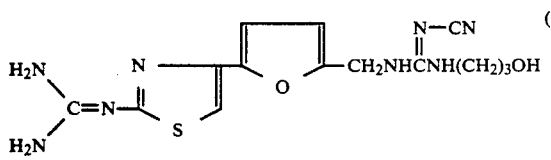
(9)

4-[5-{2-Cyano-3-(3-hydroxypropyl)guanidino}methylfuran-2-yl]-2-(diaminomethyleneamino)thiazole.

mp: 160° to 161° C.

IR (Nujol): 3350, 2040, 1650 cm⁻¹.

NMR (DMSO-d₆, δ): 1.56–1.69 (2H, m), 3.20 (2H, q, J=6 Hz), 3.43 (2H, q, J=5 Hz), 4.35 (2H, d, J=5.5 Hz), 4.53 (1H, t, J=5 Hz), 6.30 (1H, d, J=3 Hz), 6.62 (1H, d, J=3 Hz), 6.76 (1 H, s), 6.90 (4H, br s), 7.09 (1 H, t, J=5.5 Hz) and 7.47 (1H, t, J=6 Hz).

EXAMPLE 46

The following compound was obtained according to similar manners to those of Example 30 and Example 32, continuously.

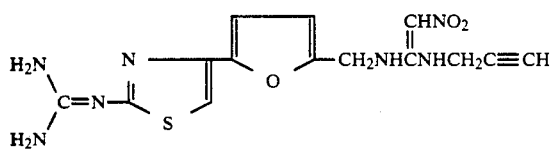

2-(Diaminomethyleneamino)-4-[5-{N-(2-nitro-1-propargylaminovinyl)aminomethyl}furan-2-yl]thiazole.

mp: 199° to 200° C. (dec.).

IR (Nujol): 3430, 1620, 1560, 1370 cm⁻¹.

NMR (DMSO-d₆, δ): 3.38–3.30 (1H, m), 4.20–3.80 (2H, m), 4.45 (2H, d, J=5.4 Hz), 6.35 (1H, d, J=3.3 Hz), 6.55 (1H, s), 6.58 (1H, d, J=3.3 Hz), 6.71 (1H, s), 6.78 (4H, s), 8.00 (1H, br), 10.00 (1H, br).

Anal. Calcd. for C₁₄H₁₅N₇O₃S: C 46.53, H 4.18, N 27.13 Found: C 46.18, H 4.92, N 26.83.

EXAMPLE 47

The following compound was obtained according to a similar manner to that of Example 37.

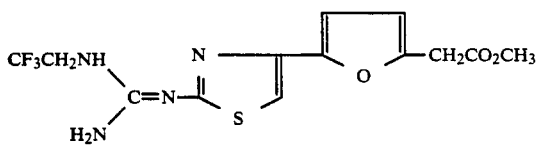

2-[(Amino){(2,2,2-trifluoroethyl)amino}methyleneamino]-4-(5-methoxycarbonylmethylfuran-2-yl)thiazole.

mp: 126° to 127° C.

IR (Nujol): 3410, 1715, 1630, 1550 cm⁻¹.

NMR (DMSO-d₆, δ): 3.66 (3H, s), 3.84 (2H, s), 4.01–4.22 (2H, m), 6.36 (1H, d, J=3 Hz), 6.66 (1H, d, J=3 Hz), 6.89 (1H, s), 7.14 (1H, br s), 7.76 (2H, s).

EXAMPLE 48

The following compounds were obtained according to a similar manner to that of Example 38.

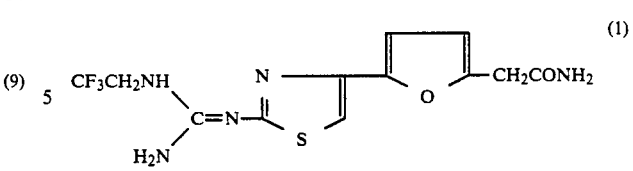
(1)

2-[(Amino){(2,2,2-trifluoroethyl)amino}methyleneamino]-4-(5-carbamoylmethylfuran-2-yl)thiazole.

mp: 163° to 165° C.

IR (Nujol): 3350, 3190, 1660, 1620, 1540 cm⁻¹.

NMR (DMSO-d₆, δ): 3.50 (2H, s), 3.90–4.27 (2H, m), 6.27 (1H, d, J=3 Hz), 6/63 (1H, d, J=3 Hz), 6.86 (1H, s), 6.94–7.30 (2H, m), 7.47 (1H, s), 7.75 (2H, br s).

Anal. Calcd. for C₁₂H₁₂H₅O₂SF₃: C 41.50, H 3.48, N 20.16 Found: C 41.10, H 3.45, N 19.51.

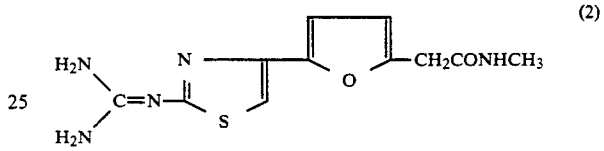
(2)

2-(Diaminomethyleneamino)-4-(5-methylcarbamoylmethylfuran-2- yl)thiazole.

mp: 212° to 213° C.

IR (Nujol): 3420, 3350, 1660, 1610, 1540 cm⁻¹.

NMR (DMSO-d₆, δ): 2.61 (3H, d, J=5 Hz), 3.51 (2H, s), 6.22 (1H, d, J=3 Hz), 6.56 (1H, d, J=3 Hz), 6.71 (1H, s), 6.84 (4H, s), 7.75 (1H, br s).

Mass: m/e 279 (M⁺).

Anal. Calcd. for C₁₁H₁₃N₅O₂S: C 47.30, H 4.69, N 25.07 Found: C 47.54, H 4.37, N 25.43.

EXAMPLE 49

The following compound was obtained according to a similar manner to that of Example 39.

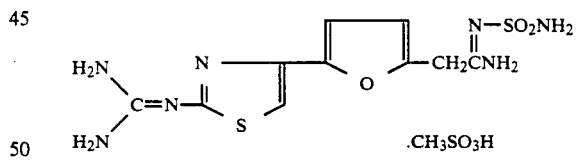

4-[5-(2-Amino-2-aminosulfonyliminoethyl)furan-2-yl]-2-(diaminomethyleneamino)thiazole methanesulfonate.

mp: 221° to 223° C. (dec.).

IR (Nujol): 3400, 3300, 3180, 3110, 1690, 1630, 1575 cm⁻¹.

NMR (DMSO-d₆, δ): 2.53 (3H, s), 3.65 (2H, s), 6.40 (1H, d, J=3 Hz), 6.56 (1H, br s), 6.95 (1H, d, J=3 Hz), 7.31 (1H, s), 7.41 (1H, br s), 8.31 (4H, s).

Anal. Calcd. for C₁₀H₁₃N₇O₃S₂·CH₃SO₃H: C 30.06, H 3.90, N 22.31, S 21.89 Found: C 30.03, H 3.91, N 22.54, S 21.87.

EXAMPLE 50

The followiong compound was obtained according to a similar manner to that of Example 29.

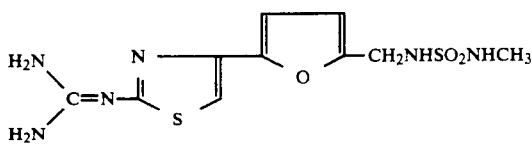

2-(Diaminomethyleneamino)-4-(5-methylsulfamoylaminomethylfuran-2-yl)thiazole.

mp: 197° C.

IR (Nujol): 3420, 3275, 1600 cm$^{-1}$.

NMR (DMSO-d$_6$, δ): 2.41 (3H, d, J=5.5 hz), 3.98 (2H, d, J=6.0 Hz), 6.32 (1H, d, J=3.0 Hz), 6.55 (1H, d, J=3.0 Hz), 6.62-6.72 (1H, m), 6.73 (1H, s), 6.82 (4H, s), 7.30 (1H, t, J=6.0 Hz).

Anal. Calcd. for C$_{10}$H$_{14}$N$_6$O$_3$S$_2$: C 36.35, H 4.27, N 25.44 Found: C 36.38, H 4.26, N 25.24.

EXAMPLE 51

The following compound was obtained according to a similar manner to that of Example 41.

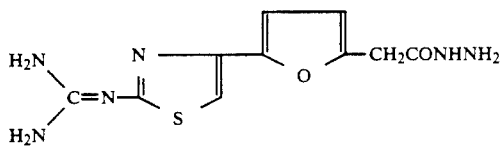

2-(Diaminomethyleneamino)-4-(5-hydrazinocarbonylmethylfuran-2-yl)thiazole.

mp: 222° to 223° C.

IR (Nujol): 3450, 3350, 3200, 1645, 1605, 1540 cm$^{-1}$.

NMR (DMSO-$_6$, δ): 3.53 (2H, s), 4.35 (2H, br s), 6.31 (1H, d, J=3 Hz), 6.64 (1H, d, J=3 Hz), 6.77 (1H, s), 6.94 (4H, s), 9.25 (1H, s).

EXAMPLE 52

The following compound was obtained according to a similar manner to that of Example 42.

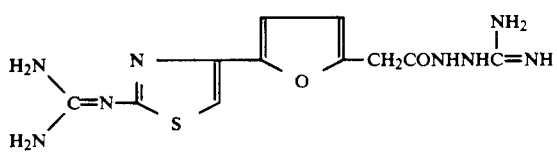

2-(Diaminomethyleneamino)-4-(5-guanidinocarbamoylmethylfuran-2-yl)thiazole.

mp: 250° to 251° C.

IR (Nujol): 3300, 3160, 1650, 1600, 1540 cm$^{-1}$.

NMR (DMSO-d$_6$, δ): 3.43 (2H, s), 6.22 (1H, d, J=3 Hz), 6.60 (1H, d, J=3 Hz), 6.73 ((1H, s), 6.93 (4H, s).

EXAMPLE 53

The following compound was obtained according to a similar manner to that of Example 43.

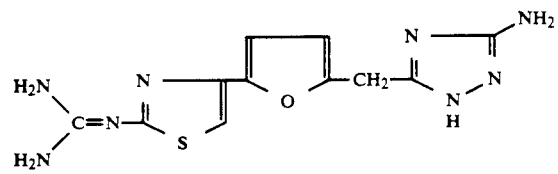

4-[5-(3-Amino-1H-1,2,4-triazol-5-yl)methylfuran-2-yl]-2-(diaminomethyleneamino)thiazole.

mp: 259° to 261° C. (dec.).

IR (Nujol): 3410, 3120, 1660, 1640, 1600, 1550 cm$^{-1}$.

NMR (DMSO-d$_6$, δ): 3.83 (2H, s), 5.71 (2H, br s), 6.18 (1H, d, J=3 Hz), 6.56 (1H, d, J=3 Hz ), 6.70 (1H, s), 6.86 (4H, s).

Anal. Calcd. for C$_{11}$H$_{12}$N$_8$OS. 1/2H$_2$O: C 42.17, H 4.18, N 35.76, H$_2$O 2.87 Found: C 42.12, H 4.12, N 35.96, H$_2$O 3.00.

EXAMPLE 54

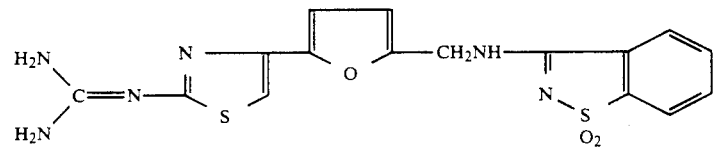

An ice-cooling mixture of 4-(5-aminomethylfuran-2-yl)-2-(diaminomethyleneamino)thiazole (0.8 g), 3-chlorobenzoisothiazol-1,1-dioxide (0.8 g) and triethylamine (0.5 ml) in N,N-dimethylformamide (15 ml) was stirred for 3 hours. To a reaction mixture was added a mixture of ethylacetate, tetrahydrofuran and water and the mixture was adjusted to pH 9.5 with 20% aqueous potassium carbonate. The separated organic layer was washed with brine and dried over magnesium sulfate. The solvent was removed by concentration and a residue was recrystallized from a mixture of methanol, dioxane and diisopropyl ether to give 2-(diaminomethyleneamino)-4-[5-(1,1-dioxobenzoisothiazol-3-yl)aminomethylfuran-2-yl]thiazole (0.49 g).

mp: 255° to 256° C. (dec.).

IR (Nujol): 3430, 3320, 1660, 1620, 1590, 1535 cm$^{-1}$.

NMR (DMSO-d$_6$, δ): 4.73 (2H, s), 6.51 (1H, d, J=3 Hz), 6.67 (1H, d, J=3 Hz), 6.82 (1H, s), 6.88 (4H, s), 7.63-8.06 (3H, m), 8.09-8.40 (1H, m), 9.89 (1H, br s).

Anal. Calcd. for C$_{14}$H$_{16}$N$_6$O$_3$S$_2$.1/3H$_2$O: C 47.05, H 3.62, N 20.49, H$_2$O 1.47 Found: C 47.04, H 4.28, N 20.49, H$_2$O 1.71.

EXAMPLE 55

The following compound was obtained according to a similar manner to that of Example 54.

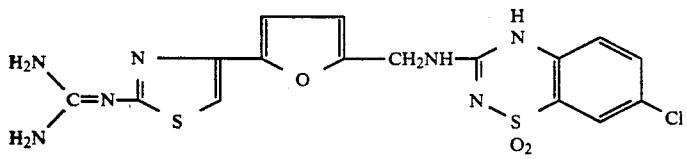

4-[5-(7-Chloro-1,1-dioxo-4H-1,2,4-benzothiadiazin-3-yl)aminomethylfuran-2-yl]-2-(diaminomethyleneamino)thiazole.

mp: 220° to 221° C.

IR (Nujol): 3325, 1690, 1630 cm$^{-1}$.

NMR (DMSO-d$_6$, δ): 4.49 (2H, d, J=4.5 Hz), 6.42 (1H, d, J=3 Hz), 6.71 (1H, d, J=3 Hz), 6.94 (1H, s), 7.24 (4H, br s), 7.26 (1H, d, J=8.5 Hz), 7.63 (1H, dd, J=2 Hz and 8.5 Hz), 7.69 (1H, d, J=2 Hz), 7.95 (1H, br s) and 11.07 (1H, br s).

Anal. Calcd. for C$_{16}$H$_{14}$ClN$_7$O$_3$S$_2$.1.5H$_2$O: C 40.13, H 3.58, N 20.47 Found: C 40.10, H 3.56, N 20.61.

EXAMPLE 56

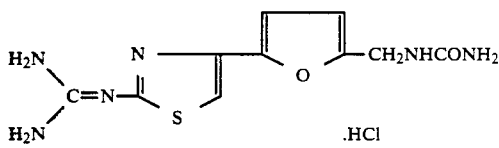

To a mixture of 2-(diaminomethyleneamino)-4-(5-ureidomethylfuran-2-yl)thiazole (15.4 g) in methanol (160 ml) was added a solution of 19% (W/V) hydrogen chloride in methanol (31.6 ml) and the mixture was stirred for an hour at ambient temperature. To a reaction mixture was added a isopropyl ether and the isolated precipitate was collected by filtration. The precipitate was recrystallized from an aqueous ethanol to give 2-(diaminomethyleneamino)-4-(5-ureidomethylfuran-2-yl)thiazole hydrochloride (6.82 g).

mp: 221° C.

IR (Nujol): 3400, 3300, 1695, 1655, 1620, 1590, 1565 cm$^{-1}$.

NMR (DMSO-d$_6$, δ): 4.23 (2H, d, J=5 Hz), 5.67 (2H, s), 6.32 (1H, d, J=3 Hz), 6.55 (1H, t, J=5 Hz), 6.97 (1H, d, J=3 Hz), 7.31 (1H, s), 8.35 (4H, s).

Anal. Calcd. for C$_{10}$H$_{12}$N$_6$O$_2$S.HCl.H$_2$O: C 35.88, H 4.22, N 25.10, Cl 10.58, H$_2$O 5.38 Found: C 35.77, H 4.47, N 25.08, Cl 10.79, H$_2$O 5.63.

EXAMPLE 57

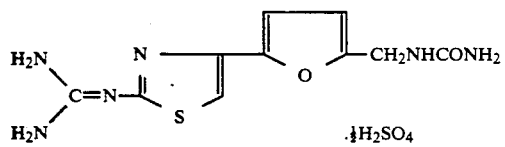

A solution of conc. sulfuric acid (0.7 ml) in methanol (10 ml) was added to a mixture of 2-(diaminomethyleneamino)-4-(5-ureidomethylfuran-2-yl)thiazole (4.0 g) in methanol (60 ml) and the mixture was stirred for an hour at ambient temperature. The isolated precipitate was collected by filtration and the precipitate was recrystallized from an aqueous ethanol to give 2-(diaminomethyleneamino)-4-(5-ureidomethylfuran-2-yl)thiazole hemisulfate (4.26 g).

mp: 170° to 172° C.

IR (Nujol): 3400, 3290, 1690, 1650, 1620, 1580, 1565, 1510 cm$^{-1}$.

NMR (DMSO-d$_6$, δ): 4.21 (2H, d, J=6 Hz), 5.61 (2H, s), 6.29 (1H, d, J=3 Hz), 6.45 (1H, t, J=6 Hz), 6.80 (1H, d, J=3 Hz), 7.09 (1H, s), 7.86 (4H, s).

EXAMPLE 58

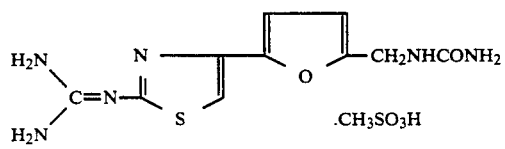

Methanesulfonic acid (0.93 ml) was added to a mixture of 2-(diaminomethyleneamino)-4-(5-ureidomethylfuran-2-yl)thiazole (4.0 g) in methanol (60 ml) and the mixture was stirred for an hour at ambient temperature. The isolated precipitate was collected by filtration and the precipitate was recrystallized from a solution of an aqueous ethanol to give 2-(diaminomethyleneamino)-4-(5-ureidomethylfuran-2-yl)thiazole methanesulfonate (2.77 g). mp: 185° to 186° C.

IR (Nujol): 3325, 3125, 1690, 1604 (br), 1545, 1510, 1045 cm$^{-1}$.

NMR (DMSO-d$_6$, δ): 2.48 (3H, s), 4.22 (2H, d, J=5 Hz), 5.62 (2H, s), 6.32 (1H, d, J=3 Hz), 6.48 (1H, t, J=5 Hz), 6.95 (1H, d, J=3 Hz), 7.32 (1H, s), 8.34 (4H, s), 12.12 (1H, s).

Anal. Calcd. for C$_{10}$H$_{12}$N$_6$O$_2$S.CH$_3$SO$_3$H: C 35.10, H 4.28, N 22.33 Found: C 34.96, H 4.22, N 22.35.

EXAMPLE 59

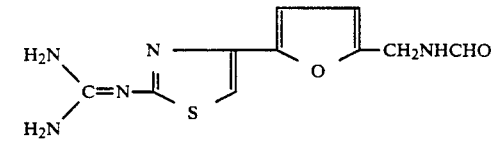

A mixture of acetic anhydride (2.4 ml) and formic acid (1.0 ml) was stirred for 30 minutes at 50° to 60° C. The above mixture was added to a mixture of 4-(5-aminomethylfuran-2-yl)-2-(diaminomethyleneamino)-thiazole (1.5 g) in tetrahydrofuran (15 ml) and N,N-dimethylformamide (15 ml) at ambient temperature and the mixture was stirred for 2.5 hours at ambient temperature. To the reaction mixture was added a mixture of ethyl acetate, tetrahydrofuran and water and the mixture was adjusted to pH 9.5 with 20% aqueous potassium carbonate. The separated organic layer was washed with a brine and dried over magnesium sulfate. The solvent was removed by concentratoin in vacuo and the residue was recrystallized from a mixture of methanol, dioxane and tetrahydrofuran to give 2-(diaminomethyleneamino)-4-(5-formamidomethylfuran-2-yl)thiazole (0.80 g).

mp: 179° to 181° C.

IR (Nujol): 3350, 3310, 3130, 1650, 1530 cm$^{-1}$.

NMR (DMSO-d$_6$, δ): 4.36 (2H, d, J=6 Hz), 6.37 (1H, d, J=3 Hz), 6.78 (1H, d, J=3 Hz), 7.11 (1H, s), 8.11 (1H, s), 8.56 (4H, s).

EXAMPLE 60

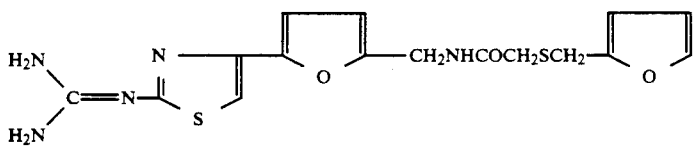

The mixture of 4-(5-aminomethylfuran-2-yl)-2-(diaminomethyleneamino)thiazole (4.0 g), furfurylthioacetic acid (3.4 g) and 1-(3-dimethylaminopropyl)-3-ethylcarbodiimide hydrochloride (4.2 g) in N,N-dimethylformamide (40 ml) was stirred for 15 hours at ambient temperature. The mixture was added a mixture of ethyl acetate, tetrahydrofuran and water and the mixture was adjusted to pH 9.5 with potassium carbonate. The separated organic layer was washed with a brine and dried over magnesium sulfate. Evaporation of a solvent gave a residue, which was purified by column chromatography on silica gel eluting with a mixture of ethyl acetate and methanol (9:1, V/V). The eluted fractions containing the desired product were collected and evaporated in vacuo. The residue was recrystallized from a mixture of methanol, dioxane, and isopropyl ether to give 2-(diaminomethyleneamino)-4-[5-{(furan-2-yl)methylthio}acetamidomethylfuran-2-yl]thiazole (3.50 g).

mp: 180° to 181° C.

IR (Nujol): 3400, 3190, 1655, 1630, 1610, 1530 cm$^{-1}$.

NMR (DMSO-d$_6$, δ): 3.14 (2H, s), 3.85 (2H, s), 4.30 (2H, d, J=5 Hz), 6.19-6.44 (3H, m), 6.59 (1H, d, J=3 Hz), 6.74 (1H, s), 6.87 (4H, s), 7.55 (1H, s), 8.48 (1H, t, J=5 Hz).

Anal. Calcd. for C$_{16}$H$_{17}$N$_5$O$_3$S$_2$: C 49.09, H 4.38, N 17.89 Found: C 49.25, H 4.40, N 17.98.

EXAMPLE 61

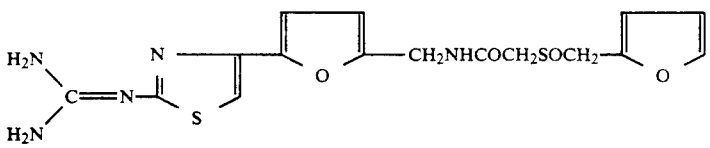

A mixture of 2-(diaminomethyleneamino)-4-[5-{(furan-2-yl)methylthio}acetamidomethylfuran-2-yl]thiazole (1.5 g) and 3-chloroperbenzoic acid (0.9 g) in a mixture of tetrahydrofuran (30 ml) and N,N-dimethylformamide (10 ml) was stirred for 1.5 hours at ambient temperature. To the reaction mixture was added a solution of water and ethyl acetate and the mixture was adjusted to pH 9.5 with 20% aqueous potassium carbonate. The separated organic layer was washed with brine and dried over magnesium sulfate. Evaporation of a solvent gave a residue, which was purified by column chromatography on silica gel eluting with a mixture of ethyl acetate and methanol (9:1, V/V). The eluted fractions containing the desired product were collected and evaporated in vacuo. The residue was recrystallized from a mixture of methanol, dioxane and isopropyl ether to give 2-(diaminomethyleneamino)-4-[5-{(furan-2-yl)methylsulfinyl}acetamidomethylfuran-2-yl]thiazole (1.5 g).

mp: 208° to 209° C.

IR (Nujol): 3425, 3260, 3070, 1650, 1595, 1540 cm$^{-1}$.

NMR (DMSO-d$_6$, δ): 3.16 (1H, d, J=13 Hz), 3.79 (1H, d, J=13 Hz), 4.16 (1H, d, J=14 Hz), 4.34 (2H, d, J=5 Hz), 4.36 (1H, d, J=14 Hz), 6.35 (1H, d, J=3 Hz), 6.44-6.48 (2H, m), 6.61 (1H, d, J=3 Hz), 6.78 (1H, s), 6.89 (4H, s), 7.69 (1H, s), 8.83 (1H, t, J=5 Hz).

Anal. Calcd. for C$_{16}$H$_{17}$N$_5$O$_4$S$_2$: C 47.16, H 4.21, N 17.19 Found: C 47.15, H 4.15, N 17.02.

EXAMPLE 62

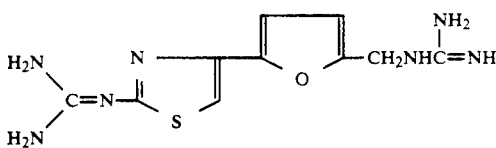

A suspension of 4-(5-aminometnylfuran-2-yl)-2-(diaminomethyleneamino) thiazole (8.0 g) and S-methylisothiourea hemisulfate (11.08) in dimethyl sulfoxide (250 ml) was heated at 100° C. for 6 hours. The resulting precipitate was collected by filtration and then suspended in water (50 ml). The suspension was alkalized to pH 13 with a 4N-sodium hydroxide solution. The resulting precipitate was collected by filtration to afford 2-(diaminomethyleneamino)-4-(5-guanidinomethylfuran-2-yl)thiazole (8.26 g).

NMR (DMSO-d$_6$, δ): 4.30 (2H, s), 6.35 (1H, d, J=3.0 Hz), 6.58 (1H, d, J=3.0 Hz), 6.77 (4H, s), 7.6-6.7 (4H, br).

EXAMPLE 63

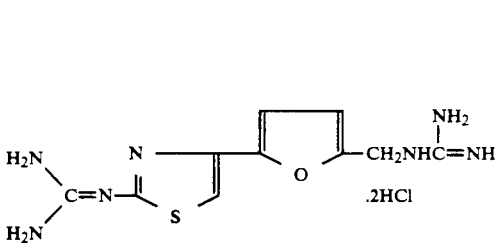

A solution of hydrogen chloride in methanol (0.19 g/ml, 3 ml) was added slowly to a suspension of 2-(diaminomethyleneamino)-4-(5-guanidinomethylfuran-2-yl)thiazole (500 mg) in methanol (10 ml) with cooling on an ice-water bath. The mixture was stirred with cooling on an ice-water bath for 2 hours. The mixture was diluted with diisopropyl ether (20 ml) and the resulting precipitate was collected by filtration. Recrystallization from a mixture of methanol, tetrahydrofuran and diisopropyl ether afforded 2-(diaminomethyleneamino)-4-(5-guanidinomethylfuran-2-yl)thiazole dihydrochloride (340 mg).

mp: 255° C.

IR (Nujol): 3230, 1680, 1620 cm$^{-1}$.

NMR (DMSO-d$_6$, δ): 4.48 (2H, d, J=6.0 Hz), 6.52 (1H, d, J=3.5 Hz), 7.02 (1H, d, J=3.5 Hz), 7.35 (1H, s), 7.45 (4H, s), 8.24 (1H, t, J=6.0 Hz), 8.36 (4H, s), 12.80 (1H, s).

Anal. Calcd. for C$_{10}$H$_{13}$N$_7$OS.2HCl: C 34.10, H 4.29, N 27.84, Cl 20.13 Found: C 34.08, H 4.29, N 27.41, Cl 19.85.

EXAMPLE 64

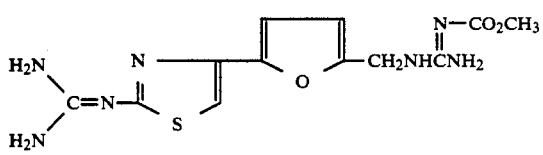

A suspension of 4-(5-aminomethylfuran-2-yl)-2-(diaminomethyleneamino)thiazole (1.6 g), imino(methylthio)methylcarbamic acid methylester (1.2 g) and triethylamine (1.5 g) was stirred at room temperature for 26 hours and then refluxed for 2.5 hours. Imino(methylthio)methylcarbamic acid methylester (1.0 g) was added to the reaction mixture and the mixture was refluxed for 10 hours. The solvent was removed under reduced pressure. The residue was chromatographed on a silica gel column eluting with a mixture of chloroform and methanol (10:1, V/V). Recrystallization from a mixture of methanol and diisopropyl ether afforded 2-(diaminomethyleneamino)-4-[5-(2-methoxycarbonylguanidino)methylfuran-2-yl]thiazole (530 mg).

mp: 199° to 200° C. (dec.).

IR (Nujol): 3450, 3375, 1630 cm$^{-1}$.

NMR (DMSO-d$_6$, δ): 3.48 (3H, s), 4.39 (2H, s), 6.33 (1H, d, J=3.0 Hz), 6.62 (1H, d, J=3.0 Hz), 6.79 (1H, s), 6.90 (4H, s), 7.37 (1H, br).

Anal. Calcd. for C$_{12}$H$_{15}$N$_7$O$_3$S: C 42.72, H 4.48, N 29.06 Found: C 42.92, H 4.62, N 28.82.

EXAMPLE 65

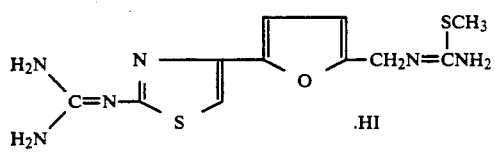

A suspension of 2-(diaminomethyleneamino)-4-(5-thioureidomethylfuran-2-yl)thiazole (1.0 g) and methyl iodide (600 mg) in methanol was stirred at room temperature for 34 hours. The solvent was removed under reduced pressure to afford 2-(diaminomethyleneamino)-4-[5-(2-methyl-3-isothioureido)methylfuran-2-yl]thiazole hydriodide (1.3 g).

NMR (DMSO-d$_6$, δ): 2.63 (3H, s), 4.61 (2H, s), 6.53 (1H, d, J=3.0 Hz), 6.69 (1H, d, J=3.0 Hz), 6.83 (1H, s), 6.80–7.40 (7H, br), 9.42 (1H, br).

EXAMPLE 66

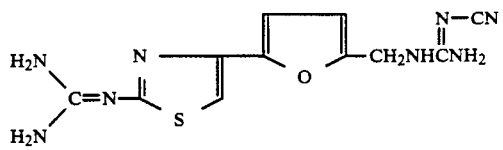

A solution of 2-(diaminomethyleneamino)-4-[5-(2-methyl-3-isothioureido)methylfuran-2-yl]thiazole hydriodide (1.0 g), cyanamide (120 mg) and triethylamine (1.2 g) in N,N-dimethylformamide (20 ml) was heated at 100° C. for 3 hours. The solvent was removed under reduced pressure. The residue was chromatographed on a silica gel column eluting with a mixture of chloroform and methanol (20:1, V/V). Recrystallization from 20% methanol afforded 2-(diaminomethyleneamino)-4-[5-(2-cyanoguanidino)methylfuran-2-yl]thiazole (170 mg).

mp: 224° to 225° C.

IR (Nujol): 3310, 3200, 2180, 1630 cm$^{-1}$.

NMR (DMSO-d$_6$, δ: 4.30 (2H, d, J=5.5 Hz), 6.33 (1H, d, J=3.0 Hz), 6.62 (1H, d, J=3.0 Hz), 6.78 (1H, s), 6.80 (2H, br), 6.88 (4H, s), 7.25 (1H, br).

Anal. Calcd. for C$_{11}$H$_{12}$N$_8$OS.7/10 H$_2$O: C 41.69, H 4.26, N 35.35, H$_2$O 3.98 Found: C 41.61, H 4.33, N 35.00, H$_2$O 3.70.

EXAMPLE 67

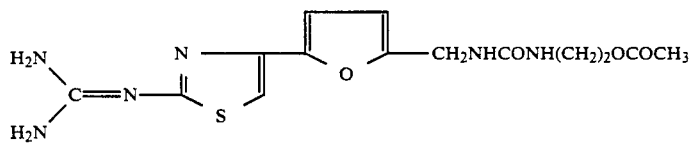

A mixture of 3-acetoxypropionic acid (2.5 g), diphenylphosphorylazide (4.3 ml) and triethylamine (2.6 ml) in dry benzene (50 ml) was stirred for an hour at 75° to 80° C. To the mixture was added to a mixture of 4-(5-aminomethylfuran-2-yl)-2-(diaminomethyleneamino)thiazole (3.0 g) in a solution of tetrahydrofuran (45 ml) and methanol (45 ml) at ambient temperature, and the mixture was stirred for 2.5 hours at the same temperature. Evaporation of a solvent gave a residue, which was purified by column chromatography on silica gel eluting with a mixture of ethyl acetate and methanol (9:1, V/V). The eluted fractions containing the desired product were collected and evaporated in vacuo. The residue was recrystallized from a mixture of methanol, dioxane and isopropyl ether to give 4-[5-{3-(2-acetoxyethyl)ureido}methylfuran-2-yl]-2-(diaminomethyleneamino)thiazole (1.82 g).

mp: 200° to 202° C.

IR (Nujol): 3380, 1725, 1655, 1600, 1550 (br) cm$^{-1}$.

NMR (DMSO-d$_6$, δ): 2.00 (3H, s), 3.07–3.43 (2H, m), 3.97 (2H, t, J=5 Hz), 4.20 (2H, d, J=5 Hz), 6.04 (1H, t, J=5 Hz), 6.19 (1H, d, J=3 Hz), 6.33 (1H, t, J=5 Hz), 6.53 (1H, d, J=3 Hz), 6.70 (1H, s), 6.82 (4H, s).

EXAMPLE 68

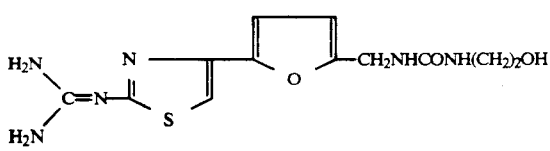

A mixture of 4-[5-{3-(2-acetoxyethyl)ureido}methyl-furan-2-yl]-2-(diaminomethyleneamino)thiazole (1.0 g) in methanol (30 ml) and 1N-sodium hydroxide (8.2 ml) was stirred for 2 hours at ambient temperature. The solvent was removed by concentration in vacuo and to the residue was added a mixture of ethyl acette, tetrahydrofuran and water. The separated organic layer was washed with brine and dried over magnesium sulfate. Evaporation of a solvent gave a residue, which was purified by column chromatography on alumina eluting with a mixture of chloroform and methanol (9:1, V/V). The eluted fractions containing the desired product were collected and evaporated in vacuo. The residue was recrystallized from a mixture of methanol, dioxane and isopropyl ether to give 2-(diaminomethyleneamino)-4-[5-{3-(2-hydroxyethyl)ureido}-methylfuran-2-yl]thiazole (0.42 g).

mp: 201° to 203° C.

IR (Nujol): 3380, 3340, 1635, 1605, 1590 cm$^{-1}$.

NMR (DMSO-d$_6$, δ): 3.00–3.15 (2H, m), 3.28–3.48 (2H, m), 4.22 (2H, d, J=6 Hz), 4.68 (1H, t, J=5 Hz), 6.00 (1H, t, J=6 Hz), 6.24 (1H, d, J=3 Hz), 6.41 (1H, t, J=6 Hz), 6.59 (1H, d, J=3 Hz), 6.76 (1H, s), 6.90 (4H, s).

Anal. Calcd. for C$_{12}$H$_{16}$N$_6$O$_3$S.1/5H$_2$O: C 43.95, H 5.04, N 25.63 Found: C 43.96, H 4.84, N 25.51.

EXAMPLE 69

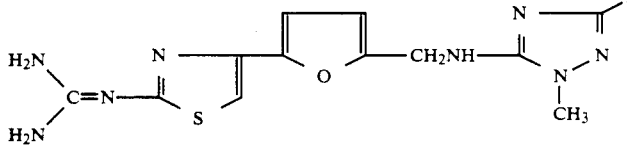

A solution of 4-(5-aminomethylfuran-2-yl)-2-(diaminomethyleneamino)thiazole (1.50 g) and diphenyl cyanocarbonimidate (1.51 g) in methanol (20 ml) was stirred for 4 hours at room temperature. After the solvent was evaporated in vacuo, acetonitrile (20 ml) and methylhydrazine (1.46 g) was added to the residue and the mixture was stirred for three hours at room temperature. The solvent was evaporated in vacuo and the residue was mixed with water. The mixture was made acidic with 6N-hydrochloric acid and washed with diethyl ether. The acidic solution was made basic to pH 11 with aqueous potassium carbonate and the resulting precipitate was collected by filtration. The product was converted to the hydrochloric acid in an usual manner, and which was recrystallized from a mixture of methanol, water and diisopropyl ether to give 4-[5-(3-amino-1-methyl-1H-1,2,4-triazol-5-yl)aminomethylfuran-2-yl]-2-(diaminomethyleneamino)thiazole dihydrochloride (0.61 g).

mp: 184° to 185° C.

IR (Nujol): 3300, 3175, 1675, 1650 cm$^{-1}$.

NMR (DMSO-d$_6$, δ): 3.48 (3H, s), 4.58 (2H, d, J=5 Hz), 6.61 (1H, d, J=3 Hz), 7.04 (1H, d, J=3 Hz), 7.36 (1H, s), 8.43 (4H, s) and 8.91 (1H, t, J=5 Hz).

Anal. Calcd for C$_{12}$H$_{15}$N$_9$OS.2HCl·H$_2$O: C 33.97, H 4.51, N 29.71, Cl 16.71, H$_2$O 4.25 Found: C 34.17, H 4.54, N 29.17, Cl 16.30, H$_2$O 3.77.

EXAMPLE 70

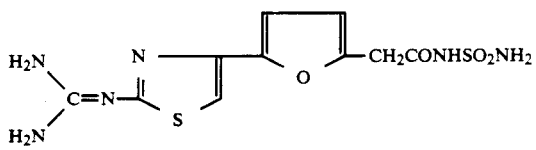

A mixture of 4-[5-(2-amino-2-aminosulfonyliminoethyl)furana-2-yl]-2-(diaminomethyleneamino)thiazole (2.0 g) in N,N-dimethylformamide (15 ml) and 1N-hydrochloric acid (17.5 ml) was stirred for 87 hours at ambient temperature. To a water (50 ml) was added a reaction mixture and the mixture was adjusted to pH 9.5 with 20% aqueous potassium carbonate. The isolated precipitate was collected by filtration and the precipitate was recrystallized from aqueous N,N-dimethylformamide to give 2-(diaminomethyleneamino)-4-(5-sulfamoylaminocarbonylmethylfuran-2-yl)thiazole (1.1 g).

mp: 179° to 181° C.

IR (Nujol): 3350, 3280, 3210, 3100, 1690, 1620, 1580, 1570, 1510 cm$^{-1}$.

NMR (DMSO-d$_6$, δ): 3.68 (2H, S), 6.33 (1H, D, J=3 Hz), 6.63 (1H, d, J=3 Hz), 6.77 (1H, s), 6.92 (4H, s), 7.42 (2H, s).

EXAMPLE 71

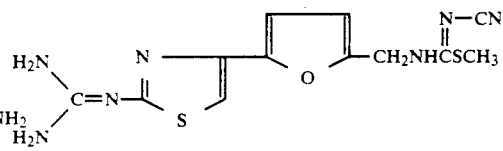

A mixture of 4-(5-aminomethylfuran-2yl)-2-(diaminomethyleneamino)thiazole (8.00 g) and dimethyl-N-cyanodithioiminocarbonate (2.54 g) in ethanol (80 ml) was refluxed for two hours with stirring. After cooling to room temperature, diisopropyl ether (80 ml) was added and the resulting precipitate was collected filtration. Recrystallization from a mixture of N,N-dimethylformamide and ethyl acetate to give 2-(diaminomethyleneamino)-4-[5-(3-cyano-2-methyl-1-isothioureido)methylfuran-3-yl]thiazole (10.2 g).

IR (Nujol): 3450, 3300, 3270, 2165, 1665 cm$^{-1}$.

EXAMPLE 72

The following compound was obtained according to a similar manner to that of Example 1.

2-(Diaminomethyleneamino)-4-]5-(2-methylimidazol-4-yl)furan-2-yl]thiazole dihydrochloride.
mp: >300° C.
IR (KBr): 3000, 1680, 1590 cm$^{-1}$.
NMR (DMSO-d$_6$, δ): 2.64 (3H, s), 7.14 (1H, d, J=3.5 Hz), 7.23 (1H,d, J=3.5 Hz), 7.60 (1H, s), 7.90 (1H, s) and 8.38 (4H, s).

EXAMPLE 73

The following compounds were obtained according to a similar manner to that of Example 1.

(1)

4-[5-(2-Amino-2-aminosulfonyliminoethyl)furan-2-yl)]-2-(diaminomethyleneamino)thiazole.
mp: 222°-225° C. (dec.).
IR (Nujol): 3470, 3450, 3400, 3350, 3320, 3230, 1620, 1530 cm$^{-1}$.
NMR (DMSO-d$_6$, δ): 3.58 (2H, s), 6.28 (1H, d, J=3 Hz), 6.52 (2H, s), 6.56 (1H, d, J=3 Hz), 6.73 (1H, s), 6.81 (4H, s), 7.35 (1H, s), 8.18 (1H, s).

(2)

2-(diaminomethyleneamino)-4-(5-ureidomethylfuran-2-yl)thiazole.
mp: 214°-215° C.
IR (Nujol): 3400, 3320, 3130, 1650, 1590 cm$^{-1}$.
NMR (DMSO-d$_6$, δ): 4.19 (2H, d, J=5 Hz), 5.53 (2H, s), 6.24 (1H, d, J=3 Hz), 6.36 (1H, t, J=5 Hz), 6.59 (1H, d, J=3 Hz), 6.76 (1H, s), 6.87 (4H, s).
Anal. Calcd. for C$_{10}$H$_{12}$N$_6$O$_2$S.1/3 H$_2$O: C 41.95, H, 4.46, N 29.35, H$_2$O 2.10. Found: C 42.04, H 4.53, N 29.04, H$_2$O 2.33.

What we claim is:
1. A compound of the formula:

wherein
R$^1$ and R$^2$ are each hydrogen, furoyl or lower alkyl which may have halogen; or
R$^1$ and R$^2$ are linked together to form lower alkylene,
R$^3$ is hydrogen or lower alkyl,
R$^4$ is amino, carbamoyl, aminocarbamoyl, guanidinocarbamoyl, lower alkylcarbamoyl, sulfamoylaminocarbonyl, lower alkoxycarbonyl, ureido, thioureidosulfamoylamino, lower alkanoylamino, lower alkoxycarbonylamino, lower alkylsulfonylamino, lower alkoxy(lower)alkanoylamino, protected hydroxy(lower)alkanoylamino, lower alkylthio(lower)alkanoylamino, C$_6$–C$_{10}$ aroylamino optionally substituted by nitro, furoylamino, thenoylamino, nicrotinoylamino, 1-oxonicotinoylamino, morpholinocarbonylamino, lower alkylureido, lower alkylthioureido, lower alkanoylureido, lower alkenylureido, C$_6$–C$_{10}$ aroylthioureido, furyl(lower)alkylthio(lower)alkanoylamino, furyl(lower)alkylsulfinyl(lower)alkanoylamino, mono or di (lower)-alkylsulfamoylamino, hydroxy(lower)alkylureido, lower alkylisothioureido, thiazolylamino substituted with lower alkyl, triazolylamino substituted with amino, triazolylamino substituted with amino and lower alkyl, benzoisothiazolylamino substituted with oxo, benzothiadiazinylamino substituted with oxo and halogen, pyrimidinyl substituted with oxo and lower alkyl, triazolyl substituted with amino, or a group of the formula:

$$-(NH)_n-\overset{X-R^5}{\underset{}{C}}-R^6$$

wherein
n is 0 or 1,
X is =CH— or =N—,
R$^5$ is hydrogen, cyano, nitro, carbamoyl, lower alkoxycarbonyl, sulfamoyl, lower alkylsulfonyl, C$_6$–C$_{10}$ arenesulfonyl, which is substituted with one or more substituent(s) selected from lower alkyl, lower alkoxy, halogen and amino, or mono or di(lower)alkylsulfamoyl,
R$^6$ is hydrogen, lower alkyl, lower alkylthio, lower alkoxy, amino, mono or di(lower)alkylamino, lower alkenylamino, lower alkynylamino, hydroxy(lower)alkylamino, lower alkoxy(lower)alkylamino, or mono or di(lower)alkylamino(lower)alkylamino;
A is lower alkylene or —CONH—; or
A—R$^4$ is imidazolyl substituted with lower alkyl or triazolyl substituted with amino, and
Q is hydrogen or lower alkyl.
2. A compound of claim 1, wherein
R$^1$ and R$^2$ are each hydrogen, lower alkyl or trihalo(lower)alkyl; or
R$^1$ and R$^2$ are linked together to form lower alkylene,
R$^4$ is amino, carbamoyl, aminocarbamoyl, guanidinocarbamoyl, lower alkylcarbamoyl, sulfamoylaminocarbonyl, lower alkoxycarbonyl, ureido, thioureido, sulfamoylamino, lower alkanoylamino, lower alkoxycarbonylamino, lower alkylsulfonylamino, lower alkoxy(lower)alkanoylamino, lower alkanoyloxy(lower)alkanoylamino, lower alkylthio(lower)alkanoyloamino, nitrobenzoylamino, furoylamino, thenoylamino, nicotinoylamino, 1-oxonicotinoylamino, morpholinocarbonylamino, 3-lower alkylureido, 3-lower alkylthioureido, 3-lower alkanoylureido, 3-lower alkenylureido, 3-benzoylthioureido, furyl(lower)alkylthio(lower)alkanoylamino, furyl(lower)alkylsulfinyl(lower)alkanoylamino, mono or di(lower)alkylsulfamoylamino, 3-hydroxy(lower)alkylureido, 3-lower alkanoyloxy(lower)alkylureido, 2-lower alkylisothioureido, thiazolylamino substituted with lower alkyl, triazolylamino substuted with amino, triazolylamino substituted with amino and lower alkyl, benzoisothiazolylami8no substituted with oxo, benzothiadiazinylamino substituted with oxo and halogen, pyrimidinyl substituted with oxo and lower alkyl, triazolyl substituted with amino, or a group of the formula:

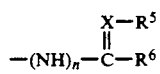

wherein
n, X and $R^6$ are as defined in claim 2,
$R^5$ is hydrogen, cyano, nitro, carbamoyl, lower alkoxycarbonyl, sulfamoyl, lower alkylsulfonyl, phenylsulfonyl substituted with lower alkyl, phenylsulfonyl substituted with lower alkoxy, phenylsulfonyl substituted with halogen, phenylsulfonyl substituted with amino, mono or di(lower)alkylsulfamoyl,
A is as defined in claim 2; or
A—$R^4$ is as defined in claim 2, and
$R^3$ and Q are each as defined in claim 2.

3. A compound of claim 2, wherein
$R^1$ and $R^2$ are each hydrogen,
$R^3$ is hydrogen,
$R^4$ is a group of the formula:

wherein
$R^5$ is sulfamoyl, and
$R^6$ is amino,
A is lower alkylene, and
Q is hydrogen.

4. A compound of claim 3, which is 4-[5-(2-amino-2-sulfamoyliminoethyl)furan-2-yl]-2-(diaminomethyleneamino)thiazole or its hydrochloride or its methanesulfonate.

5. A compound of claim 2, wherein
$R^1$ and $R^2$ are each hydrogen,
$R^3$ is hydrogen,
$R^4$ is ureido or 3-lower alkylureido,
A is lower alkylene, and
Q is hydrogen.

6. A compound of claim 5, which is selected from the group consisting of 2-(diaminomethyleneamino)-4-(5-ureidomethylfuran-2-yl)thiazole or its hydrochloride, and 2-(diaminomethyleneamino)4-[5-(3-methylureido)-methylfuran-2-yl]thiazole or its hydrochloride.

7. An anti-ulcer pharmaceutical composition which comprises, as an active ingredient, an effective amount of a compound of claim 1 or a pharmaceutically acceptable salt thereof in admixture with a pharmaceutically acceptable carrier.

8. A method for the treatment of ulcer which comprises administering an effective amount of a compound of claim 1 or a pharmaceutically acceptable salt thereof to a human or animal.

* * * * *

UNITED STATES PATENT AND TRADEMARK OFFICE
CERTIFICATE OF CORRECTION

PATENT NO. : 5,308,857
DATED : May 3, 1994
INVENTOR(S) : Hisashi TAKASUGI, et al.

It is certified that error appears in the above-indentified patent and that said Letters Patent is hereby corrected as shown below:

On the title page, Item [63] and Column 1, Line 12, the Related U.S. Application date of Ser. No. 07/385,100 should read as follows:

--Jul. 26, 1989--

Signed and Sealed this

Twenty-second Day of November, 1994

Attest:

BRUCE LEHMAN

Attesting Officer

Commissioner of Patents and Trademarks